(12) United States Patent
Albrecht et al.

(10) Patent No.: US 10,301,253 B2
(45) Date of Patent: May 28, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); James Edmund Audia, Cambridge, MA (US); Alexandre Cote, Cambridge, MA (US); Martin Duplessis, Cambridge, MA (US); Victor S. Gehling, Cambridge, MA (US); Andrew Charles Good, Cambridge, MA (US); Jean-Christophe Harmange, Cambridge, MA (US); Yves LeBlanc, Cambridge, MA (US); Christopher G. Nasveschuk, Cambridge, MA (US); Alexander M. Taylor, Cambridge, MA (US); Rishi G. Vaswani, Cambridge, MA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 25 days.

(21) Appl. No.: 15/658,219

(22) Filed: Jul. 24, 2017

(65) Prior Publication Data

US 2018/0009735 A1 Jan. 11, 2018

Related U.S. Application Data

(63) Continuation of application No. PCT/US2016/015440, filed on Jan. 28, 2016.
(Continued)

(51) Int. Cl.
| | |
|---|---|
| C07C 211/39 | (2006.01) |
| C07C 211/38 | (2006.01) |
| C07C 211/17 | (2006.01) |
| C07C 211/19 | (2006.01) |
| A61K 31/137 | (2006.01) |

(Continued)

(52) U.S. Cl.
CPC .......... *C07C 211/42* (2013.01); *A61K 31/135* (2013.01); *A61K 31/166* (2013.01); *A61K 31/196* (2013.01); *A61K 31/277* (2013.01); *A61K 31/337* (2013.01); *A61K 31/351* (2013.01); *A61K 31/397* (2013.01); *A61K 31/40* (2013.01); *A61K 31/415* (2013.01); *A61K 31/4155* (2013.01); *A61K 31/437* (2013.01); *A61K 31/445* (2013.01); *A61K 31/4406* (2013.01); *A61K 31/4545* (2013.01); *A61K 31/4747* (2013.01); *A61K 31/495* (2013.01); *A61K 31/517* (2013.01); *A61K 45/06* (2013.01); *C07C 217/74* (2013.01); *C07C 229/50* (2013.01); *C07C 237/48* (2013.01); *C07C 255/58* (2013.01); *C07C 317/36* (2013.01); *C07D 205/04* (2013.01); *C07D 205/12* (2013.01); *C07D 207/06* (2013.01); *C07D 211/26* (2013.01); *C07D 211/46* (2013.01); *C07D 211/78* (2013.01); *C07D 213/38* (2013.01); *C07D 215/08* (2013.01); *C07D 231/12* (2013.01); *C07D 295/185* (2013.01); *C07D 305/08* (2013.01); *C07D 309/04* (2013.01); *C07D 401/12* (2013.01); *C07D 405/12* (2013.01); *C07C 2601/02* (2017.05);
(Continued)

(58) Field of Classification Search
CPC ... C07C 211/39; C07C 211/38; C07C 211/17; C07C 211/19; A61K 31/137; A61K 31/136; A61K 31/135; A61K 31/4465
USPC ....... 514/765, 764, 278, 409, 462, 331, 325; 558/384; 549/330
See application file for complete search history.

(56) References Cited

FOREIGN PATENT DOCUMENTS

| WO | 2013057320 A1 | 4/2013 | |
|---|---|---|---|
| WO | WO-2013057320 A1 * | 4/2013 | ........... C07D 309/04 |

OTHER PUBLICATIONS

Golub et al., "Molecular Classification of Cancer: Class Discovery and Class Prediction by Gene Expression Monitoring" Science (Oct. 15, 1999), 286: pp. 531-537 (Year: 1999).*
(Continued)

*Primary Examiner* — Matthew P Coughlin
*Assistant Examiner* — Sagar Patel
(74) *Attorney, Agent, or Firm* — Viksnins Harris Padys Malen LLP

(57) ABSTRACT

Provided herein are compounds of formula I:

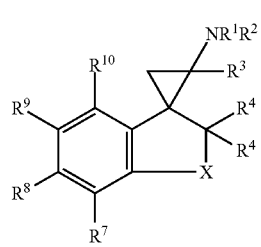

and salts thereof and compositions and uses thereof. The compounds are useful as inhibitors of LSD1. Also included are pharmaceutical compositions comprising a compound of formula I or a pharmaceutically acceptable salt thereof, and
(Continued)

methods of using such compounds and salts in the treatment of various LSD1-mediated disorders.

21 Claims, No Drawings

Related U.S. Application Data

(60) Provisional application No. 62/110,209, filed on Jan. 30, 2015.

(51) Int. Cl.

| | | |
|---|---|---|
| A61K 31/136 | (2006.01) | |
| A61K 31/135 | (2006.01) | |
| A61K 31/4465 | (2006.01) | |
| C07C 211/42 | (2006.01) | |
| C07D 231/12 | (2006.01) | |
| C07D 401/12 | (2006.01) | |
| C07D 405/12 | (2006.01) | |
| C07D 211/78 | (2006.01) | |
| C07D 213/38 | (2006.01) | |
| C07C 255/58 | (2006.01) | |
| C07C 217/74 | (2006.01) | |
| C07C 229/50 | (2006.01) | |
| C07C 237/48 | (2006.01) | |
| A61K 31/166 | (2006.01) | |
| A61K 31/196 | (2006.01) | |
| A61K 31/277 | (2006.01) | |
| A61K 31/337 | (2006.01) | |
| A61K 31/351 | (2006.01) | |
| A61K 31/397 | (2006.01) | |
| A61K 31/40 | (2006.01) | |
| A61K 31/415 | (2006.01) | |
| A61K 31/4155 | (2006.01) | |
| A61K 31/437 | (2006.01) | |
| A61K 31/4406 | (2006.01) | |
| A61K 31/445 | (2006.01) | |
| A61K 31/4545 | (2006.01) | |
| A61K 31/4747 | (2006.01) | |
| A61K 31/495 | (2006.01) | |
| A61K 31/517 | (2006.01) | |
| A61K 45/06 | (2006.01) | |
| C07C 317/36 | (2006.01) | |
| C07D 205/04 | (2006.01) | |
| C07D 205/12 | (2006.01) | |
| C07D 207/06 | (2006.01) | |
| C07D 211/26 | (2006.01) | |
| C07D 211/46 | (2006.01) | |
| C07D 215/08 | (2006.01) | |
| C07D 295/185 | (2006.01) | |
| C07D 305/08 | (2006.01) | |
| C07D 309/04 | (2006.01) | |

(52) U.S. Cl.
CPC ...... *C07C 2601/04* (2017.05); *C07C 2603/94* (2017.05)

(56) References Cited

OTHER PUBLICATIONS

Lala et al., "Role of nitric oxide in tumor progression: Lessons from experimental tumors" Cancer and Metastasis Reviews (1998), 17(1), pp. 91-106. (Year: 1998).*
Chi, et al., "Covalent histone modifications—miswritten, misinterpreted and mis-erased in human cancers", Nature Reviews Cancer 10, 457-469 (2010).
Esteller, "Epigenetics in cancer", N Engl J Med 358(11), 1148-1159 (2008).
Kahl, et al., "Androgen Receptor Coactivators Lysine-Specific Histone Demethylase 1 and Four and a Half LIM Domain Protein 2 Predict Risk of Prostate Cancer Recurrence", Cancer Res 66(23), 11341-11347 (2006).
Kato, et al., "Transrepressive function of TLX requires the histone demethylase LSD1", Mol Cell Biol 28, 3995-4003 (2008).
Kirfel, et al., "Lysine-specific demethylase 1 (LSD1) is highly expressed in ER-negative breast cancers and a biomarker predicting aggressive biology", Carcinogenesis 31(3), 512-520 (2010).
Kirfel, et al., "Lysine-specific demethylase 1 is strongly expressed in poorly differentiated neuroblastoma: implications for therapy", Canc Res 69, 2065-2071 (2009).
Kouzarides, "Chromatin modifications and their function", Cell 128, 693-705 (2007).
Rosenfeld, et al., "Histone methylation-dependent mechanisms impose ligand dependency for gene activation by nuclear receptors", Cell 128, 505-518 (2007).
Schuele, et al., "Cooperative demethylation by JMJD2C and LSD1 promotes androgen receptor-dependent gene expression", Nat Cell Biol 9, 347-353 (2007).
Schuele, et al., "Phosphorylation of histone H3T6 by PKCbeta(I) controls demethylation at histone H3K4", Nature 464(7289), 792-796 (2010).
Schule, et al., "LSD1 demethylates repressive histone marks to promote androgen-receptor-dependent transcription", Nature 437, 436-439 (2005).
Shi, et al., "Histone demethylation mediated by the nuclear amine oxidase homolog LSD1", Cell 119(7), 941-953 (2004).
Sun, et al., Mol Cell Biol 28, 1997-2000 (2010).
Patent Cooperation Treaty, International Searching Authority, Search Report and Written Opinion for PCT/US2016/015440, 10 pages, dated Apr. 14, 2016.

* cited by examiner

THERAPEUTIC COMPOUNDS AND USES THEREOF

CROSS-REFERENCE TO RELATED APPLICATION(S)

This patent application is a continuation of International application serial no. PCT/US2016/015440, filed Jan. 28, 2016, which claims the benefit of priority of U.S. provisional application Ser. No. 62/110,209, filed Jan. 30, 2015, which applications are herein incorporated by reference.

TECHNICAL FIELD OF THE INVENTION

The present invention relates to compounds useful as inhibitors of LSD1.

BACKGROUND OF THE INVENTION

Chromatin modification plays an essential role in transcriptional regulation (T. Kouzarides, 2007, *Cell* 128: 693-705). These modifications, which include DNA methylation, histone acetylation and hsitone methylation, are disregulated in tumors. This epigenetic disregulation plays an important role in the silencing of tumor suppressors and overexpression of oncogenes in cancer (M. Esteller, 2008, *N Engl J Med* 358:1148-59. P. Chi et al, 2010, *Nat Rev Canc* 10:457-469.). The enzymes that regulate histone methylation are the histone methyl transferases and the histone demethylases.

Lysine-specific demethylase 1 (LSD1; also known as BHC110) is a histone lysine demethylase reported to demethylate H3K4mel/2 (Y. Shi et al., 2004, *Cell* 119: 941-953) and H3K9mel/2 (R. Schule et al., 2005, *Nature* 437: 436-439). LSD1 is overexpressed in multiple human cancers, including prostate where it is associated with more frequent relapse (P. Kahl et al., 2006, *Canc. Res.* 66: 11341-11347), breast (J. Kirfel et al., 2010, *Carcinogenesis* 31: 512-520) and neuroblastoma (J. Kirfel et al., 2009, *Canc. Res.* 69: 2065-2071. G. Sun et al., 2010, *Mol. Cell. Biol.* 28: 1997-2000). LSD1 is essential for transcriptional regulation mediated by a number of nuclear hormone receptors, including androgen receptor in prostate cancer (R. Schuele et al., 2005, *Nature* 437: 436-439. R. Schuele et al., 2007, *Nat. Cell Biol.* 9: 347-353. R. Schuele et al., 2010, *Nature* 464: 792796), estrogen receptor in breast carcinomas (M. G. Rosenfeld et al., 2007, *Cell* 128: 505-25518), and TLX receptor in neuorblastoma (S. Kato et al., 2008, *Mol. Cell. Biol.* 28: 3995-4003). These studies have shown that knockdown of LSD1 expression results in decreased cancer cell proliferation. Additionally, LSD1 is overexpressed in multiple cancer types that are nuclear hormone receptor-independent. Those tumors include ER-negative breast (J. Kirfel et al., 2010, *Carcinogenesis* 31: 512-520), small-cell lung, bladder, head & neck, colon, serous ovary, and kidney Wilm's tumor.

There is a need for treatments for cancer and other diseases. There is also a need for inhibitors of LSD1 that may be useful for the treatment of various diseases (e.g., cancer)

SUMMARY OF THE INVENTION

One aspect includes a compound of formula I:

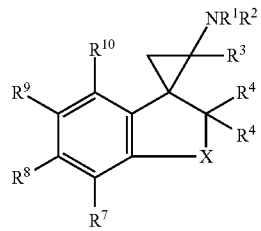

wherein:
X is, —C(R$^5$)$_2$—, —(C(R$^5$)$_2$)$_2$—, —(C(R$^5$)$_2$)$_3$— or —N(R$^6$)C(R$^5$)$_2$—;
R$^1$ is hydrogen, C$_{1-6}$alkyl, C$_{2-6}$alkenyl, C$_{2-6}$alkynyl, carbocyclyl or heterocyclyl, wherein any C$_{1-6}$alkyl, C$_{2-6}$alkenyl or C$_{2-6}$alkynyl of R$^1$ is optionally substituted with one or more R$^{a1}$ groups; and wherein any carbocyclyl or heterocyclyl of R$^1$ is optionally substituted with one or more R$^{a2}$ groups;
R$^2$ is hydrogen or C$_{1-6}$alkyl;
R$^3$ is hydrogen or C$_{1-6}$alkyl;
each R$^4$ is independently selected from the group consisting of hydrogen, halogen and methyl;
each R$^5$ is independently selected from the group consisting of hydrogen, halogen and methyl;
R$^6$ is hydrogen, C$_{1-6}$alkyl or —C(O)OR$^{b1}$;
R$^7$ is hydrogen, halo, C$_{1-6}$alkyl, C$_{2-6}$alkenyl, C$_{2-6}$alkynyl, heterocyclyl, —OR$^{c1}$, CN, —C(O)—N(R$^{c2}$)$_2$, —S(O)$_2$—R$^{c2}$ or —C(O)—OR$^{c2}$, wherein any C$_{1-6}$alkyl, C$_{2-6}$alkenyl or C$_{2-6}$alkynyl of R$^7$ is optionally substituted with one or more R$^{c3}$ groups and wherein any heterocyclyl of R$^7$ is optionally substituted with one or more R$^{24}$ groups;
R$^8$ is hydrogen, halo, C$_{1-6}$alkyl, C$_{2-6}$alkenyl, C$_{2-6}$alkynyl, heterocyclyl, —OR$^{d1}$, CN, —C(O)—N(R$^{d2}$)$_2$, —S(O)$_2$—R$^{d2}$ or —C(O)—OR$^{d2}$, wherein any C$_{1-6}$alkyl, C$_{2-6}$alkenyl or C$_{2-6}$alkynyl of R$^8$ is optionally substituted with one or more R$^{d3}$ groups and wherein any heterocyclyl of R$^8$ is optionally substituted with one or more R$^{d4}$ groups;
R$^9$ is hydrogen, halo, C$_{1-6}$alkyl, C$_{2-6}$alkenyl, C$_{2-6}$alkynyl, heterocyclyl, —OR$^{e1}$, CN, —C(O)—N(R$^{e2}$)$_2$, —S(O)$_2$—R$^{e2}$ or —C(O)—OR$^{e2}$, wherein any C$_{1-6}$alkyl, C$_{2-6}$alkenyl or C$_{2-6}$alkynyl of R$^9$ is optionally substituted with one or more R$^{e3}$ groups and wherein any heterocyclyl of R$^9$ is optionally substituted with one or more R$^{e4}$ groups;
R$^{10}$ is hydrogen, halo, C$_{1-6}$alkyl, C$_{2-6}$alkenyl, C$_{2-6}$alkynyl, heterocyclyl, —OR$^{f1}$, CN, —C(O)—N(R$^{f2}$)$_2$, —S(O)$_2$—R$^{f2}$ or —C(O)—OR$^{f2}$, wherein any C$_{1-6}$alkyl, C$_{2-6}$alkenyl or C$_{2-6}$alkynyl of R$^{10}$ is optionally substituted with one or more R$^{f3}$ groups and wherein any of R$^{10}$ is optionally substituted with one or more R$^{f4}$ groups;
each R$^{a1}$ is independently halo, oxo, —N(R$^{a3}$)$_2$, carbocyclyl, or heterocyclyl, wherein any carbocyclyl or heterocyclyl of R$^{e1}$ is optionally substituted with one or more groups independently selected from the group consisting or halo, C$_{1-6}$alkyl, —N(R$^{a3}$)$_2$, —OR$^{a3}$, —C(O)OR$^{a3}$, —NR$^{a3}$C(O)OR$^{a3}$, —C$_{1-6}$alkylphenyl and —C$_{1-6}$alkylC(O)OR$^{a3}$ wherein the —C$_{1-6}$alkylphenyl is optionally substituted with one or more groups independently selected from the group consisting of halogen, C$_{1-6}$alkyl, —N(R$^{a3}$)$_2$, —C(O)OR$^{a3}$ and —S(O)$_2$—R$^{a3}$;

each $R^{a2}$ is independently halo, —N($R^{a3}$)$_2$ or $C_{1-6}$alkyl, wherein any $C_{1-6}$alkyl of $R^{a2}$ is optionally substituted with one or more —N($R^{a3}$)$_2$;

each $R^{a3}$ is independently hydrogen, $C_{1-6}$alkyl or —$C_{1-6}$alkylphenyl;

$R^{b1}$ is $C_{1-6}$alkyl or —$C_{1-6}$alkylphenyl;

$R^{c1}$ is hydrogen, $C_{1-6}$alkyl or heterocyclyl, wherein any alkyl of $R^{c1}$ is optionally substituted with one or more halo or phenyl, and wherein any heterocyclyl of $R^{c1}$ is optionally substituted with one or more $C_{1-6}$alkyl or —C(=O)O$C_{1-6}$alkyl.

each $R^{c2}$ is independently selected from the group consisting of hydrogen, $C_{1-6}$alkyl, $C_{2-6}$alkenyl and $C_{2-6}$alkynyl, or two $R^{c2}$ groups together with the nitrogen to which they are attached form a 3-7 membered heterocyclyl;

each $R^{c3}$ is independently selected from the group consisting of —S(O)$_2$—$R^{c2}$ and halo;

each $R^{c4}$ is independently selected from the group consisting of $C_{1-6}$alkyl and $C_{1-6}$haloalkyl, wherein any $C_{1-6}$alkyl of $R^{c4}$ is optionally substituted with one or more groups independently selected from the group consisting of $C_{1-6}$alkyl, halo and —S(O)$_2$—$R^{c2}$;

$R^{d1}$ is hydrogen, $C_{1-6}$alkyl or heterocyclyl, wherein any alkyl of $R^{d1}$ is optionally substituted with one or more halo or phenyl, and wherein any heterocyclyl of $R^{d1}$ is optionally substituted with one or more $C_{1-6}$alkyl or —C(=O)O$C_{1-6}$alkyl.

each $R^{d2}$ is independently selected from the group consisting of hydrogen, $C_{1-6}$alkyl, $C_{2-6}$alkenyl and $C_{2-6}$alkynyl, or two $R^{d2}$ groups together with the nitrogen to which they are attached form a 3-7 membered heterocyclyl;

each $R^{d3}$ is independently selected from the group consisting of —S(O)$_2$—$R^{d2}$ and halo;

each $R^{d4}$ is independently selected from the group consisting of $C_{1-6}$alkyl and $C_{1-6}$haloalkyl, wherein any $C_{1-6}$alkyl of $R^{d4}$ is optionally substituted with one or more groups independently selected from the group consisting of $C_{1-6}$alkyl, halo and —S(O)$_2$—$R^{d2}$;

$R^{e1}$ is hydrogen, $C_{1-6}$alkyl or heterocyclyl, wherein any alkyl of $R^{e1}$ is optionally substituted with one or more halo or phenyl, and wherein any heterocyclyl of $R^{e1}$ is optionally substituted with one or more $C_{1-6}$alkyl or —C(=O)O$C_{1-6}$alkyl.

each $R^{e2}$ is independently selected from the group consisting of hydrogen, $C_{1-6}$alkyl, $C_{2-6}$alkenyl and $C_{2-6}$alkynyl, or two $R^{32}$ groups together with the nitrogen to which they are attached form a 3-7 membered heterocyclyl;

each $R^{e3}$ is independently selected from the group consisting of —S(O)$_2$—$R^{e2}$ and halo;

each $R^{e4}$ is independently selected from the group consisting of $C_{1-6}$alkyl and $C_{1-6}$haloalkyl, wherein any $C_{1-6}$alkyl of $R^{e4}$ is optionally substituted with one or more groups independently selected from the group consisting of $C_{1-6}$alkyl, halo and —S(O)$_2$—$R^{e2}$;

$R^{f1}$ is hydrogen, $C_{1-6}$alkyl or heterocyclyl, wherein any alkyl of $R^{f1}$ is optionally substituted with one or more halo or phenyl, and wherein any heterocyclyl of $R^{f1}$ is optionally substituted with one or more $C_{1-6}$alkyl or —C(=O)O$C_{1-6}$alkyl.

each $R^{f2}$ is independently selected from the group consisting of hydrogen, $C_{1-6}$alkyl, $C_{2-6}$alkenyl and $C_{2-6}$alkynyl, or two $R^{f2}$ groups together with the nitrogen to which they are attached form a 3-7 membered heterocyclyl;

each $R^{f3}$ is independently selected from the group consisting of —S(O)$_2$—$R^{f2}$ and halo; and each $R^{f4}$ is independently selected from the group consisting of $C_{1-6}$alkyl and $C_{1-6}$haloalkyl, wherein any $C_{1-6}$alkyl of $R^{f4}$ is optionally substituted with one or more groups independently selected from the group consisting of $C_{1-6}$alkyl, halo and —S(O)$_2$—$R^{f2}$;

or a salt thereof;

provided the compound is not:

3',4'-dihydro-2'H-spiro[cyclopropane-1,1'-naphthalen]-2-amine;

4'-methyl-3',4'-dihydro-2'H-spiro[cyclopropane-1,1'-naphthalen]-2-amine;

7'-methoxy-3',4'-dihydro-2'H-spiro[cyclopropane-1,1'-naphthalen]-2-amine;

4',4'-dimethyl-3',4'-dihydro-2'H-spiro[cyclopropane-1,1'-naphthalen]-2-amine;

6'-methoxy-3',4'-dihydro-2'H-spiro[cyclopropane-1,1'-naphthalen]-2-amine;

2',3'-dihydrospiro[cyclopropane-1,1'-inden]-2-amine;

5'-fluoro-2',3'-dihydrospiro[cyclopropane-1,1'-inden]-2-amine;

6'-methyl-2',3'-dihydrospiro[cyclopropane-1,1'-inden]-2-amine;

4'-fluoro-2',3'-dihydrospiro[cyclopropane-1,1'-inden]-2-amine;

5'-chloro-2',3'-dihydrospiro[cyclopropane-1,1'-inden]-2-amine;

5'-bromo-2',3'-dihydrospiro[cyclopropane-1,1'-inden]-2-amine;

6'-methoxy-2',3'-dihydrospiro[cyclopropane-1,1'-inden]-2-amine; or 6,7,8,9-tetrahydrospiro[benzo[7]annulene-5,1'-cyclopropan]-2'-amine;

or a salt thereof.

Another aspect includes a composition comprising a compound of formula I or a pharmaceutically acceptable salt thereof, and a pharmaceutically acceptable adjuvant, carrier, or vehicle.

Another aspect includes a method of treating cancer in an animal (e.g., a mammal such as a human) comprising administering to the animal in need thereof a compound of formula I or a pharmaceutically acceptable salt thereof as described herein.

Another aspect includes a method of treating an LSD1-mediated disorder in an animal (e.g., a mammal such as a human) comprising administering to the animal in need thereof a compound of formula I or a pharmaceutically acceptable salt thereof as described herein.

Another aspect includes a compound of formula I or a pharmaceutically acceptable salt thereof as described herein for use in medical therapy.

Another aspect includes a compound of formula I or a pharmaceutically acceptable salt thereof as described herein for the prophylactic or therapeutic treatment of cancer.

Another aspect includes the use of a compound of formula I or a pharmaceutically acceptable salt thereof as described herein to prepare a medicament for treating cancer in an animal (e.g., a mammal such as a human).

Another aspect includes a compound of formula I or a pharmaceutically acceptable salt thereof as described herein for the prophylactic or therapeutic treatment of a LSD1-mediated disorder.

Another aspect includes a compound of formula I or a pharmaceutically acceptable salt thereof as described in herein to prepare a medicament for treating a LSD1-mediated disorder in an animal (e.g., a mammal such as a human).

Another aspect includes compounds described herein for the study of LSD1.

Another aspect includes synthetic intermediates and synthetic processes disclosed herein that are useful for preparing a compound of formula I or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O or (=O)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a Spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, propyl, —CH(CH$_3$)$_2$), 1-butyl (n-Bu, n-butyl, —CH$_2$CH$_2$CH$_2$CH$_3$), 2-methyl-1-propyl (i-Bu, butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms.

Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. The term heterocyclyl also includes $C_3$-$C_8$heterocycloalkyl, which is a saturated or partially unsaturated mono-, bi-, or spiro-ring system comprising 3-8 carbons and one or more (1, 2, 3, or 4) heteroatoms.

In one example, heterocyclyl includes 3-12 ring atoms and includes monocycles, bicycles, tricycles and Spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, SO$_2$), and any nitrogen heteroatom may optionally be quaternized (e.g. [NR$_4$]$^+$Cl$^-$, [NR$_4$]$^+$OH$^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "polycycle" refers to a ring system with two or more (e.g. 2, 3, 4, or 5) rings that may be fused, bridged or in a spiro relationship.

As used herein, the term "inhibitor" refers to a compound that binds to and inhibits LSD1 with measurable affinity and activity. In certain embodiments, an inhibitor has an $IC_{50}$ or binding constant of less than about 50 µM, less than about 1 µM, less than about 500 nM, less than about 100 nM or less than about 10 nM.

The terms "measurable affinity" and "measurably inhibit," as used herein, refer to a measurable reduction in activity of LSD1 between: (i) a sample comprising a compound of formula I or composition thereof and LSD1, and (ii) an equivalent sample comprising such LSD1, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of described herein (e.g., a compound of formula I). Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound described herein (e.g., a compound of formula I) that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis.

In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

As used herein, "a" or "an" means one or more, unless clearly indicated otherwise. As used herein, "another" means at least a second or more.

Exemplary Values

It is to be understood that two or more of the embodiments described herein below may be combined. It is also to be understood that the embodiments provided herein below are embodiments to the compounds of formula I and alls sub-formulas of I (e.g., Ia, Ib, Ic, Id, Ie, If, Ig).

In one embodiment each $R^4$ is hydrogen.

In one embodiment X is —$C(R^5)_2$—, —$(C(R^5)_2)_2$— or —$(C(R^5)_2)_3$—.

In one embodiment X is —$CH_2$—, —$CH_2CH_2$— or —$CH_2CH_2CH_2$—.

In one embodiment, a compound of formula I is a compound of formula Ia:

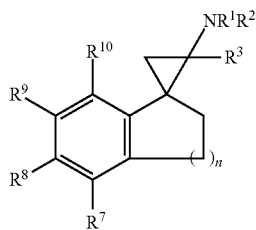

Ia wherein n is 1, 2 or 3; or a salt thereof.

In one embodiment, a compound of formula I is a compound of formula Ic, Id or Ie:

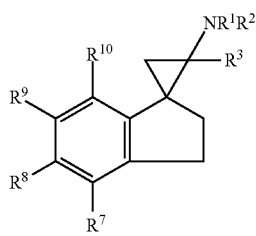

Ic

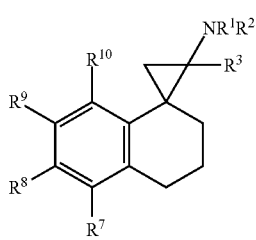

Id

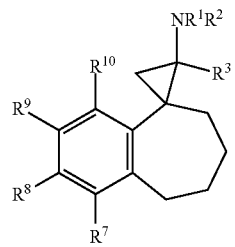

Ie or a salt thereof.

In one embodiment $R^3$ is hydrogen or $C_{1-4}$alkyl.
In one embodiment $R^3$ is hydrogen or methyl.
In one embodiment $R^3$ is hydrogen.
In one embodiment, a compound of formula I is a compound of formula Ib:

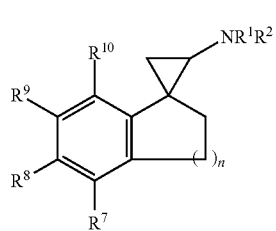

Ib wherein n is 1, 2 or 3; or a salt thereof.

In one embodiment X is or —$N(R^6)C(R^5)_2$—.
In one embodiment $R^5$ is hydrogen.
In one embodiment $R^7$ is hydrogen or halo.
In one embodiment $R^7$ is hydrogen or chloro.
In one embodiment $R^8$ is hydrogen, halo, heteroaryl, CN, —C(O)—N($R^{d2}$)$_2$ or —C(O)—O$R^{d2}$, wherein any heteroaryl of $R^8$ is optionally substituted with one or more $R^{d4}$ groups.
In one embodiment $R^{d1}$ is $C_{1-6}$alkyl wherein any alkyl of $R^{d1}$ is optionally substituted with phenyl.
In one embodiment each $R^{d2}$ is independently selected from the group consisting of hydrogen and $C_{1-6}$alkyl, or two $R^{d2}$ groups together with the nitrogen to which they are attached form a 3-7 membered heterocyclyl.
In one embodiment each $R^{d4}$ is independently $C_{1-6}$alkyl.
In one embodiment $R^8$ is

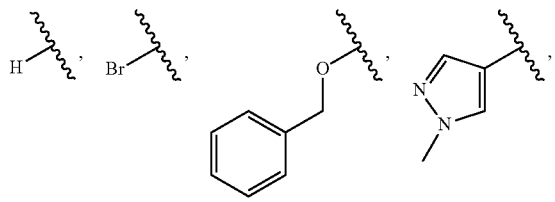

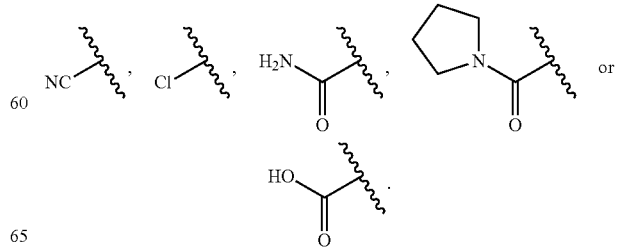

or

In one embodiment $R^9$ is hydrogen, halo, $C_{1-6}$alkyl, heteroaryl, CN, —C(O)N($R^{e2}$)$_2$, —S(O)$_2$—$R^{e2}$ or —C(O)—O$R^{e2}$, wherein any $C_{1-6}$alkyl of $R^9$ is optionally substituted with one or more $R^{e3}$ groups and wherein any heteroaryl of $R^9$ is optionally substituted with one or more $R^{e4}$ groups.

In one embodiment each $R^{e2}$ is independently selected from the group consisting of hydrogen and $C_{1-6}$alkyl.

In one embodiment each $R^{e4}$ is independently $C_{1-6}$alkyl, wherein any $C_{1-6}$alkyl of $R^{e4}$ is optionally substituted with one or more groups independently selected from the group consisting of $C_{1-6}$alkyl, halo and —S(O)$_2$—$R^{e2}$.

In one embodiment $R^9$ is

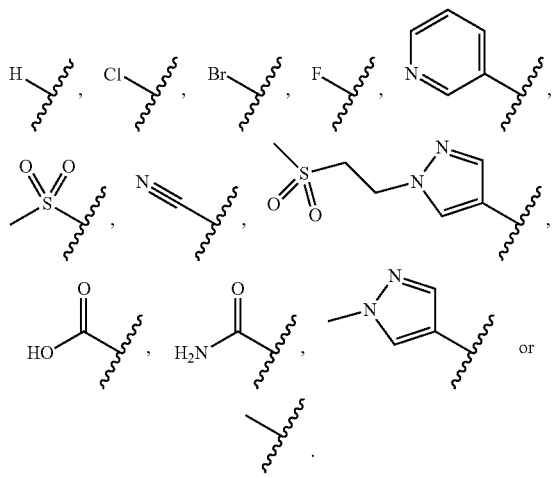

In one embodiment $R^{10}$ is hydrogen or —O$R^{f1}$.

In one embodiment $R^{f1}$ is heterocyclyl, wherein any heterocyclyl of $R^{f1}$ is optionally substituted with one or more —C(=O)O$C_{1-6}$alkyl.

In one embodiment $R^{10}$ is

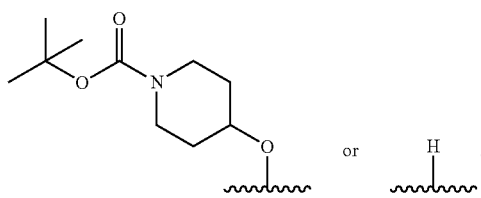

In one embodiment $R^2$ is hydrogen.

In one embodiment, a compound of formula I is a compound of formula If:

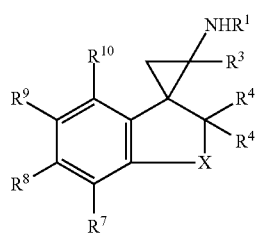

or a salt thereof.

In one embodiment $R^1$ is hydrogen, $C_{1-6}$alkyl, carbocyclyl or heterocyclyl, wherein any $C_{1-6}$alkyl of $R^1$ is optionally substituted with one or more $R^{a1}$ groups, and wherein any carbocyclyl or heterocyclyl of $R^1$ is optionally substituted with one or more $R^{a2}$ groups.

In one embodiment $R^1$ is $C_{1-6}$alkyl, carbocyclyl or heterocyclyl, wherein any $C_{1-6}$alkyl of $R^1$ is optionally substituted with one or more $R^{a1}$ groups, and wherein any carbocyclyl or heterocyclyl of $R^1$ is optionally substituted with one or more $R^{a2}$ groups.

In one embodiment each $R^{a1}$ is independently oxo, —N($R^{a3}$)$_2$, carbocyclyl, aryl or heterocyclyl, wherein any carbocyclyl, aryl or heterocyclyl of $R^{a1}$ is optionally substituted with one or more groups independently selected from the group consisting or halo, $C_{1-6}$alkyl, —N($R^{a3}$)$_2$, —O$R^{a3}$, —C(O)O$R^{a3}$, —$C_{1-6}$alkylphenyl and —$C_{1-6}$alkylC(O)O$R^{a3}$ wherein the —$C_{1-6}$alkylphenyl is optionally substituted with one or more groups independently selected from the group consisting of halogen, $C_{1-6}$alkyl, —N($R^{a3}$)$_2$, —C(O)O$R^{a3}$ and —S(O)$_2$—$R^{a3}$.

In one embodiment each $R^{a2}$ is independently —N($R^{a3}$)$_2$ or $C_{1-6}$alkyl, wherein any $C_{1-6}$alkyl of $R^{a2}$ is optionally substituted with one or more —N($R^{a3}$)$_2$.

In one embodiment each $R^{a3}$ is hydrogen.

In one embodiment $R^1$ is hydrogen,

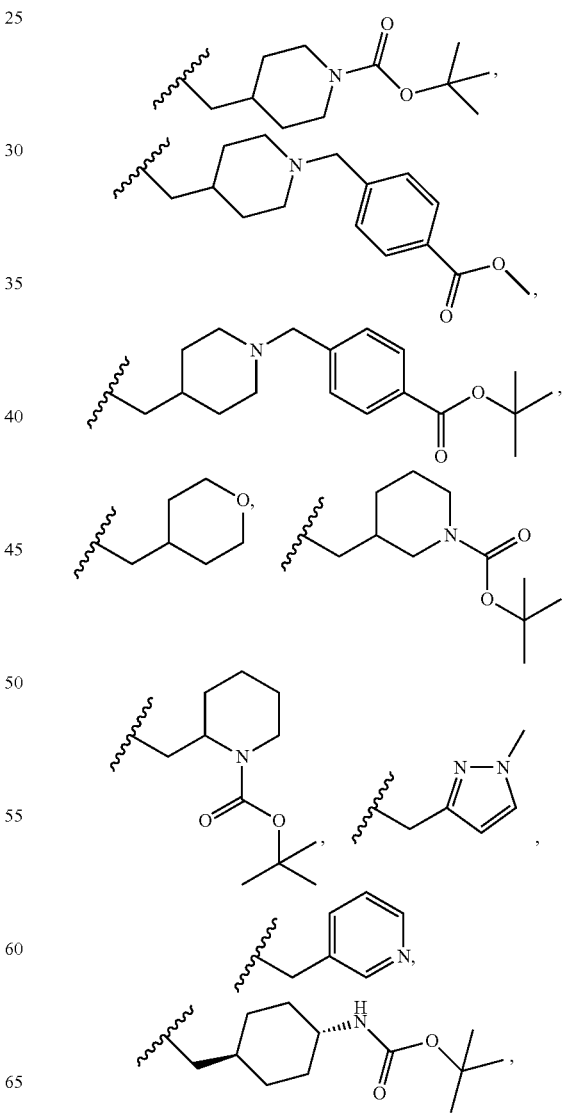

-continued
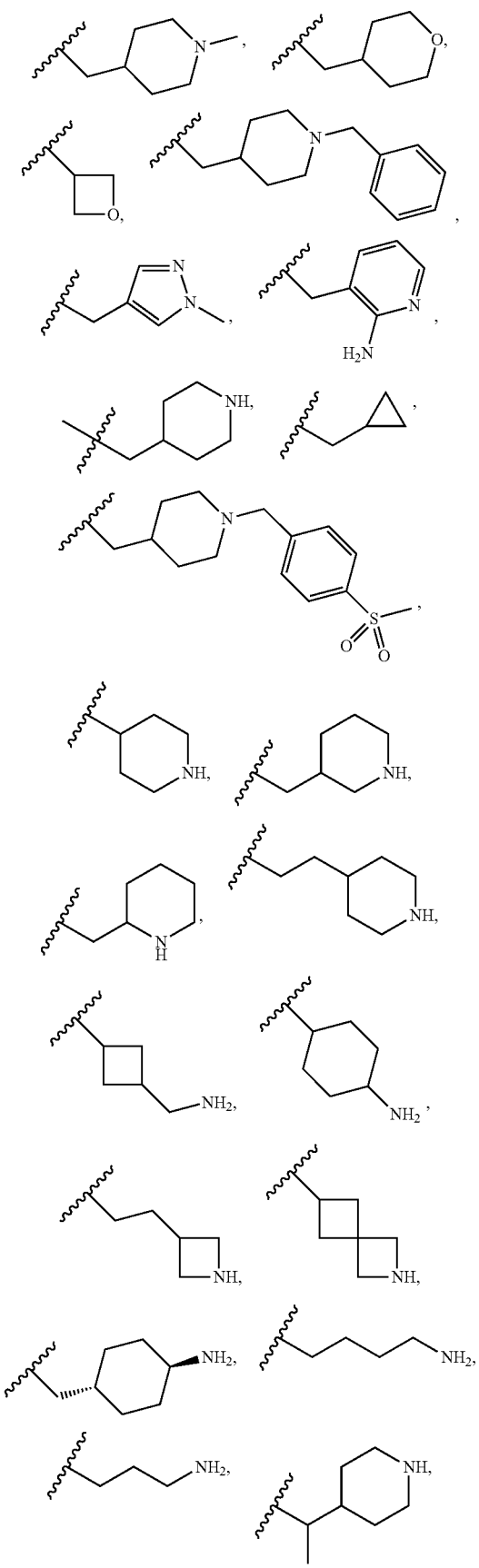
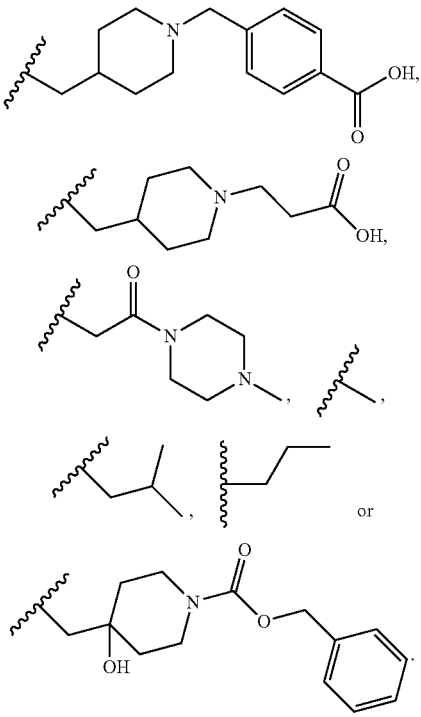
In one embodiment R¹ is
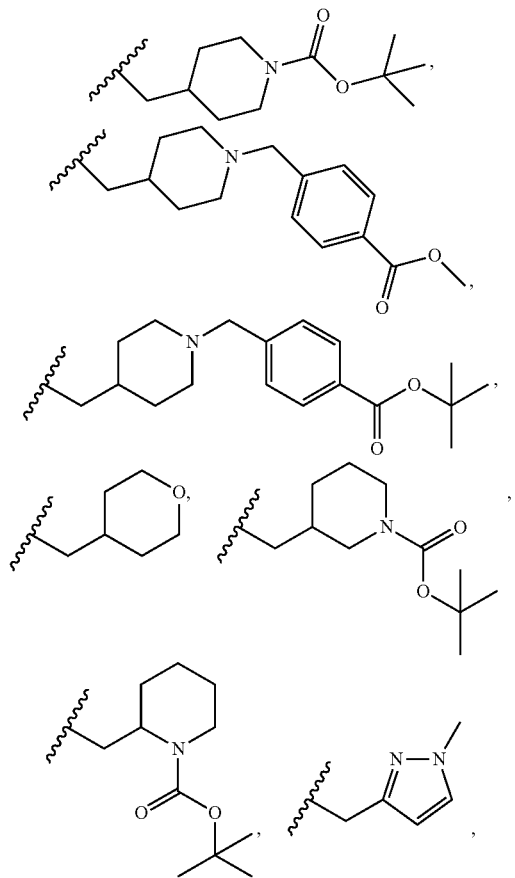

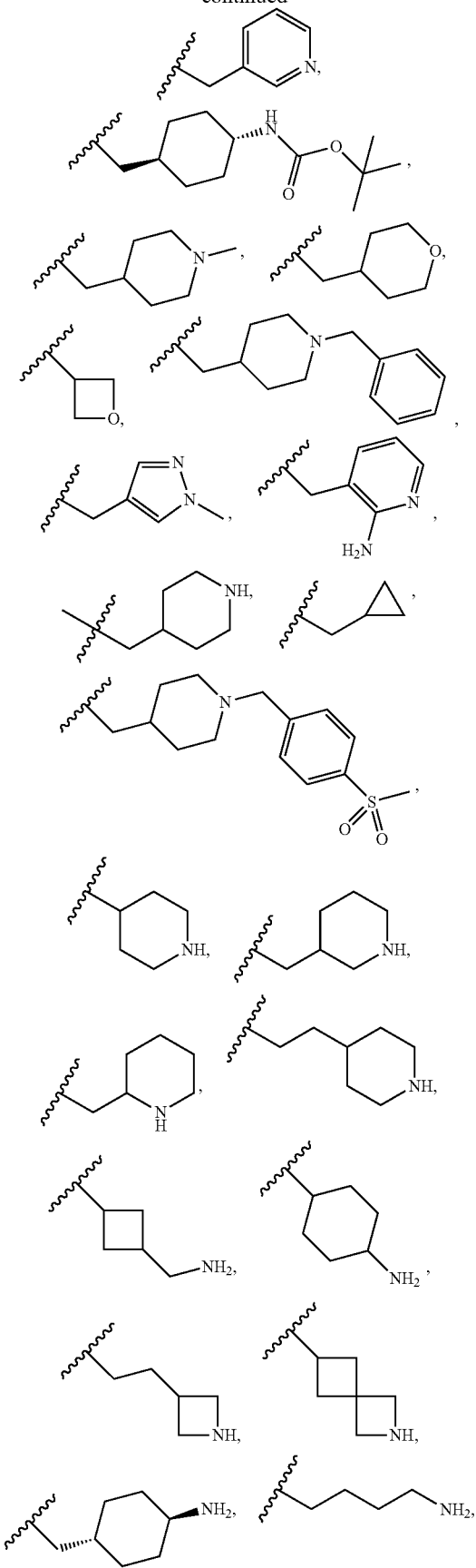
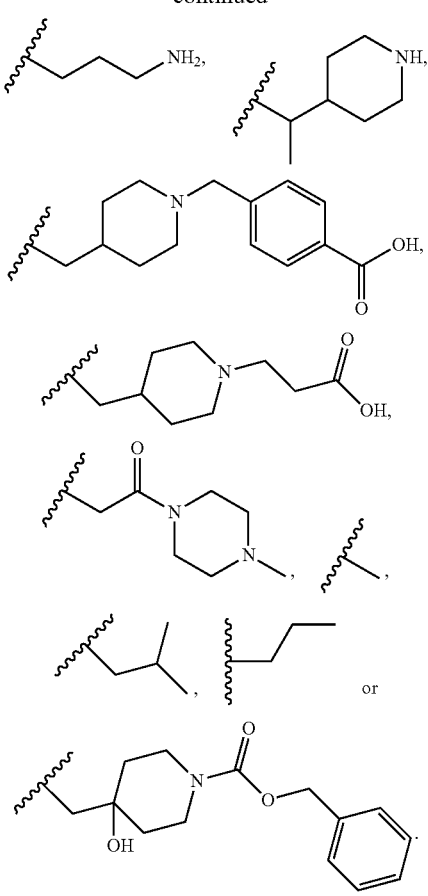
In one embodiment $R^1$ and $R^2$ are each hydrogen.
In one embodiment, a compound of formula I is a compound of formula Ig:
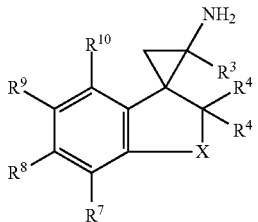
or a salt thereof.
In one embodiment a compound of formula I is:
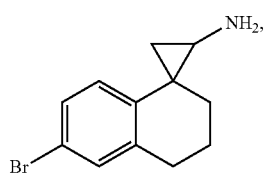

-continued
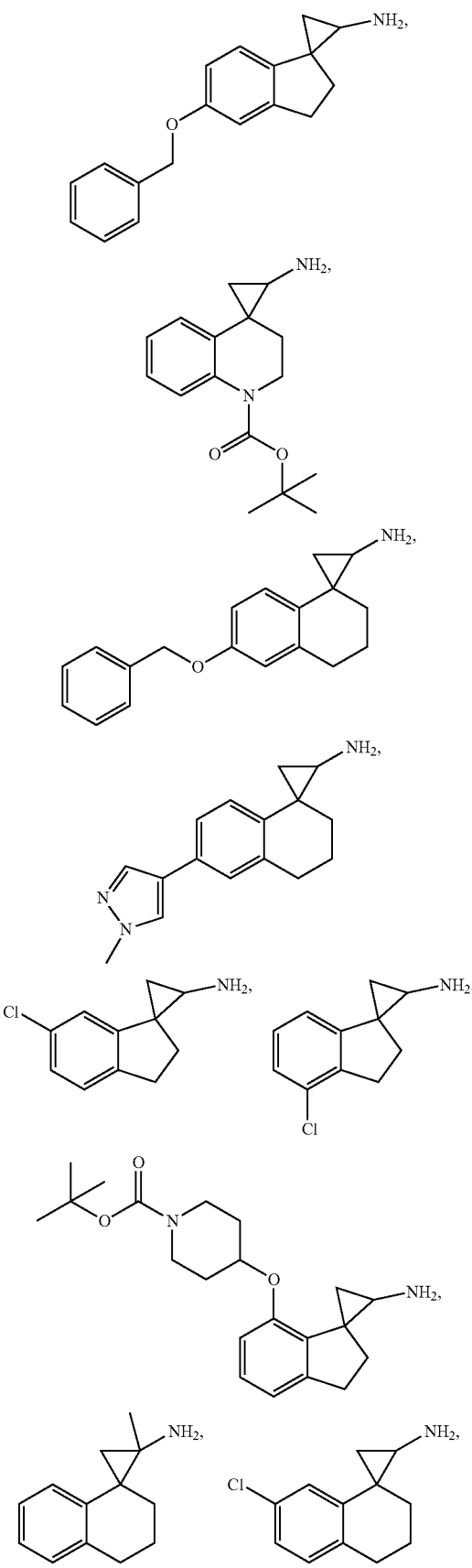
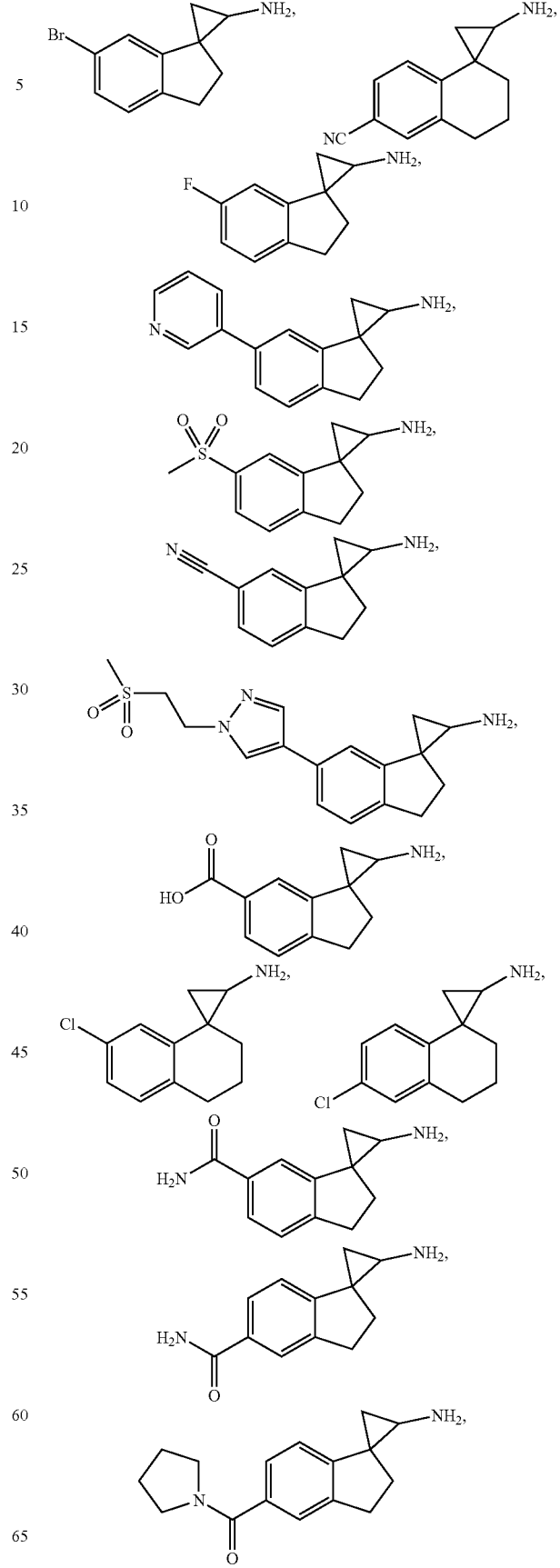

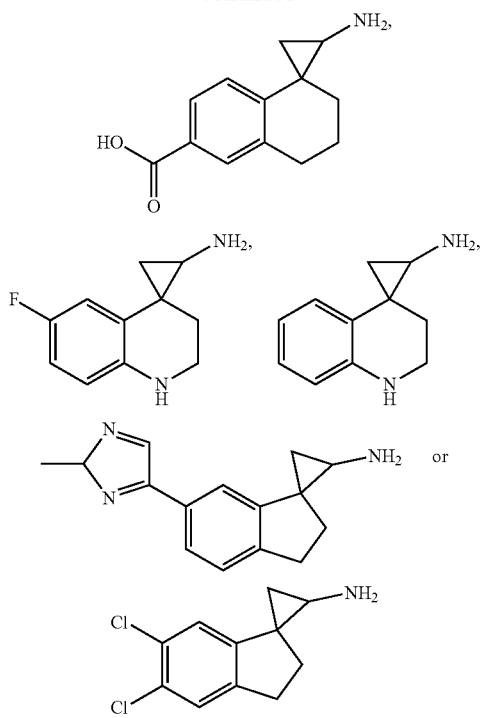
or a salt thereof.
In one embodiment a compound of formula I is:
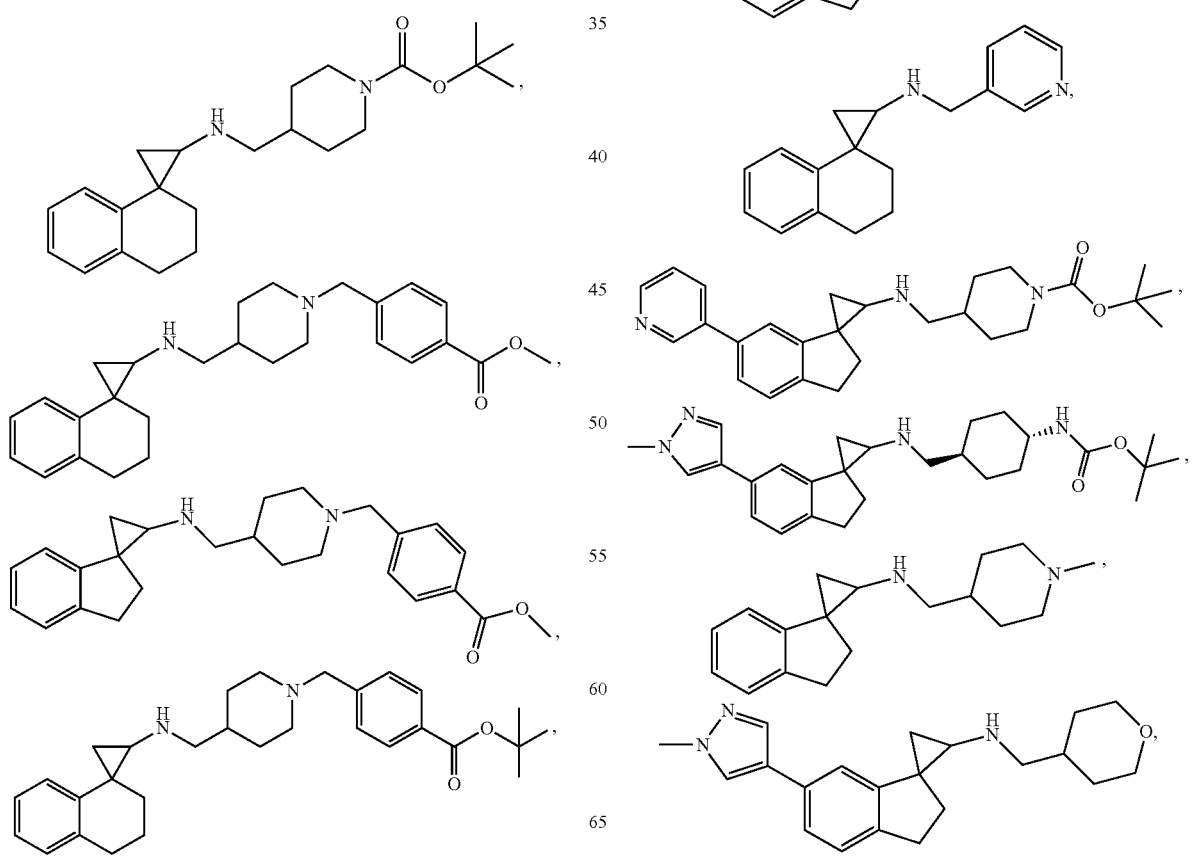

-continued
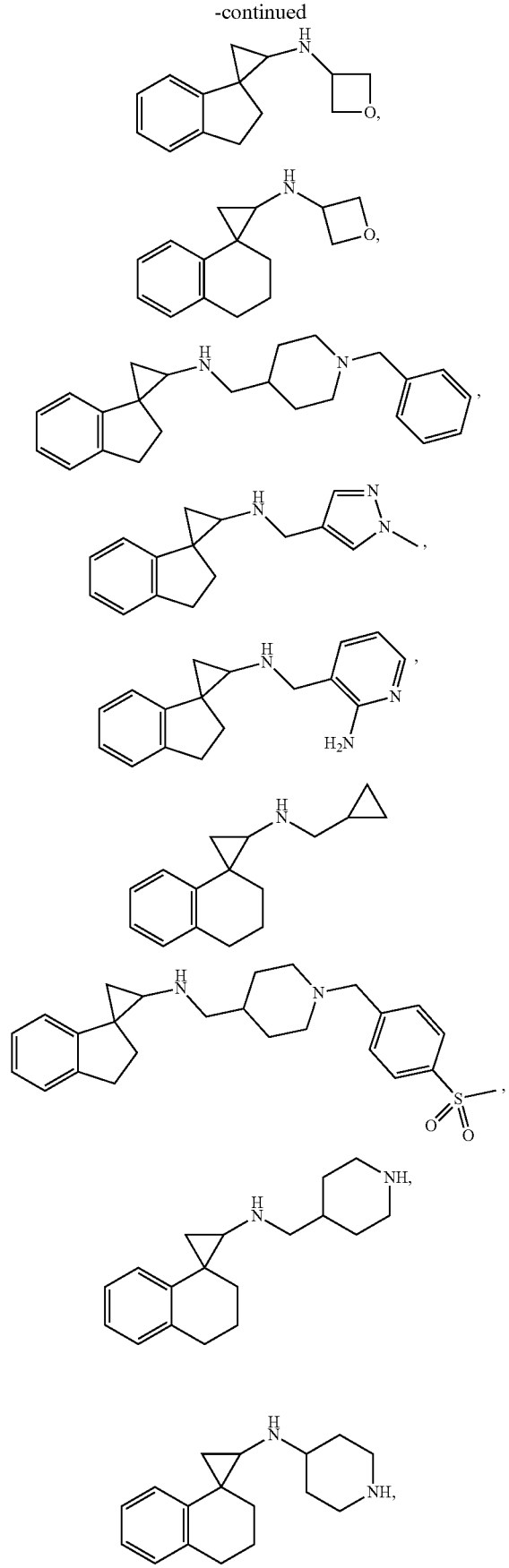
-continued
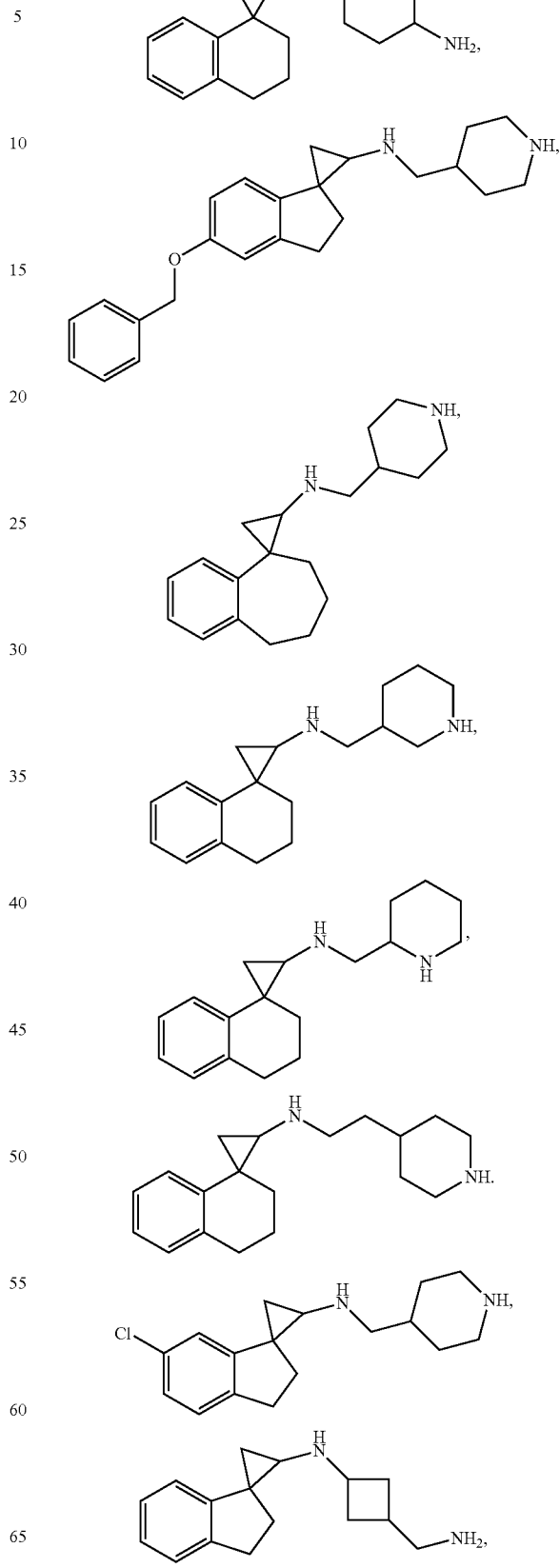

25
-continued
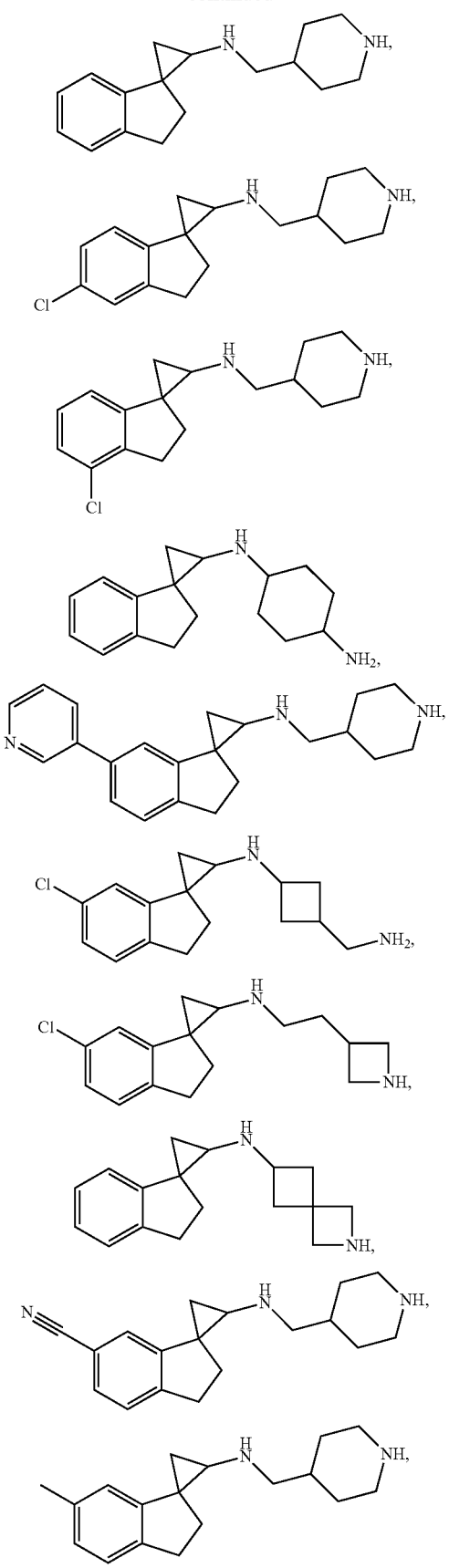
26
-continued
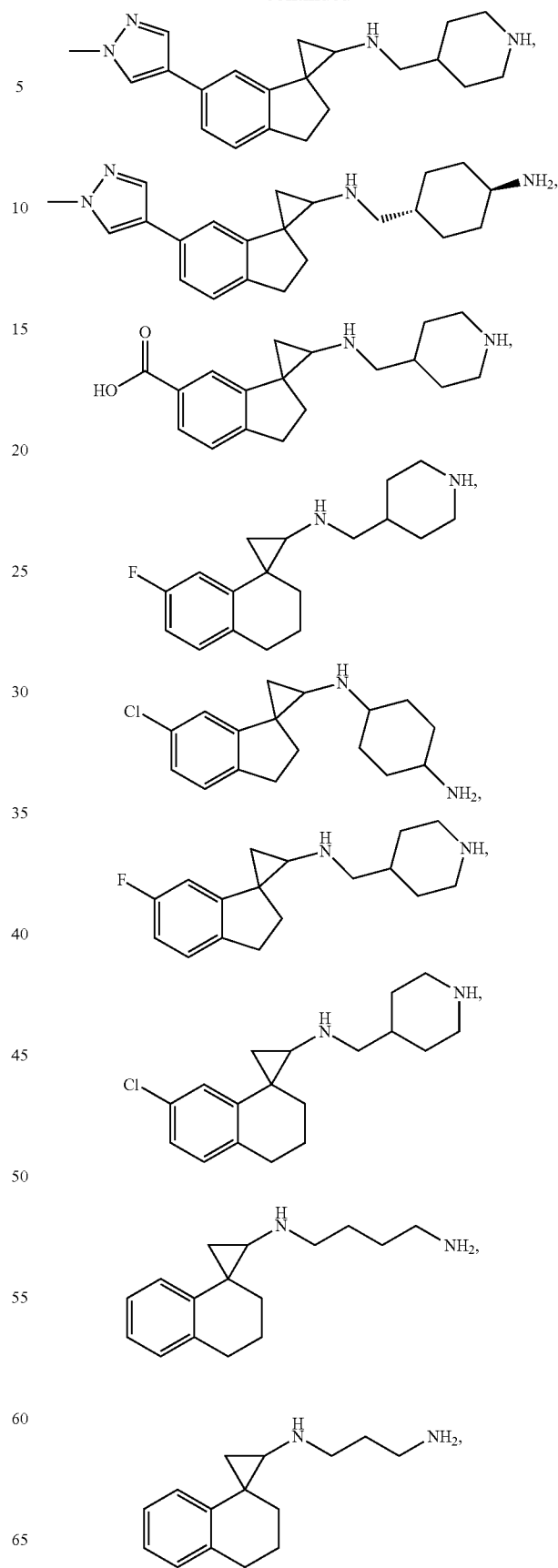

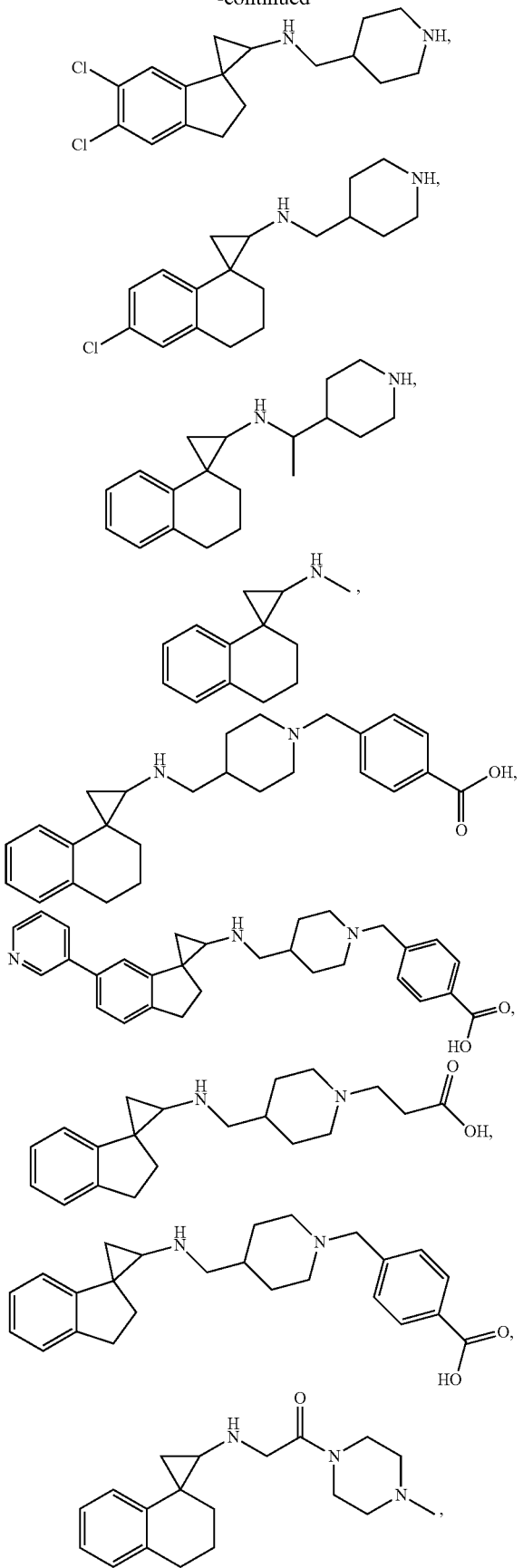
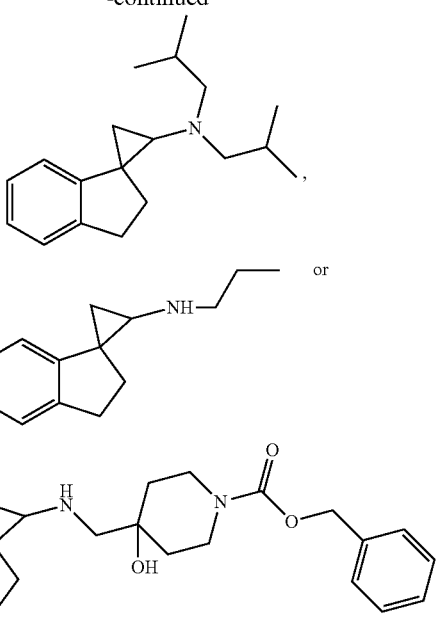
or a salt thereof.
In one embodiment the compounds of formula I do not include:
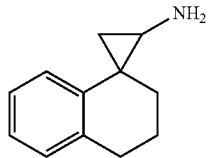
3',4'-dihydro-2'H-spiro[cyclopropane-1,1'-naphthalen]-2-amine
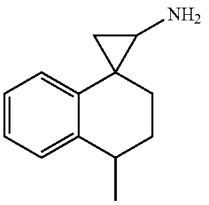
4'-methyl-3',4'-dihydro-2'H-spiro[cyclopropane-1,1'-naphthalen]-2-amine
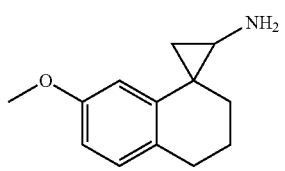
7'-methoxy-3',4'-dihydro-2'H-spiro[cyclopropane-1,1'-naphthalen]-2-amine

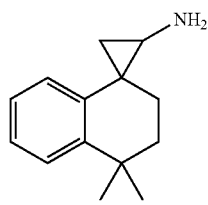

4',4'-dimethyl-3',4'-dihydro-2'H-spiro[cyclopropane-1,1'-naphthalen]-2-amine

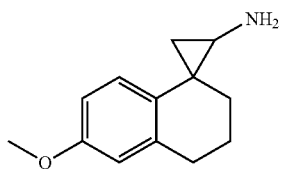

6'-methoxy-3',4'-dihydro-2'H-spiro[cyclopropane-1,1'-naphthalen]-2-amine

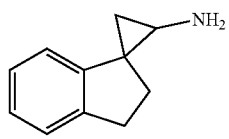

2',3'-dihydrospiro[cyclopropane-1,1'-inden]-2-amine

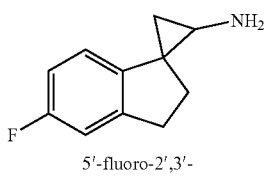

5'-fluoro-2',3'-dihydrospiro[cyclopropane-1,1'-inden]-2-amine

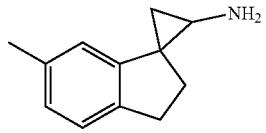

6'-methyl-2',3'-dihydrospiro[cyclopropane-1,1'-inden]-2-amine

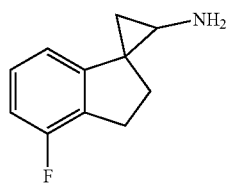

4'-fluoro-2',3'-dihydrospiro[cyclopropane-1,1'-inden]-2-amine

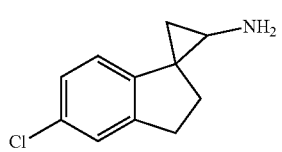

5'-chloro-2',3'-dihydrospiro[cyclopropane-1,1'-inden]-2-amine

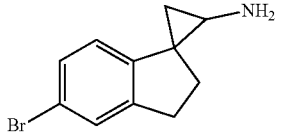

5'-bromo-2',3'-dihydrospiro[cyclopropane-1,1'-inden]-2-amine

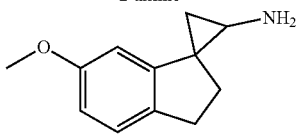

6'-methoxy-2',3'-dihydrospiro[cyclopropane-1,1'-inden]-2-amine

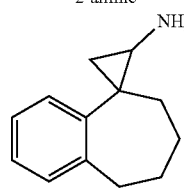

6,7,8,9-tetrahydrospiro[benzo[7]annulene-5,1'-cyclopropan]-2'-amine or a salt thereof.

One embodiment provides a composition comprising a compound disclosed herein or a pharmaceutically acceptable salt thereof, and a pharmaceutically acceptable adjuvant, carrier, or vehicle.

One embodiment provides a method for treating a LSD1-mediated disorder in an animal comprising administering a disclosed herein or a pharmaceutically acceptable salt thereof to the animal.

One embodiment provides a compound disclosed herein or a pharmaceutically acceptable salt thereof for use in medical therapy.

One embodiment provides a compound disclosed herein or a pharmaceutically acceptable salt thereof for the prophylactic or therapeutic treatment of a LSD1-mediated disorder.

One embodiment provides the use of a compound disclosed herein or a pharmaceutically acceptable salt thereof to prepare a medicament for treating a LSD1-mediated disorder in an animal (e.g. a mammal such as a human).

One embodiment provides synthetic intermediates and synthetic processes disclosed herein that are useful for preparing a compounds disclosed herein or a salt thereof.

Uses, Formulation and Administration

Pharmaceutically Acceptable Compositions

Another aspect includes a pharmaceutical composition comprising a compound of formula I or a pharmaceutically acceptable salt thereof or a compound disclosed herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit LSD1. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof or a compound disclosed herein or a pharmaceutically acceptable salt thereof is formulated as a solid dosage form for oral administration. Solid dosage forms for oral administration include capsules, tablets, pills, powders, and granules. In certain embodiments, the solid oral dosage form comprising a compound of formula I or a salt thereof further or a compound disclosed herein or a pharmaceutically acceptable salt thereof comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof or a compound disclosed herein or a pharmaceutically acceptable salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula I or salt thereof or a compound disclosed herein or a salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula I or a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula I or a salt thereof or a compound disclosed herein or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula I or the compound disclosed herein.

Example dosage forms for topical or transdermal administration of a compound of formula I or a compound disclosed herein include ointments, pastes, creams, lotions, gels, powders, solutions, sprays, inhalants or patches. The compound of formula I or a salt thereof or the compound disclosed herein or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula I or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula I or a salt thereof or a compound disclosed herein or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula I or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula I or a salt thereof or a compound disclosed herein or a salt thereof for the inhibition of LSD1 (in vitro or in vivo).

Another embodiment includes a method for treating a LSD1-mediated disorder in an animal comprising administering a compound of formula I, or a pharmaceutically acceptable salt thereof or a compound disclosed herein or a pharmaceutically acceptable salt thereof to the animal. LSD1-mediated disorders include, but are not limited to those disorders described herein.

Another embodiment includes a method of increasing efficacy of a cancer treatment comprising a cytotoxic agent in an animal comprising administering to the animal an effective amount of a compound of formula I or a pharmaceutically acceptable salt thereof or a compound disclosed herein or a pharmaceutically acceptable salt thereof.

Another embodiment includes a method of delaying or preventing development of cancer resistance to a cytotoxic agent in an animal, comprising administering to the animal a compound of formula I or a pharmaceutically acceptable salt thereof or a compound disclosed herein or a pharmaceutically acceptable salt thereof.

Another embodiment includes a method of extending the duration of response to a cancer therapy in an animal, comprising administering to an animal undergoing the cancer therapy a compound of formula I or a pharmaceutically acceptable salt thereof or a compound disclosed herein or a pharmaceutically acceptable salt thereof, wherein the duration of response to the cancer therapy when the compound of formula I or the pharmaceutically acceptable salt or a compound disclosed herein or a pharmaceutically acceptable salt thereof is administered is extended over the duration of response to the cancer therapy in the absence of the administration of the compound of formula I or the pharmaceutically acceptable salt thereof or a compound disclosed herein or a pharmaceutically acceptable salt thereof.

Another embodiment includes a method of treating cancer in an individual comprising administering to the individual (a) a compound of formula I or a pharmaceutically acceptable salt thereof or a compound disclosed herein or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

LSD1-Mediated Disorders

A "LSD1-mediated disorder" is characterized by the participation LSD1 in the inception, manifestation of one or more symptoms or disease markers, severity, or progression of a disorder.

LSD1-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

In certain embodiments, the cancer is brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, giant cell tumor of bone or thyroid cancer.

LSD1-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

LSD1-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

LSD1 has been shown to be involved in the reactivation of viruses (e.g., herpes simplex virus (HSV), a-herpes virus, varicella zoster virus (VZV)), from latency (Liang et al., 2009, Nature Medicine, 15(11) 1312-1317). Accordingly, LSD1 inhibitors may be useful for treating or preventing viral diseases or conditions.

Co-Administration of Compounds and Other Agents

The compounds of formula I or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula I such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula I or a salt thereof or a compound disclosed herein or a pharmaceutically acceptable salt thereof and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula I or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethypamino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal antiinflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; antiinflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula I or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RL siL-1RII, siL-6R), an antiinflammatory cytokine (e.g. IL-4, IL-1 0, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCIO-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula I or a pharmaceutically acceptable salt thereof may be co-administered with methotrexate or leflunomide. In moderate or severe rheumatoid arthritis cases, a compound of formula I or a pharmaceutically acceptable salt thereof may be co-administered with cyclosporine and anti-TNF antibodies as noted above. A compound of formula I or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula I or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula I or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula I or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(Alfa Wassermann/J&J), interferon 1A-1F (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula I or a pharmaceutically acceptable salt therof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula I or a pharmaceutically acceptable salt therof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-10, IL-13 or TGF).

A compound of formula I or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, a n anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula I or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula I or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula I or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula I or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula I or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula I or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor of PDE4, or a purine synthesis inhibitor (e.g. Cellcept®). For example, a compound of formula I or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula I or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula I or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula I or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™)).

A compound of formula I or a pharmaceutically acceptable salt thereof can also be co-administered with one or more agents used in the prevention or treatment of AIDS: an HIV reverse transcriptase inhibitor, a n HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula I or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula I or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula I or salt thereof or a compound disclosed herein or a salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula I or the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula I or a pharmaceutically acceptable salt thereof or a compound disclosed herein or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS #878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula I or a pharmaceutically acceptable salt thereof or a compound disclosed herein or a pharmaceutically acceptable salt thereof is concomitantly administered with the cytotoxic agent (e.g., targeted therapy, chemotherapy, and/or radiotherapy). In certain embodiments, the compound of formula I or a pharmaceutically acceptable salt thereof is administered prior to and/or concurrently with the cytotoxic agent (e.g., targeted therapy, chemotherapy, and/or radiotherapy).

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

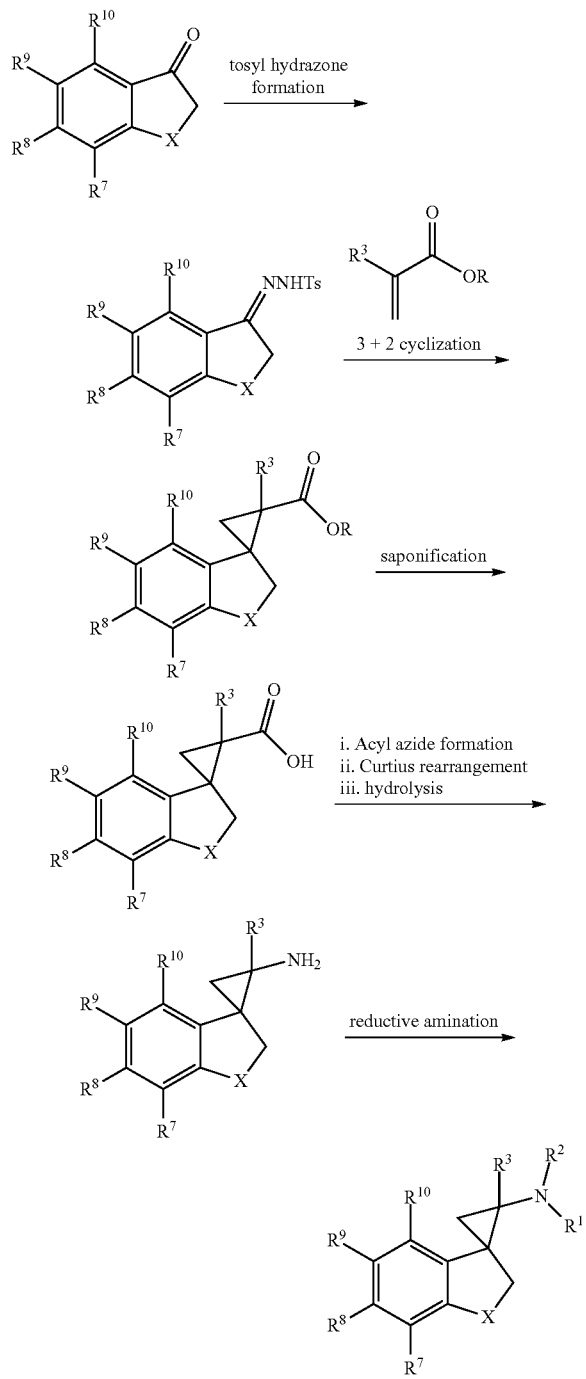

List of Abbreviations

| ACN | acetonitrile |
| Boc | tert-butoxycarbonyl |
| Br$_2$ | bromine |
| Cs$_2$CO$_3$ | cesium carbonate |
| DCM | dichloromethane |
| DIPEA | N,N-diiopropylethyl amine |
| DMF | N,N-dimethylformamide |
| DMSO | dimethylsulphoxide |
| DMAP | deoxyadenosine monophosphate |
| EDC | N-(3-Dimethylaminopropyl)-N'-ethylcarbodiimide hydrochloride |
| EtOAc | ethyl acetate |
| EtOH | ethanol |
| h | hour(s) |
| HATU | N-[(Dimethylamino)-1H-1,2,3-triazolo-[4,5-b]pyridin-1-ylmethylene]-N-methylmethanaminium hexafluorophosphate N-oxide |
| HCl | hydrogen chloride |
| HPLC | high performance liquid chromatography |
| H$_2$O | water |
| HOBT | 1-hydroxybenzotriazole |
| K$_2$CO$_3$ | potassium carbonate |
| KOH | potassium hydroxide |
| MgSO$_4$ | magnesium sulfate |
| MeOH | methanol |
| N$_2$ | nitrogen gas |
| NBS | n-bromosuccinimide |
| NaH | sodium hydride |
| Na$_2$CO$_3$ | sodium carbonate |
| Na$_2$SO$_4$ | sodium sulfate |
| NaOMe | sodium methoxide |
| NaOH | sodium hydroxide |
| Na$_2$SO$_3$ | sodium sulfite |
| NH$_4$Cl | ammonium chloride |
| NH$_4$OH | ammonium hydroxide |
| n-BuLi | n-butyllithium |
| PPh$_3$ | triphenylphosphine |
| SEM-Cl | 2-(trimethylsilyl) ethoxymethyl chloride |
| TBAF | tetra-n-butylammonium fluoride |
| TEA | triethylamine |
| THF | tetrahydrofuran |

PREPARATION OF EXAMPLES AND INTERMEDIATES GENERAL PROCEDURE FOR THE PREPARATION OF INTERMEDIATES

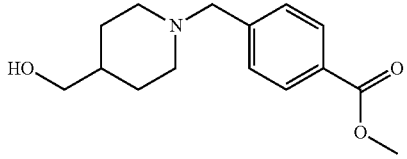 [SMILES: COC(=O)c1ccc(CN2CCC(CO)CC2)cc1]

methyl 4-((4-(hydroxymethyl)piperidin-1-yl)methyl) benzoate

To a solution of piperidin-4-ylmethanol (0.200 g, 1.73 mmol) and methyl-4-(bromomethyl)benzoate (0.396 g, 1.73 mmol) in MeCN (4 mL) was added K$_2$CO$_3$ (0.357 g, 2.59 mmol) and the reaction was stirred at room temperature. After 3 h, the reaction mixture was diluted with water and extracted with EtOAc. The combined organics layer was washed with water, brine, dried over Na$_2$SO$_4$, filtered, and concentrated. The crude residue was purified via silica gel chromatography to afford methyl 4-((4-(hydroxymethyl)piperidin-1-yl)methyl)benzoate (0.27 g). LCMS m/z 264 [M+H]$^+$.

The compounds in the following table were prepared according to the above procedures using the appropriate starting materials and modifications.

| Name | Structure | m/z |
|---|---|---|
| (1-(4-(methylsulfonyl)benzyl)piperidin-4-yl)methanol | 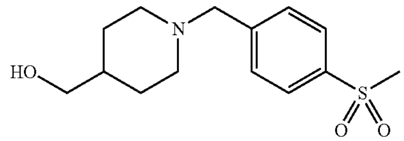 [SMILES: CS(=O)(=O)c1ccc(CN2CCC(CO)CC2)cc1] | 284 |

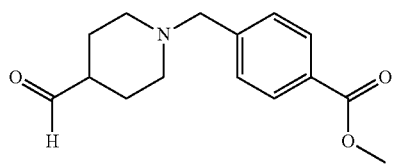 [SMILES: COC(=O)c1ccc(CN2CCC(C=O)CC2)cc1]

methyl 4-((4-formylpiperidin-1-yl)methyl)benzoate

To a solution of oxalyl chloride (0.045 mL, 0.539 mmol) and DCM (3 mL) at −78 C was added DMSO (0.056 mL, 0.795 mmol). The solution was stirred for 10 min, before dropwise addition of a solution of methyl 4-((4-(hydroxymethyl)piperidin-1-yl)methyl)benzoate (0.075 g, 0.284 mmol) in DCM (2 mL). After 15 min triethylamine (0.236 mL, 1.70 mmol) was added and the mixture was allowed to warm to room temperature. The reaction mixture was diluted with water and extracted with EtOAc. The combined organics layer was washed with water, brine, dried over $Na_2SO_4$, filtered, and concentrated. The crude residue was purified via silica gel chromatography to afford methyl 4-((4-formylpiperidin-1-yl)methyl)benzoate (53 mg). LCMS m/z 262 $[M+H]^+$.

The compounds in the following table were prepared according to the above procedure using the appropriate starting materials and modifications:

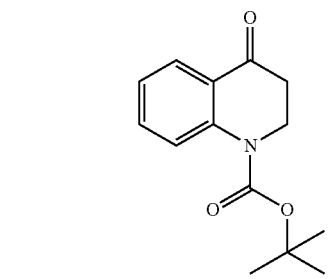

tert-butyl 4-oxo-3,4-dihydroquinoline-1(2H)-carboxylate

To a 50 mL round bottom flask charged with tert-butyl 3,4-dihydroquinoline-1(2H)-carboxylate (1 g, 4.28 mmol), dirhodium tetracaprolactamate (140 mg, 0.21 mmol) and sodium bicarbonate (179 mg, 2.14 mmol) was added anhydrous DCE (16 mL). tert-butyl hydrogen peroxide (4.28 mL, 21.4 mmol) was added and the reaction placed on a preheated hot plate (40° C.), fitted with a septum and an empty balloon and mixed for 12 h. The following day more catalyst and tert-butyl hydrogen peroxide were added (0.005 and 5 equiv, respectively) and the reaction was allowed to mix for an additional 4 h. The reaction was cooled to ambient temperature then filtered through a short plug of silica gel

| Name | Structure | m/z |
|---|---|---|
| tert-butyl 4-((4-formylpiperidin-1-yl)methyl)benzoate | 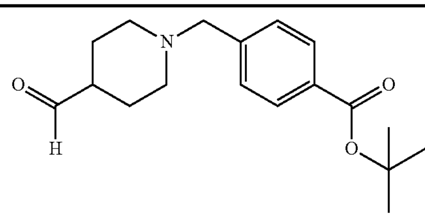 | |
| 1-(4-(methylsulfonyl)benzyl)piperidine-4-carbaldehyde | 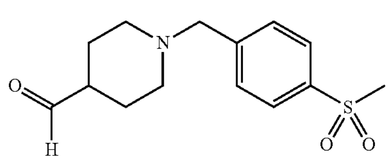 [SMILES: CS(=O)(=O)c1ccc(CN2CCC(C=O)CC2)cc1] | |
| tert-butyl 3-(4-formylpiperidin-1-yl)propanoate | | 242 | eluting with DCM (125 mL). The solution was concentrated and then purified by silica gel chromatography to afford tert-butyl 4-oxo-3,4-dihydroquinoline-1(2H)-carboxylate (785 mg, 75%) as a colorless oil. LCMS m/z 248 [M+H]+.

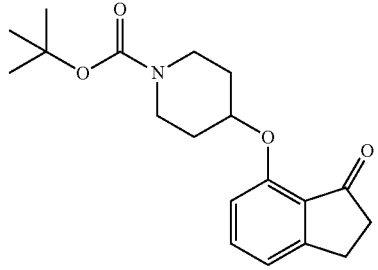 [SMILES: CC(C)(C)OC(=O)N1CCC(Oc2cccc3c2C(=O)CC3)CC1]

tert-butyl 4-((3-oxo-2,3-dihydro-1H-inden-4-yl)oxy) piperidine-1-carboxylate

To a round bottomed flask was added 7-hydroxy-2,3-dihydro-1H-inden-1-one (250 mg, 1.68 mmol), triphenylphosphine (571 mg, 2.18 mmol), tert-butyl 4-hydroxypiperidine-1-carboxylate (422 mg, 2.10 mmol), and THF. This solution was cooled to 0° C. before addition of DIAD (424 mg, 2.10 mmol). The solution was stirred overnight before concentrating. The crude residue was purified via silica gel chromatography to afford tert-butyl 4-((3-oxo-2,3-dihydro-1H-inden-4-yl)oxy)piperidine-1-carboxylate. LCMS m/z 332 [M+H]+.

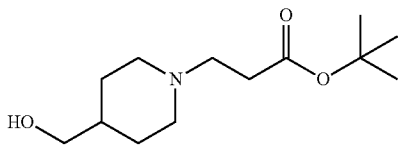 [SMILES: CC(C)(C)OC(=O)CCN1CCC(CO)CC1]

tert-butyl 3-(4-(hydroxymethyl)piperidin-1-yl)propanoate

Piperidin-4-ylmethanol (1.13 g, 9.81 mmol), tert-butyl acrylate (1.61 ml; 11.2 mmol) and N,N-diisopropylamine (3.4 mL, 19.6 mmol) were dissolved in MeOH (80 mL). The reaction mixture was heated to reflux overnight. After cooling to 25° C., the mixture was concentrated under reduced pressure. The crude residue was partitioned between EtOAc and 5% aqueous NaHCO3 solution. The organic layer was dried (Na2SO4), filtered, concentrated under reduced pressure, and purified by column chromatography (Silica, 10:90 MeOH:EtOAc). Pure fractions were evaporated to afford tert-butyl 3-(4-(hydroxymethyl)piperidin-1-yl)propanoate (1.95 g, 8.01 mmol) in 81% yield. LCMS m/z 244 [M+H]+.

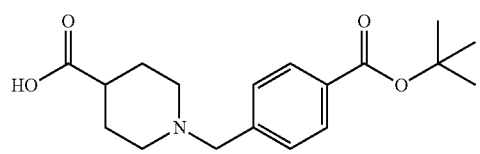 [SMILES: CC(C)(C)OC(=O)c1ccc(CN2CCC(C(=O)O)CC2)cc1]

1-(4-(tert-butoxycarbonyl)benzyl)piperidine-4-carboxylic acid

Step 1:

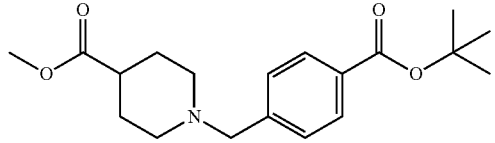 [SMILES: COC(=O)C1CCN(Cc2ccc(C(=O)OC(C)(C)C)cc2)CC1]

methyl 1-[(4-tert-butoxycarbonylphenyl)methyl] piperidine-4-carboxylate

The mixture of methyl piperidine-4-carboxylate (690 mg, 4.82 mmol, 1.0 eq), tert-butyl 4-(chloromethyl)benzoate (1.09 g, 4.82 mmol, 1.0 eq) and K2CO3 (1.33 g, 9.64 mmol, 2.0 eq) in DMF (10 mL) was stirred at 80° C. for 16 h. To the mixture was added ethyl acetate (20 mL). The mixture was washed with water (15 mL*3). The organic phase was concentrated in vacuo. The residue was purified by silica gel chromatography (petroleum ether: ethyl acetate=30:1 to 10:1) to afford methyl 1-[(4-tert-butoxycarbonylphenyl)methyl]piperidine-4-carboxylate (1.50 g, 4.50 mmol, 93% yield) as a yellow oil. LCMS m/z 334 [M+H]+.

Step 2:

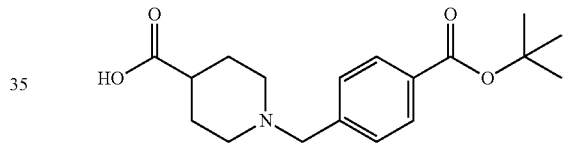

1-(4-(tert-butoxycarbonyl)benzyl)piperidine-4-carboxylic acid

The mixture of methyl 1-(4-(tert-butoxycarbonyl)benzyl) piperidine-4-carboxylate (400 mg, 1.2 mmol, 1.0 eq) and K2CO3 (829 mg, 6.0 mmol, 5.0 eq) in MeOH (10 mL) and H2O (2 mL) was stirred at 50° C. for 2 h. The mixture was concentrated in vacuo. The residue was dissolved in water (5 mL) and adjusted to pH 5 with aqueous HCl (1N). The solution was extracted with ethyl acetate and methanol (20:1, 15 mL*5). The combined organic phase was concentrated in vacuo to afford 1-(4-(tert-butoxycarbonyl)benzyl) piperidine-4-carboxylic acid (300 mg, 0.939 mmol, 78% yield) as a white solid. LCMS m/z 320 [M+H]+.

Tosyl Hydrazone Formation/3+2 Cycloaddition

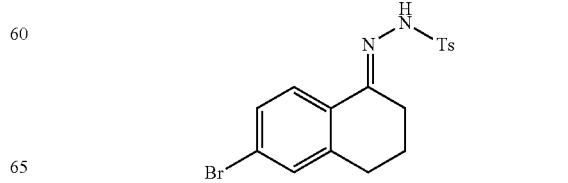

N'-(6-bromo-3,4-dihydronaphthalen-1(2H)-ylidene)-4-methylbenzenesulfonohydrazide A mixture of 6-bromo-3,4-dihydronaphthalen-1(2H)-one (1.00 g, 4.44 mmol) and 4-methylbenzenesulfonohydrazide (0.826 g, 4.44 mmol) in MeOH (8 mL) was heated to 60° C. for 2 h. A white solid was formed and after cooling to room temperature the solid was collected via filtration and washed with hexane. The filtrate was purified via silica gel chromatography and combined with the collected solid to afford N'-(6-bromo-3,4-dihydronaphthalen-1(2H)-ylidene)-4-methylbenzenesulfonohydrazide (1 g, 2.54 mmol). LCMS m/z 393 [M+H]$^+$.

methyl 6'-bromo-3',4'-dihydro-2'H-spiro[cyclopropane-1,1'-naphthalene]-2-carboxylate To a mixture of N'-(6-bromo-3,4-dihydronaphthalen-1(2H)-ylidene)-4-methylbenzenesulfonohydrazide (1.00 g, 2.54 mmol) and methyl acrylate (0.656 g, 7.62 mmol) in dioxane (10 mL) was added potassium carbonate (0.526 g, 3.81 mmol). The solution was heated to 110° C. for 18 h before cooling to room temperature, diluting with water, and extracting with EtOAc. The combined organics phase was washed with water, brine, dried over Na$_2$SO$_4$, and concentrated. The crude residue was purified via Silica gel chromatography to afford methyl 6'-bromo-3',4'-dihydro-2'H-spiro[cyclopropane-1,1'-naphthalene]-2-carboxylate (0.250 g)

The compounds in the following table were prepared according to the above procedures using the appropriate acrylate (methy acrylate, tert-butyl acrylate, methyl methacrylate) and tosyl hydrazone starting materials.

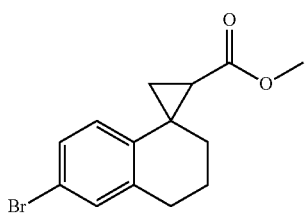 [SMILES: COC(=O)C1CC12CCCc1cc(Br)ccc12]

| Name | Structure | m/z |
|---|---|---|
| methyl 5'-bromo-2',3'-dihydrospiro[cyclopropane-1,1'-indene]-2-carboxylate | 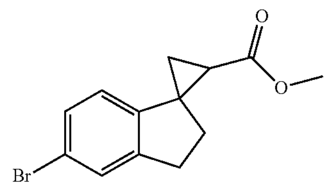 [SMILES: COC(=O)C1CC12CCc1cc(Br)ccc12] | 281/283 |
| methyl 6'-methoxy-3',4'-dihydro-2'H-spiro[cyclopropane-1,1'-naphthalene]-2-carboxylate | 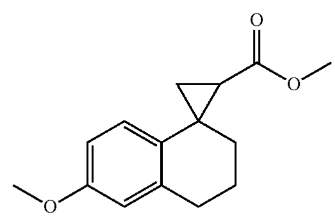 | 247 |
| 1'-(tert-butyl) 2-methyl 2',3'-dihydro-1'H-spiro[cyclopropane-1,4'-quinoline]-1',2-dicarboxylate | 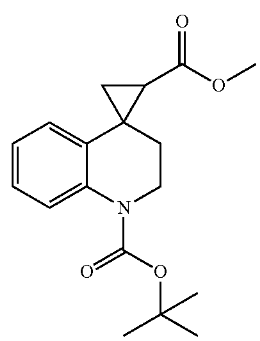 [SMILES: COC(=O)C1CC12CCN(C(=O)OC(C)(C)C)c1ccccc12] | 340 |
| tert-butyl 6'-cyano-3',4'-dihydro-2'H-spiro[cyclopropane-1,1'-naphthalene]-2-carboxylate | 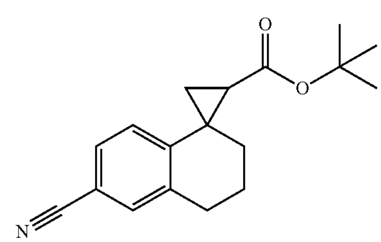 [SMILES: CC(C)(C)OC(=O)C1CC12CCCc1cc(C#N)ccc12] | 284 |

| Name | Structure | m/z |
|---|---|---|
| methyl 6,7,8,9-tetrahydrospiro[benzo[7]annulene-5,1'-cyclopropane]-2'-carboxylate | 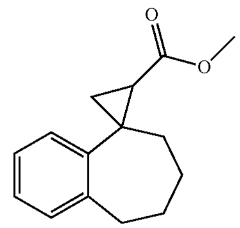 [SMILES: COC(=O)C1CC12CCCCc1ccccc12] | 231 |
| tert-butyl 6'-chloro-2',3'-dihydrospiro[cyclopropane-1,1'-indene]-2-carboxylate | 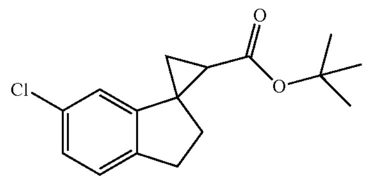 [SMILES: CC(C)(C)OC(=O)C1CC12CCc1ccc(Cl)cc12] | 223 [M − tBu + H]+ |
| methyl 4'-chloro-2',3'-dihydrospiro[cyclopropane-1,1'-indene]-2-carboxylate | 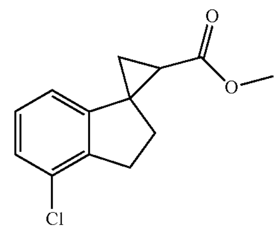 [SMILES: COC(=O)C1CC12CCc1c(Cl)cccc12] | |
| methyl 6'-bromo-2',3'-dihydrospiro[cyclopropane-1,1'-indene]-2-carboxylate | 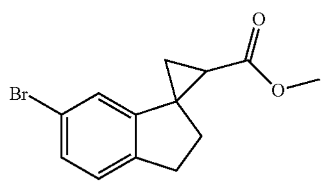 [SMILES: COC(=O)C1CC12CCc1ccc(Br)cc12] | |
| tert-butyl 4-((2-(methoxycarbonyl)-2',3'-dihydrospiro[cyclopropane-1,1'-inden]-7'-yl)oxy)piperidine-1-carboxylate | 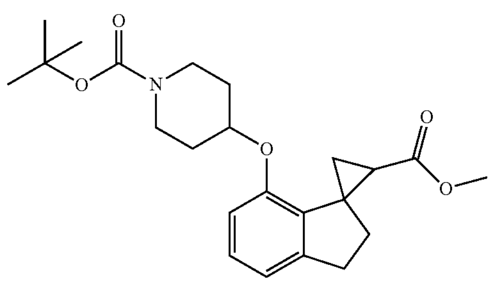 [SMILES: COC(=O)C1CC12CCc1cccc(OC3CCN(C(=O)OC(C)(C)C)CC3)c12] | 424 |
| tert-butyl 5',6'-dichloro-2',3'-dihydrospiro[cyclopropane-1,1'-indene]-2-carboxylate | 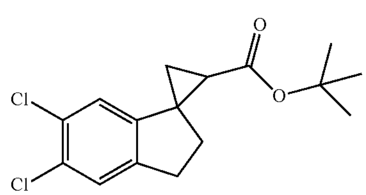 [SMILES: CC(C)(C)OC(=O)C1CC12CCc1cc(Cl)c(Cl)cc12] | 257 [M − tBu + H]+ |
| methyl 2-methyl-3',4'-dihydro-2'H-spiro[cyclopropane-1,1'-naphthalene]-2-carboxylate | 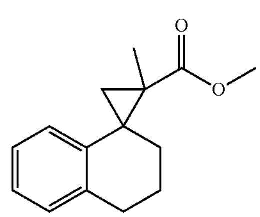 [SMILES: COC(=O)C1(C)CC12CCCc1ccccc12] | 231 |

| Name | Structure | m/z |
|---|---|---|
| tert-butyl 6'-fluoro-2',3'-dihydrospiro[cyclopropane-1,1'-indene]-2-carboxylate | 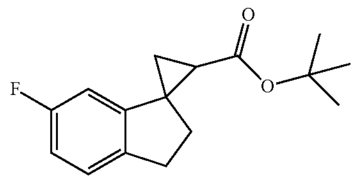 [SMILES: CC(C)(C)OC(=O)C1CC12CCc1ccc(F)cc12] | |
| tert-butyl 7'-chloro-3',4'-dihydro-2'H-spiro[cyclopropane-1,1'-naphthalene]-2-carboxylate | 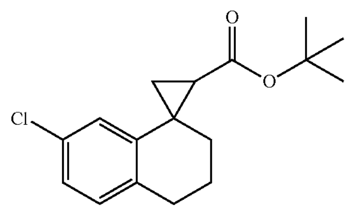 [SMILES: CC(C)(C)OC(=O)C1CC12CCCc1ccc(Cl)cc12] | 237 [M − tBu + H]+ |
| tert-butyl 6'-chloro-3',4'-dihydro-2'H-spiro[cyclopropane-1,1'-naphthalene]-2-carboxylate | 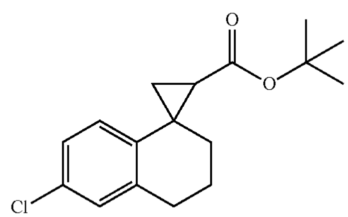 [SMILES: CC(C)(C)OC(=O)C1CC12CCCc1cc(Cl)ccc12] | 237 [M − tBu + H]+ |
| tert-butyl 7'-fluoro-3',4'-dihydro-2'H-spiro[cyclopropane-1,1'-naphthalene]-2-carboxylate | 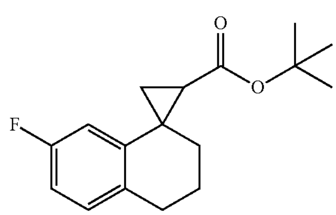 [SMILES: CC(C)(C)OC(=O)C1CC12CCCc1ccc(F)cc12] | 223 [M − tBu + H]+ |

C—O Bond Forming Reaction

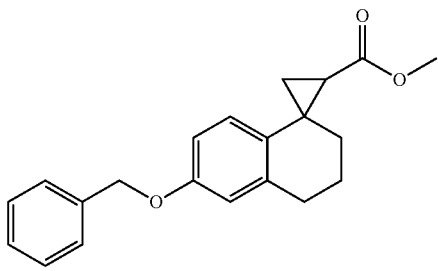 [SMILES: COC(=O)C1CC12CCCc1cc(OCc3ccccc3)ccc12]

methyl 6'-(benzyloxy)-3',4'-dihydro-2'H-spiro[cyclopropane-1,1'-naphthalene]-2-carboxylate To a resealable vial was added methyl 6'-bromo-3',4'-dihydro-2'H-spiro[cyclopropane-1,1'-naphthalene]-2-carboxylate (0.10 g, 0.34 mmol), phenylmethanol (0.057 g, 0.531 mmol), cesium carbonate (0.115 g, 0.354 mmol), and methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II) (tBuRockphos Precatalyst GIII) (0.015 g, 0.018 mmol). The vial was sealed and evacuated/backfilled with N$_2$ before addition of toluene (1 mL). The reaction mixture was heated to 90° C. for 3 h before cooling to room temperature. The reaction mixture was diluted with EtOAc and the solids removed via filtration. The filtrate was concentrated and the crude residue purified via silica gel chromatography to afford methyl 6'-(benzyloxy)-3',4'-dihydro-2'H-spiro[cyclopropane-1,1'-naphthalene]-2-carboxylate (80 mg). LCMS m/z 323 [M+H]+.

The compounds in the following table were prepared according to the above procedures using the appropriate starting materials and modifications

| Name | Structure | m/z |
|---|---|---|
| methyl 5'-(benzyloxy)-2',3'-dihydrospiro[cyclopropane-1,1'-indene]-2-carboxylate | 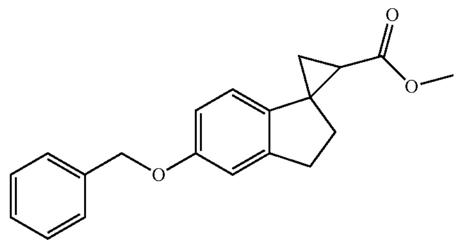 [SMILES: COC(=O)C1CC12CCc1cc(OCc3ccccc3)ccc12] | 309 |

Suzuki Reaction

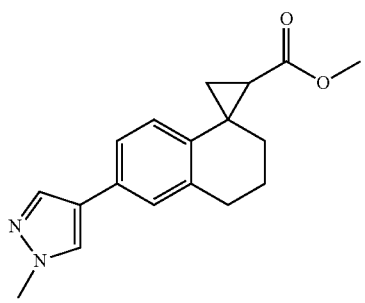 [SMILES: COC(=O)C1CC12CCCc1cc(-c3cnn(C)c3)ccc12]

methyl 6'-(1-methyl-1H-pyrazol-4-yl)-3',4'-dihydro-2'H-spiro[cyclopropane-1,1'-naphthalene]-2-carboxylate To a solution of methyl 6'-bromo-3',4'-dihydro-2'H-spiro[cyclopropane-1,1'-naphthalene]-2-carboxylate (0.200 g, 0.667 mmol) in dioxane (3 mL) were added 1-methyl-4-(4,4,5,5-tetramethyl-1,3,2-dioxaborolan-2-yl)-1H-pyrazole (0.168 g, 0.812 mmol), potassium carbonate (0.186 g, 1.35 mmol), chloro(2-dicyclohexylphosphino-2',6'-dimethoxy-1,1'-biphenyl)[2-(2-aminoethylphenyl)]palladium(II) methyl-t-butylether adduct (S-Phos precatalyst) (20 mg) and water (70 μL). The reaction mixture was purged with nitrogen and heated to 90° C. for 2 h. The mixture was cooled to room temperature and diluted with water. The reaction was extracted EtOAc and the combined organics layer was washed with water, brine, dried over Na₂SO₄, filtered, and concentrated. The crude residue was purified via silica gel chromatography to afford methyl 6'-(1-methyl-1H-pyrazol-4-yl)-3',4'-dihydro-2'H-spiro[cyclopropane-1,1'-naphthalene]-2-carboxylate (0.260 g). LCMS m/z 297 [M+H]⁺.

Methyl Ester Saponification

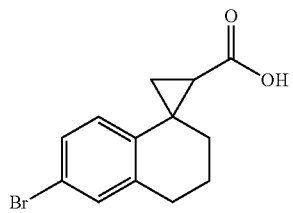

6'-bromo-3',4'-dihydro-2'H-spiro[cyclopropane-1,1'-naphthalene]-2-carboxylic acid To a round bottomed flask was added ethyl 6'-bromo-3',4'-dihydro-2'H-spiro[cyclopropane-1,1'-naphthalene]-2-carboxylate (6.28 g, 21.1 mmol), EtOH (50 mL), and sodium hydroxide (10.6 mL, 63.6 mmol). The solution was heated to 80° C. and stirred overnight. The solution was then cooled to room temperature and the volatiles removed. The remaining slurry was then taken up in water and the solution adjusted to pH=1 via addition of 6N HCl. This slurry was then extracted with EtOAc and the combined organics layer was washed with water, brine, dried over Na₂SO₄, filtered, and concentrated to afford 6'-bromo-3',4'-dihydro-2'H-spiro[cyclopropane-1,1'-naphthalene]-2-carboxylic acid (4.58 g, 16.2 mmol). LCMS m/z 281, 283 [M+H]⁺.

The compounds in the following table were prepared according to the above procedures using the appropriate starting materials and modifications.

| Name | Structure | m/z |
|---|---|---|
| 5'-(benzyloxy)-2',3'-dihydrospiro[cyclopropane-1,1'-indene]-2-carboxylic acid | 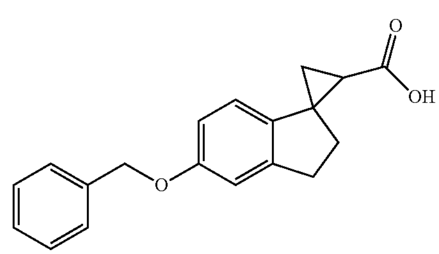 [SMILES: O=C(O)C1CC12CCc1cc(OCc3ccccc3)ccc12] | |

| Name | Structure | m/z |
|---|---|---|
| 6'-methoxy-3',4'-dihydro-2'H-spiro[cyclopropane-1,1'-naphthalene]-2-carboxylic acid | | 233 |
| 1'-(tert-butoxycarbonyl)-2',3'-dihydro-1'H-spiro[cyclopropane-1,4'-quinoline]-2-carboxylic acid | 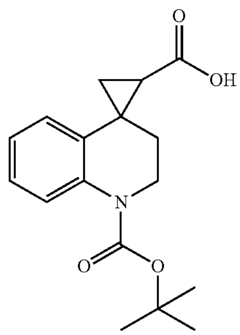 [SMILES: CC(C)(C)OC(=O)N1CCC2(CC2C(=O)O)c2ccccc21] | 326 |
| 6,7,8,9-tetrahydrospiro[benzo[7]annulene-5,1'-cyclopropane]-2'-carboxylic acid | 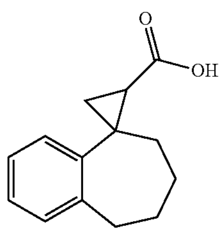 [SMILES: O=C(O)C1CC12CCCCc1ccccc12] | 217 |
| 4'-chloro-2',3'-dihydrospiro[cyclopropane-1,1'-indene]-2-carboxylic acid | 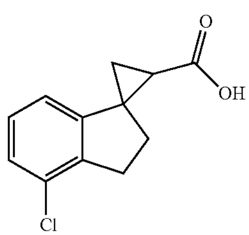 [SMILES: O=C(O)C1CC12CCc1c(Cl)cccc12] | |
| 6'-bromo-2',3'-dihydrospiro[cyclopropane-1,1'-indene]-2-carboxylic acid | 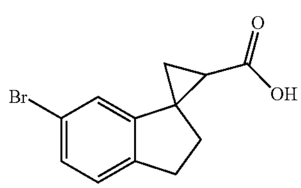 [SMILES: O=C(O)C1CC12CCc1ccc(Br)cc12] | |
| 7'-((1-(tert-butoxycarbonyl)piperidin-4-yl)oxy)-2',3'-dihydrospiro[cyclopropane-1,1'-indene]-2-carboxylic acid | 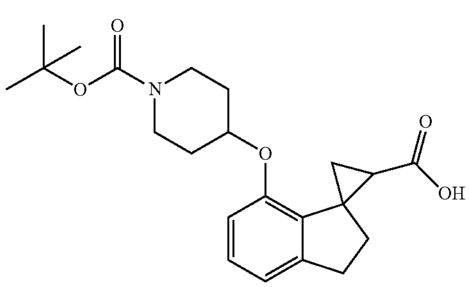 [SMILES: CC(C)(C)OC(=O)N1CCC(Oc2cccc3c2C2(CC3)CC2C(=O)O)CC1] | |

| Name | Structure | m/z |
|---|---|---|
| 2-methyl-3',4'-dihydro-2'H-spiro[cyclopropane-1,1'-naphthalene]-2-carboxylic acid | 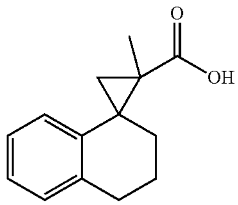 [SMILES: CC1(C(=O)O)CC12CCCc1ccccc12] | 217 |
| 6'-fluoro-2',3'-dihydrospiro[cyclopropane-1,1'-indene]-2-carboxylic acid | 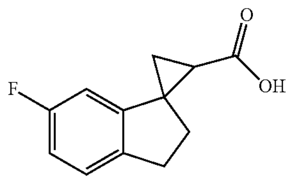 [SMILES: O=C(O)C1CC12CCc1ccc(F)cc12] | |
| 6'-(benzyloxy)-3',4'-dihydro-2'H-spiro[cyclopropane-1,1'-naphthalene]-2-carboxylic acid | 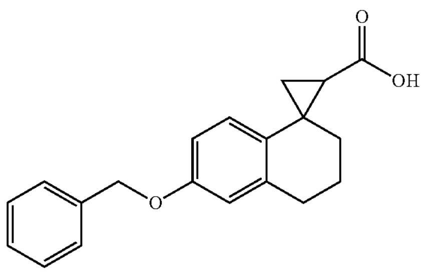 [SMILES: O=C(O)C1CC12CCCc1cc(OCc3ccccc3)ccc12] | 309 |
| 6'-(1-methyl-1H-pyrazol-4-yl)-3',4'-dihydro-2'H-spiro[cyclopropane-1,1-naphthalene]-2-carboxylic acid | | 283 | tBu-Ester Saponification

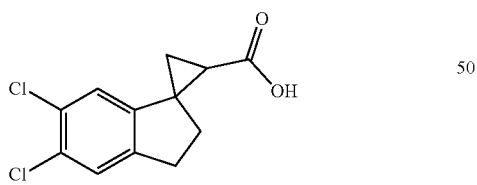

5',6'-dichloro-2',3'-dihydrospiro[cyclopropane-1,1'-indene]-2-carboxylic acid

To a solution of tert-butyl 5',6'-dichloro-2',3'-dihydrospiro[cyclopropane-1,1'-indene]-2-carboxylate (2.58 g, 8.23 mmol) in DCM (40 mL) was added 2,2,2-trifluoroacetic acid (12.4 mL, 164 mmol) at room temperature. The reaction was stirred overnight, then concentrated to dryness under vacuum. The desired product was purified by flash chromatography using a dichloromethane/methanol (100:0 to 95:5) mixture as eluent. The title compound was obtained as a solid (1.7 g; 81% yield). LCMS m/z 257 [M+H]+.

The compounds in the following table were prepared according to the above procedures using the appropriate starting materials and modifications.

| Name | Structure | m/z |
|---|---|---|
| 6'-cyano-3',4'-dihydro-2'H-spiro[cyclopropane-1,1'-naphthalene]-2-carboxylic acid | 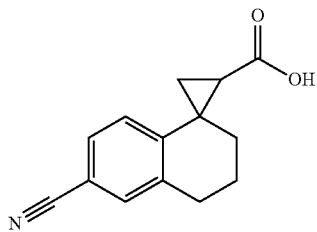 [SMILES: N#Cc1ccc2c(c1)CCCC21CC1C(=O)O] | 228 |

-continued

| Name | Structure | m/z |
|---|---|---|
| 6'-chloro-2',3'-dihydrospiro[cyclopropane-1,1'-indene]-2-carboxylic acid | 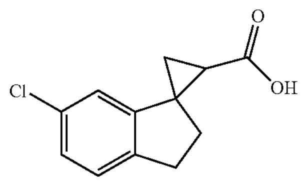 [SMILES: O=C(O)C1CC12CCc1ccc(Cl)cc12] | 223 |
| 6'-fluoro-2',3'-dihydrospiro[cyclopropane-1,1'-indene]-2-carboxylic acid | 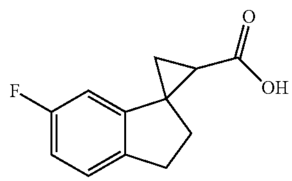 [SMILES: O=C(O)C1CC12CCc1ccc(F)cc12] | 207 |
| 7'-chloro-3',4'-dihydro-2'H-spiro[cyclopropane-1,1'-naphthalene]-2-carboxylic acid | 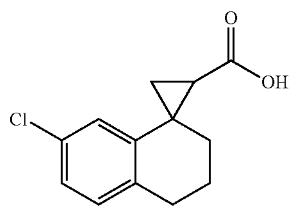 [SMILES: O=C(O)C1CC12CCCc1ccc(Cl)cc12] | 237 |
| 6'-chloro-3',4'-dihydro-2'H-spiro[cyclopropane-1,1'-naphthalene]-2-carboxylic acid | 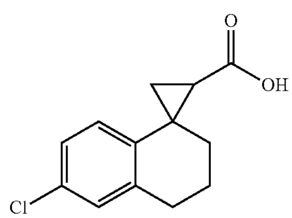 [SMILES: O=C(O)C1CC12CCCc1cc(Cl)ccc12] | 237 |
| 7'-fluoro-3',4'-dihydro-2'H-spiro[cyclopropane-1,1'-naphthalene]-2-carboxylic acid | 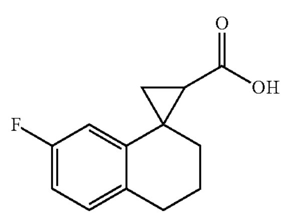 [SMILES: O=C(O)C1CC12CCCc1ccc(F)cc12] | 223 |

Example 1

Acyl Azide Formation/Curtius Rearrangement/Hydrolysis

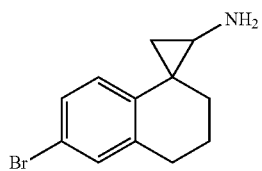

6'-bromo-3',4'-dihydro-2'H-spiro[cyclopropane-1,1'-naphthalen]-2-amine

To a round bottomed flask was added 6'-bromo-3',4'-dihydro-2'H-spiro[cyclopropane-1,1'-naphthalene]-2-carboxylic acid (0.899 g, 3.19 mmol), THF (10 mL), and triethylamine (1.11 mL, 7.97 mmol). The solution was cooled to 0° C. before addition of ethyl chloroformate (359 µL, 3.76 mmol). The solution was stirred for 30 min before addition of sodium azide (1.58 g, 24.3 mmol) in water (5 mL). The reaction was then warmed to room temperature and stirred for 15 min. The solution was diluted with water and extracted with EtOAc. The combined organics layer was washed with brine, dried over $Na_2SO_4$, filtered, and concentrated to afford crude 6'-bromo-3',4'-dihydro-2'H-spiro[cyclopropane-1,1'-naphthalene]-2-carbonyl azide. This material was used in the next step without further purification.

To a round bottomed flask was added crude 6'-bromo-3',4'-dihydro-2'H-spiro[cyclopropane-1,1'-naphthalene]-2-carbonyl azide and toluene (15 mL). This solution was heated to 90° C. for 24 h. The solution was then cooled to room temperature and potassium trimethylsilanolate (831 mg, 6.47 mmol) was added along with THF (3 mL). The solution was stirred at room temperature for 15 min before concentrating. The crude residue was taken up in MTBE and aq. HCl (1 N). The layers were separated and the organics layer was washed with HCl. The combined aqueous layers were basified with NaOH (1 N) to pH=14 and extracted with EtOAc. The combined organics layer dried over $Na_2SO_4$, filtered, and concentrated to afford 6'-bromo-3',4'-dihydro-2'H-spiro[cyclopropane-1,1'-naphthalen]-2-amine (576 mg, 2.28 mmol).

The examples in the following table were prepared according to the above procedures using the appropriate starting materials and modifications. The compounds were isolated as an unknown mixture of diastereomers.

| Example | Name | Structure | m/z |
|---|---|---|---|
| 2 | 5'-(benzyloxy)-2',3'-dihydrospiro[cyclopropane-1,1'-inden]-2-amine | 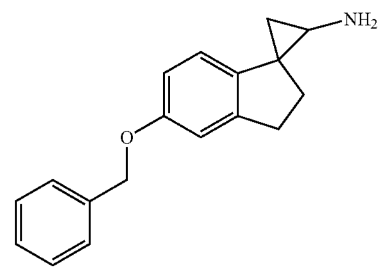 [SMILES: NC1CC12CCc1cc(OCc3ccccc3)ccc12] | 266 |

-continued

| Example | Name | Structure | m/z |
|---|---|---|---|
| 3 | 6'-methoxy-3',4'-dihydro-2'H-spiro[cyclopropane-1,1'-naphthalen]-2-amine | 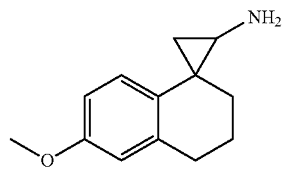 | 204 |
| 4 | tert-butyl 2-amino-2',3'-dihydro-1'H-spiro[cyclopropane-1,4'-quinoline]-1'-carboxylate | 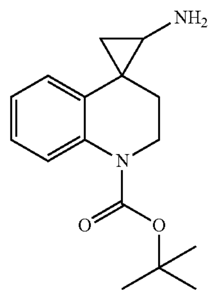 [SMILES: CC(C)(C)OC(=O)N1CCC2(CC2N)c2ccccc21] | 275 |
| 5 | 6,7,8,9-tetrahydrospiro[benzo[7]annulene-5,1'-cyclopropan]-2'-amine | 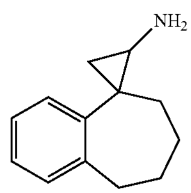 [SMILES: NC1CC12CCCCc1ccccc12] | 188 |
| 6 | 6'-(benzyloxy)-3',4'-dihydro-2'H-spiro[cyclopropane-1,1-naphthalen]-2-amine | 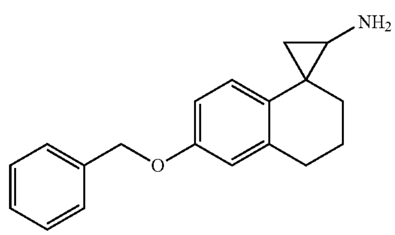 [SMILES: NC1CC12CCCc1cc(OCc3ccccc3)ccc12] | 280 |
| 7 | 6'-(1-methyl-1H-pyrazol-4-yl)-3',4'-dihydro-2'H-spiro[cyclopropane-1,1-naphthalen]-2-amine | 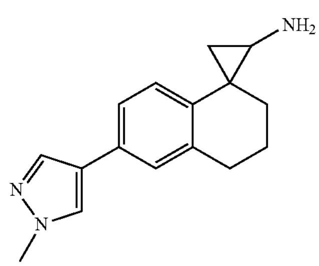 [SMILES: Cn1cc(-c2ccc3c(c2)CCCC32CC2N)cn1] | 254 |
| 8 | 6'-chloro-2',3'-dihydrospiro[cyclopropane-1,1'-inden]-2-amine | 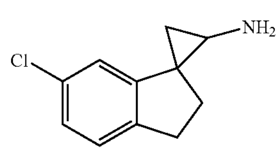 [SMILES: NC1CC12CCc1ccc(Cl)cc12] | 194 |
| 9 | 4'-chloro-2',3'-dihydrospiro[cyclopropane-1,1'-inden]-2-amine | 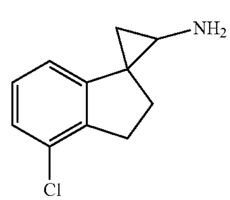 [SMILES: NC1CC12CCc1c(Cl)cccc12] | 194 |

-continued

| Example | Name | Structure | m/z |
|---|---|---|---|
| 10 | tert-butyl 4-((2-amino-2',3'-dihydrospiro[cyclopropane-1,1'-inden]-7'-yl)oxy)piperidine-1-carboxylate | 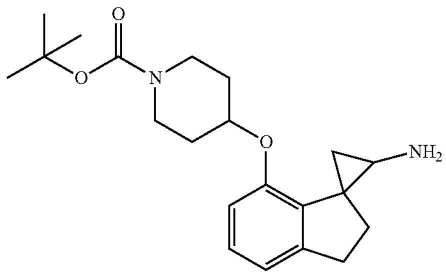 [SMILES: CC(C)(C)OC(=O)N1CCC(Oc2cccc3c2C2(CC3)CC2N)CC1] | 359 |
| 11 | 2-methyl-3',4'-dihydro-2'H-spiro[cyclopropane-1,1'-naphthalen]-2-amine | 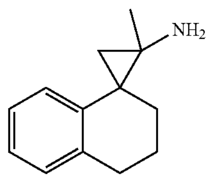 | 188 |
| 12 | 7'-chloro-3',4'-dihydro-2'H-spiro[cyclopropane-1,1'-naphthalen]-2-amine | 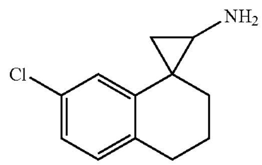 [SMILES: NC1CC12CCCc1ccc(Cl)cc12] | 208 |
| 13 | 6'-bromo-2',3'-dihydrospiro[cyclopropane-1,1'-inden]-2-amine | 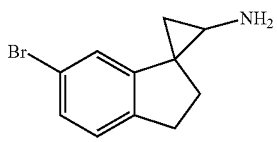 [SMILES: NC1CC12CCc1ccc(Br)cc12] | 238 |

The examples in the following table were prepared according to the above procedures using the appropriate starting materials and modifications. The examples in the following table were isolated as single diastereomers following silica gel chromatography or reverse phase HPLC purification.

| Example | Name | Structure | m/z |
|---|---|---|---|
| 15 | 2-amino-3',4'-dihydro-2'H-spiro[cyclopropane-1,1'-naphthalene]-6'-carbonitrile | Single diastereomer | 199 |
| 16 | 2-amino-3',4'-dihydro-2'H-spiro[cyclopropane-1,1'-naphthalene]-6'-carbonitrile | Single diastereomer | 199 |

Acyl Azide Formation/Curtius Rearrangement/Carbamate Formation

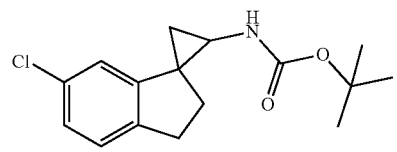 [SMILES: CC(C)(C)OC(=O)NC1CC12CCc1ccc(Cl)cc12]

tert-butyl (6'-chloro-2',3'-dihydrospiro[cyclopropane-1,1'-inden]-2-yl)carbamate 6'-chloro-2',3'-dihydrospiro[cyclopropane-1,1'-indene]-2-carboxylic acid (955 mg, 4.28 mmol) was dissolved in THF (21 mL), triethylamine (1.48 mL, 10.7 mmol) was added, and the solution was cooled to 0° C. The solution was mixed with ethyl chloroformate (580 mg, 5.35 mmol), and the reaction mixture was stirred at 0° C. for 1 h. Sodium azide (2.08 g, 32.0 mmol) dissolved in 4 ml of water is added and the reaction mixture is stirred at 0° C. for a further hour. The reaction mixture was diluted with water and extracted with EtOAc. The combined extracts were washed with brine, dried with $Na_2SO_4$ and evaporated under reduced pressure. The residue was taken up in benzene (3 mL) and the solution was heated to reflux for 2 hours. The solution was evaporated under reduced pressure to afford crude 6'-chloro-2-isocyanato-2',3'-dihydrospiro[cyclopropane-1,1'-indene] (940 mg, 4.27 mmol).

6'-chloro-2-isocyanato-2',3'-dihydrospiro[cyclopropane-1,1'-indene] (470 mg, 2.13 mmol) was dissolved in benzene (3 mL) and tert-butanol (4.2 g, 56.6 mmol) was added. The reaction mixture was heated at 90° C. for 12 hours. The reaction mixture was evaporated under reduced pressure and purified by column chromatography (25 g silica column, 5% to 40% EtOAc in hexanes) to afford tert-butyl (6'-chloro-2',3'-dihydrospiro[cyclopropane-1,1'-inden]-2-yl)carbamate (440 mg, 1.49 mmol), mix of diastereomers, racemic in 70% yield, over 2 steps. LCMS m/z 238/240 [M+H]$^+$.

The compounds in the following table were prepared according to the above procedures using the appropriate starting materials and modifications.

was partitioned between EtOAc and water. The organic layer was removed and the aqueous layer was extracted with EtOAc (2×). The combined organic extracts were washed with 1N HCl, water (2×), dried over $Na_2SO_4$, and concentrated to give white solids. The solids were subsequently triturated with hexanes to give tert-butyl (6'-bromo-2',3'-dihydrospiro[cyclopropane-1,1'-inden]-2-yl)carbamate (2.54 g, 7.50 mmol) as white solids. LCMS m/z 338 [M+H]$^+$.

The compounds in the following table were prepared according to the above procedures using the appropriate starting materials and modifications.

| Name | Structure | m/z |
|---|---|---|
| tert-butyl (6'-fluoro-2',3'-dihydrospiro[cyclopropane-1,1'-inden]-2-yl)carbamate | 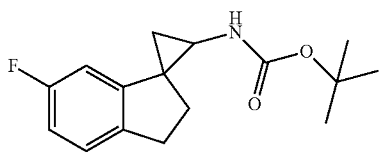 [SMILES: CC(C)(C)OC(=O)NC1CC12CCc1ccc(F)cc12] | 222 [M − tBu + H] |
| tert-butyl (7'-chloro-3',4'-dihydro-2'H-spiro[cyclopropane-1,1'-naphthalen]-2-yl)carbamate | 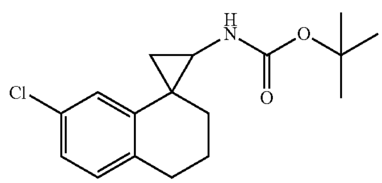 [SMILES: CC(C)(C)OC(=O)NC1CC12CCCc1ccc(Cl)cc12] | 330 [M + Na]$^+$ |
| tert-butyl (6'-chloro-3',4'-dihydro-2'H-spiro[cyclopropane-1,1'-naphthalen]-2-yl)carbamate | 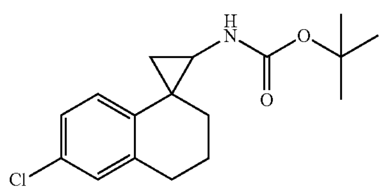 [SMILES: CC(C)(C)OC(=O)NC1CC12CCCc1cc(Cl)ccc12] | 252 |
| tert-butyl (7'-fluoro-3',4'-dihydro-2'H-spiro[cyclopropane-1,1'-naphthalen]-2-yl)carbamate | 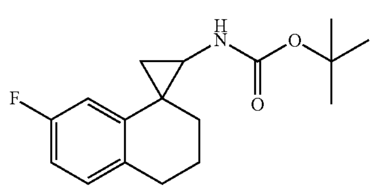 [SMILES: CC(C)(C)OC(=O)NC1CC12CCCc1ccc(F)cc12] | 236 |

Boc Protection

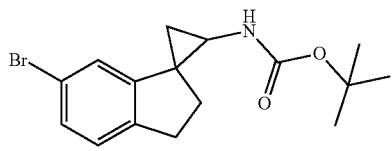 [SMILES: CC(C)(C)OC(=O)NC1CC12CCc1ccc(Br)cc12]

tert-butyl (6'-bromo-2',3'-dihydrospiro[cyclopropane-1,1'-inden]-2-yl)carbamate

To a solution of 6'-bromo-2',3'-dihydrospiro[cyclopropane-1,1'-inden]-2-amine (2.10 g, 8.81 mmol) in THF (10 mL) was added a solution of sodium carbonate (2.50 g, 23.5 mmol) in water (20 mL). To the bi-phasic mixture was added di-tert-butyl dicarbonate (2.46 g, 11.2 mmol). The mixture was stirred at room temperature for 6 h. The reaction mixture

| Name | Structure | m/z |
|---|---|---|
| tert-butyl (5'-bromo-2',3'-dihydrospiro[cyclopropane-1,1'-inden]-2-yl)carbamate | 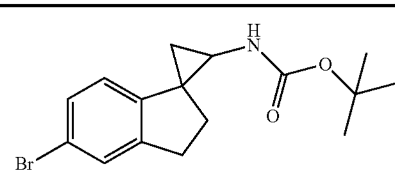 | |

Suzuki Reaction tert-butyl (6'-(pyridin-3-yl)-2',3'-dihydrospiro[cyclopropane-1,1'-inden]-2-yl)carbamate To a round bottomed flask charged with tert-butyl (6'-bromo-2',3'-dihydrospiro[cyclopropane-1,1'-inden]-2-yl)carbamate (0.10 g, 0.295 mmol), potassium carbonate (81 mg, 0.590 mmol), pyridine-3-yl boronic acid (43 mg, 0.353 mmol), and S-phos precatalyst (10 mg) was added dioxane (1.5 mL), and water (40 uL). The solution was heated to 90° C. for 2 h before cooling to room temperature and diluting with water. The solution was extracted with EtOAc and the combined organics were washed with brine, dried over Na$_2$SO$_4$, filtered, and concentrated. The crude residue was purified via silica gel chromatography to afford tert-butyl (6'-(pyridin-3-yl)-2',3'-dihydrospiro[cyclopropane-1,1'-inden]-2-yl)carbamate (90 mg).

The compounds in the following table were prepared according to the above procedures using the appropriate starting materials and modifications.

| Name | Structure | m/z |
|---|---|---|
| tert-butyl (6'-(1-(2-(methylsulfonyl)ethyl)-1H-pyrazol-4-yl)-2',3'-dihydrospiro[cyclopropane-1,1'-inden]-2-yl)carbamate | 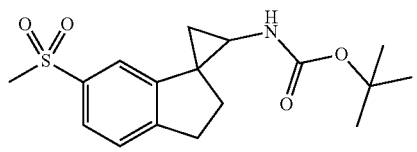 [SMILES: CC(C)(C)OC(=O)NC1CC12CCc1ccc(S(C)(=O)=O)cc12] | |

Sulfone Formation tert-butyl (6'-(methylsulfonyl)-2',3'-dihydrospiro[cyclopropane-1,1'-inden]-2-yl)carbamate A mixture of tert-butyl (6'-bromo-2',3'-dihydrospiro[cyclopropane-1,1'-inden]-2-yl)carbamate (0.050 g, 0.147 mmol), sodium methanesulfinate (0.018 g, 0.176 mmol), trifluorosulfonyloxy copper (I) (0.003 g, 0.047 mmol) and cyclohexanediamine (0.003 g, 0.029 mmol) in DMSO (2 mL) was purged with nitrogen and heated to 90° C. for 12 h. The solution was cooled to room temperature and the reaction mixture diluted with water and extracted with EtOAc. The combined organics phase was washed with water, brine, dried over Na$_2$SO$_4$, filtered, and concentrated. The crude residue was purified via silica gel chromatography to afford tert-butyl (6'-(methylsulfonyl)-2',3'-dihydrospiro[cyclopropane-1,1'-inden]-2-yl)carbamate (13 mg). LCMS m/z 360 [M+Na]$^+$.

Cyanation

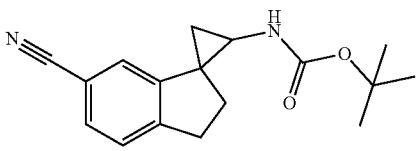 [SMILES: CC(C)(C)OC(=O)NC1CC12CCc1ccc(C#N)cc12]

tert-butyl (6'-cyano-2',3'-dihydrospiro[cyclopropane-1,1'-inden]-2-yl)carbamate To a mixture of tert-butyl (6'-bromo-2',3'-dihydrospiro[cyclopropane-1,1'-inden]-2-yl)carbamate (0.10 g, 0.29 mmol), Zn (0.003 g, 0.059 mmol), Zn(CN)$_2$ (0.019 g, 0.159 mmol) and [1,1'-binaphthalen]-2-yldi-tert-butylphosphine (0.012 g, 0.030 mmol) in DMF (1 mL) was added Pd(OAc)$_2$ (0.006 g, 0.030 mmol). The reaction was purged with nitrogen and heated to 110° C. for 2 h. The reaction mixture was cooled to room temperature, diluted with 2 M NH$_4$OH, and extracted with EtOAc. The combined organics layers were washed with brine, dried over Na$_2$SO$_4$, filtered, and concentrated. The crude residue was purified via silica gel chromatography to afford tert-butyl (6'-cyano-2',3'-dihydrospiro[cyclopropane-1,1'-inden]-2-yl)carbamate (0.065 g) as a white solid. LCMS m/z 285 [M+H]$^+$.

Carbonylation

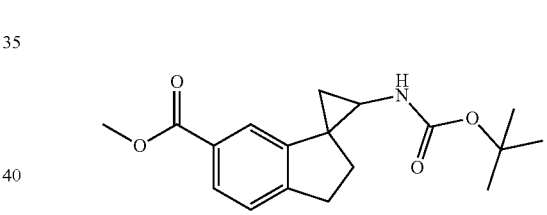

methyl 2-((tert-butoxycarbonyl)amino)-2',3'-dihydrospiro[cyclopropane-1,1'-indene]-6'-carboxylate To a vial charged with tert-butyl (6'-bromo-2',3'-dihydrospiro[cyclopropane-1,1'-inden]-2-yl)carbamate (0.20 g, 0.59 mmol), potassium carbonate (0.122 g, 0.886 mmol), Pd(OAc)$_2$ (0.003 g, 0.012 mmol), and 1,3-bis(dicyclohexylphosphonium)propane bis(tetrafluoroborate) (7 mg) was added MeOH (0.2 mL) and DMSO (1 mL). The mixture was purged with nitrogen and heated to 120° C. for 3 h under an atmosphere of carbon monoxide. The reaction mixture was diluted with water and extracted with EtOAc. The combined organics layer was washed with water, brine, dried over Na$_2$SO$_4$, filtered, and concentrated. The crude residue was purified via silica gel chromatography to afford methyl 2-((tert-butoxycarbonyl)amino)-2',3'-dihydrospiro[cyclopropane-1,1'-indene]-6'-carboxylate (160 mg).

The compounds in the following table were prepared according to the above procedures using the appropriate starting materials and modifications.

| Name | Structure | m/z |
|---|---|---|
| methyl 2-((tert-butoxycarbonyl)amino)-2',3'-dihydrospiro[cyclopropane-1,1'-indene]-5'-carboxylate | 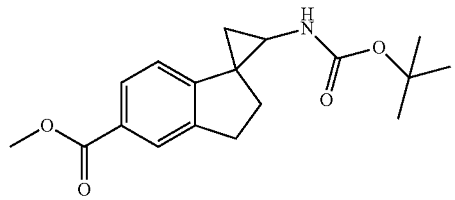 [SMILES: COC(=O)c1ccc2c(c1)CCC21CC1NC(=O)OC(C)(C)C] | |
| 2-((tert-butoxycarbonyl)amino)-3',4'-dihydro-2'H-spiro[cyclopropane-1,1'-naphthalene]-6'-carboxylic acid | 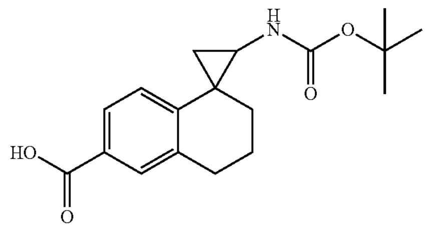 [SMILES: CC(C)(C)OC(=O)NC1CC12CCCc1cc(C(=O)O)ccc12] | 318 |

Saponification

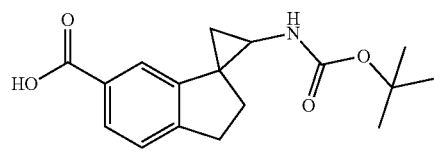 [SMILES: CC(C)(C)OC(=O)NC1CC12CCc1ccc(C(=O)O)cc12]

2-((tert-butoxycarbonyl)amino)-2',3'-dihydrospiro[cyclopropane-1,1'-indene]-6'-carboxylic acid To methyl 2-((tert-butoxycarbonyl)amino)-2',3'-dihydrospiro[cyclopropane-1,1'-indene]-6'-carboxylate (0.010 g, 0.032 mmol) dissolved in THF (1 mL) and MeOH (1 mL) was added NaOH (1 mL, 1 mmol). The solution was heated to 50° C. until complete conversion of the ester was observed. The reaction mixture was cooled to room temperature and acidified with HCl (1 N). The reaction was then extracted with EtOAc and the combined organics layers were washed with brine, dried over $Na_2SO_4$, filtered, and concentrated to afford 2-((tert-butoxycarbonyl)amino)-2',3'-dihydrospiro[cyclopropane-1,1'-indene]-6'-carboxylic acid (10 mg). LCMS m/z 248 [M-tBu+H]$^+$.

The compounds in the following table were prepared according to the above procedures using the appropriate starting materials and modifications.

| Name | Structure | m/z |
|---|---|---|
| 2-(((1-(tert-butoxycarbonyl)piperidin-4-yl)methyl)amino)-2',3'-dihydrospiro[cyclopropane-1,1'-indene]-6'-carboxylic acid | 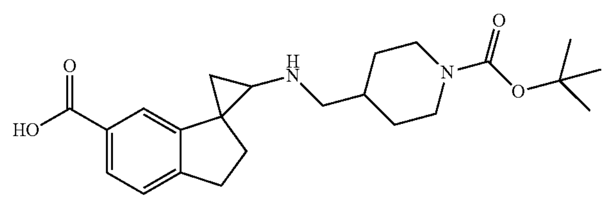 [SMILES: CC(C)(C)OC(=O)N1CCC(CNC2CC23CCc2ccc(C(=O)O)cc23)CC1] | 401 |
| 2-((tert-butoxycarbonyl)amino)-2',3'-dihydrospiro[cyclopropane-1,1'-indene]-5'-carboxylic acid | 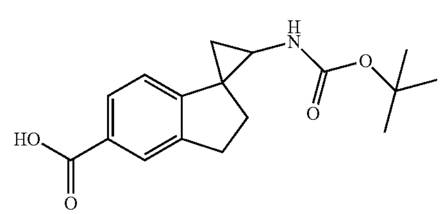 [SMILES: CC(C)(C)OC(=O)NC1CC12CCc1cc(C(=O)O)ccc12] | |

Amide Bond Formation

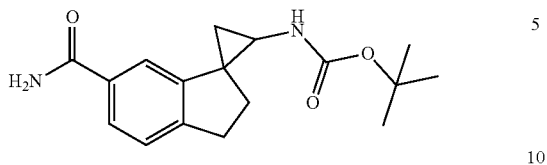

tert-butyl (6'-carbamoyl-2',3'-dihydrospiro[cyclopropane-1,1'-inden]-2-yl)carbamate To a solution of 2-((tert-butoxycarbonyl)amino)-2',3'-dihydrospiro[cyclopropane-1,1'-indene]-6'-carboxylic acid (0.082 g, 0.270 mmol) in THF (2 mL) was added CDI (0.048 g, 0.297 mmol). The reaction was stirred for 2 h at room temperature before addition of ammonium chloride (0.072 g, 1.35 mmol) and ammonium hydroxide (0.150 mL, 2.70 mmol). The reaction mixture was then diluted with water and extracted with EtOAc. The combined organics phase was washed with brine, dried over $Na_2SO_4$, filtered, and concentrated. The crude residue was purified via silica gel chromatography to afford tert-butyl (6'-carbamoyl-2',3'-dihydrospiro[cyclopropane-1,1'-inden]-2-yl)carbamate (61 mg). LCMS m/z 247 [M-tBu+H]$^+$.

The compounds in the following table were prepared according to the above procedures using the appropriate starting materials and modifications.

| Name | Structure | m/z |
|---|---|---|
| tert-butyl (5'-carbamoyl-2',3'-dihydrospiro[cyclopropane-1,1'-inden]-2-yl)carbamate | 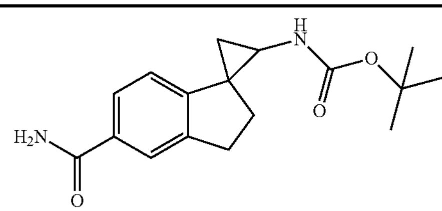 | |
| tert-butyl (5'-(pyrrolidine-1-carbonyl)-2',3'-dihydrospiro[cyclopropane-1,1'-inden]-2-yl)carbamate | 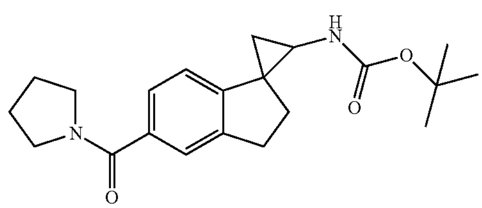 [SMILES: CC(C)(C)OC(=O)NC1CC12CCc1cc(C(=O)N3CCCC3)ccc12] | |

Example 17

Boc Deprotection

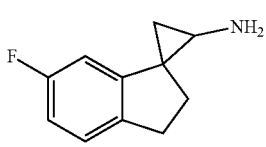 [SMILES: NC1CC12CCc1ccc(F)cc12]

To a solution of tert-butyl (6'-fluoro-2',3'-dihydrospiro[cyclopropane-1,1'-inden]-2-yl)carbamate (0.395 g, 1.42 mmol) in 1,4-dioxane (5 mL) was added a solution of HCl (1.77 mL, 7.1 mmol, 4 M) in 1,4-dioxane. The reaction mixture turned heterogeneous with precipitates after 24 h. After stirring for 24 h, the reaction mixture was concentrated in vacuo to afford 6'-fluoro-2',3'-dihydrospiro[cyclopropane-1,1'-inden]-2-amine hydrochloride (262 mg, 1.22 mmol) as yield light yellow solids. LCMS m/z 178 [M+H]$^+$.

The examples in the following table were prepared according to the above procedures using the appropriate starting materials and modifications.

| Example | Name | Structure | m/z |
|---|---|---|---|
| 18 | 6'-(pyridin-3-yl)-2',3'-dihydrospiro[cyclopropane-1,1'-inden]-2-amine | 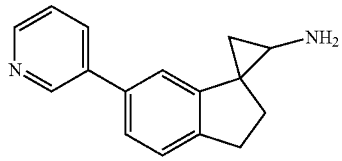 [SMILES: NC1CC12CCc1ccc(-c3cccnc3)cc12] | 237 |
| 19 | 6'-(methylsulfonyl)-2',3'-dihydrospiro[cyclopropane-1,1'-inden]-2-amine | 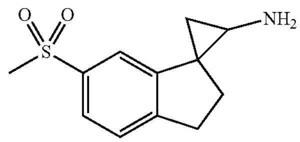 [SMILES: CS(=O)(=O)c1ccc2c(c1)C1(CC2)CC1N] | 238 |
| 20 | 2-amino-2',3'-dihydrospiro[cyclopropane-1,1'-indene]-6'-carbonitrile | 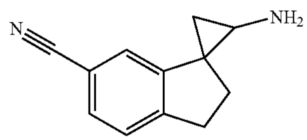 [SMILES: N#Cc1ccc2c(c1)C1(CC2)CC1N] | 185 |
| 21 | 6'-(1-(2-(methylsulfonyl)ethyl)-1H-pyrazol-4-yl)-2',3'-dihydrospiro[cyclopropane-1,1'-inden]-2-amine | 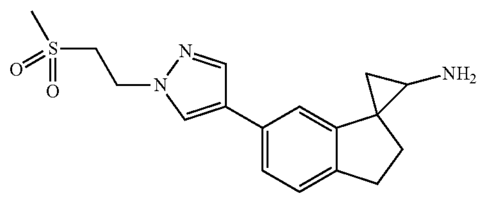 [SMILES: CS(=O)(=O)CCn1cc(-c2ccc3c(c2)C2(CC3)CC2N)cn1] | 332 |
| 22 | 2-amino-2',3'-dihydrospiro[cyclopropane-1,1'-indene]-6'-carboxylic acid | 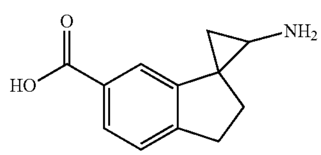 [SMILES: NC1CC12CCc1ccc(C(=O)O)cc12] | 204 |
| 23 | 7'-chloro-3',4'-dihydro-2'H-spiro[cyclopropane-1,1'-naphthalen]-2-amine | 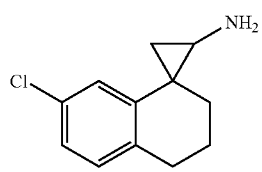 [SMILES: NC1CC12CCCc1ccc(Cl)cc12] | 208 |
| 24 | 6'-chloro-3',4'-dihydro-2'H-spiro[cyclopropane-1,1'-naphthalen]-2-amine | 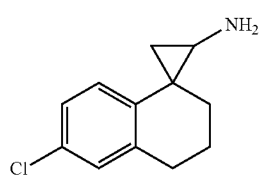 [SMILES: NC1CC12CCCc1cc(Cl)ccc12] | 208 |
| 25 | 2-amino-2',3'-dihydrospiro[cyclopropane-1,1'-indene]-6'-carboxamide | 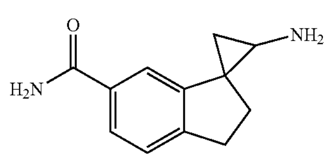 [SMILES: NC(=O)c1ccc2c(c1)C1(CC2)CC1N] | 203 |
| 26 | 2-amino-2',3'-dihydrospiro[cyclopropane-1,1'-indene]-5'-carboxamide | 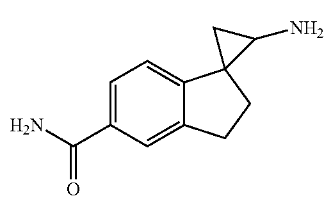 [SMILES: NC(=O)c1ccc2c(c1)CCC21CC1N] | 203 |

| Example | Name | Structure | m/z |
|---|---|---|---|
| 27 | (2-amino-2',3'-dihydrospiro[cyclopropane-1,1'-inden]-5'-yl)(pyrrolidin-1-yl)methanone | 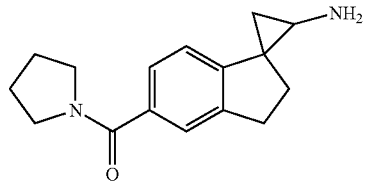 [SMILES: NC1CC12CCc1cc(C(=O)N3CCCC3)ccc12] | 257 |
| 28 | 2-amino-3',4'-dihydro-2'H-spiro[cyclopropane-1,1'-naphthalene]-6'-carboxylic acid | 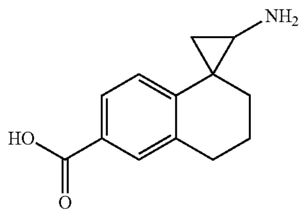 [SMILES: NC1CC12CCCc1cc(C(=O)O)ccc12] | 218 |

The examples in the following table were prepared according to the above procedures using the appropriate starting materials and modifications. The examples in the following table were isolated as single diastereomers following reverse phase HPLC purification.

| Example | Name | Structure | m/z | 1H NMR |
|---|---|---|---|---|
| 29 | 7'-fluoro-3',4'-dihydro-2'H-spiro[cyclopropane-1,1'-naphthalen]-2-amine | Single diastereomer | 192 | 1H NMR (400 MHz, DMSO-d6) δ 7.98 (br. s., 3H), 7.20 (dd, J = 6.35, 8.30 Hz, 1H), 7.02 (dt, J = 2.56, 8.48 Hz, 1H), 6.93 (dd, J = 2.69, 10.74 Hz, 1H), 2.72-2.94 (m, 2H), 2.57 (dd, J = 4.52, 7.93 Hz, 1H), 1.73-1.96 (m, 3H), 1.65 (dd, J = 4.39, 6.84 Hz, 1H), 1.16-1.31 (m, 2H) |
| 30 | 7'-fluoro-3',4'-dihydro-2'H-spiro[cyclopropane-1,1'-naphthalen]-2-amine | Single diastereomer | 192 | 1H NMR (400 MHz, DMSO-d6) d 8.37 (br. s., 3H), 7.04-7.21 (m, 1H), 6.82-6.99 (m, 1H), 6.61 (dd, J = 2.44, 11.23 Hz, 1H), 2.88 (dd, J = 5.13, 8.06 Hz, 1H), 2.68-2.83 (m, 2H), 1.66-1.95 (m, 4H), 1.45 (t, J = 7.20 Hz, 1H), 1.12 (t, J = 5.62 Hz, 1H) |

The compounds in the following table were prepared according to the above procedures using the appropriate starting materials and modifications.

| Name | Structure | m/z |
|---|---|---|
| methyl 2-amino-2',3'-dihydrospiro[cyclopropane-1,1'-indene]-6'-carboxylate | 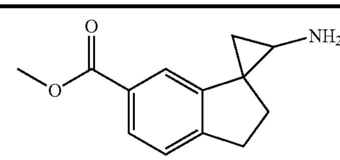 | 218 |

Example 31

Reductive Amination

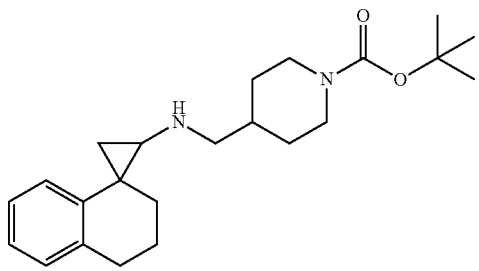 [SMILES: CC(C)(C)OC(=O)N1CCC(CNC2CC23CCCc2ccccc23)CC1]

tert-butyl 4-(((3',4'-dihydro-2'H-spiro[cyclopropane-1,1'-naphthalen]-2-yl)amino)methyl)piperidine-1-carboxylate To a solution of 3',4'-dihydro-2'H-spiro[cyclopropane-1,1'-naphthalen]-2-amine hydrochloride (0.050 g, 0.238 mmol) and tert-butyl 4-formylpiperidine-1-carboxylate (0.067 g, 0.285 mmol) in DCE (3 mL) was added NaBH(OAc)$_3$ (0.181 g, 0.856 mmol). After 30 min MeOH was added followed by EtOAc and potassium carbonate (1 M). The layers were separated and the aqueous phase was extracted with EtOAc. The combined organics phase was washed with water and brine, dried over Na$_2$SO$_4$, filtered, and concentrated. The crude residue was purified via silica gel chromatography to afford tert-butyl 4-(((3',4'-dihydro-2'H-spiro[cyclopropane-1,1'-naphthalen]-2-yl)amino)methyl)piperidine-1-carboxylate (73 mg). LCMS m/z 371 [M+H]$^+$.

The examples in the following table were prepared according to the above procedure using the appropriate starting materials and modifications. The compounds were isolated as unknown mixtures of diastereomers.

| Example | Name | Structure | m/z |
|---|---|---|---|
| 32 | methyl 4-((4-(((3',4'-dihydro-2'H-spiro[cyclopropane-1,1'-naphthalen]-2-yl)amino)methyl)piperidin-1-yl)methyl)benzoate | 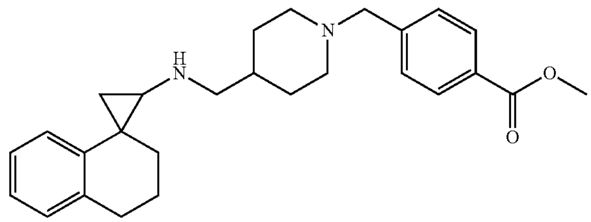 [SMILES: COC(=O)c1ccc(CN2CCC(CNC3CC34CCCc3ccccc34)CC2)cc1] | 419 |
| 33 | methyl 4-((4-(((2',3'-dihydrospiro[cyclopropane-1,1'-inden]-2-yl)amino)methyl)piperidin-1-yl)methyl)benzoate | 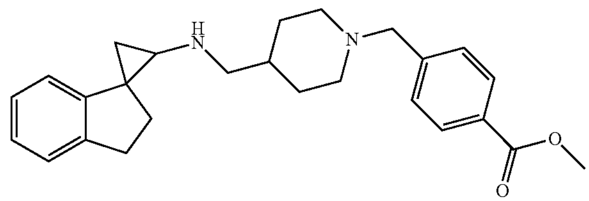 [SMILES: COC(=O)c1ccc(CN2CCC(CNC3CC34CCc3ccccc34)CC2)cc1] | 405 |
| 34 | tert-butyl 4-((4-(((3',4'-dihydro-2'H-spiro[cyclopropane-1,1'-naphthalen]-2-yl)amino)methyl)piperidin-1-yl)methyl)benzoate | 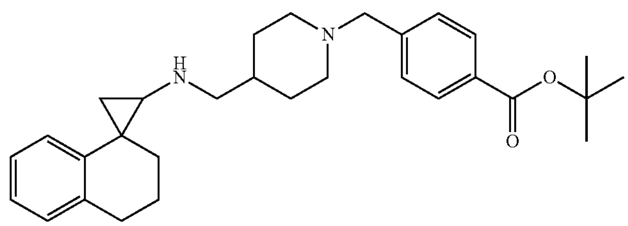 [SMILES: CC(C)(C)OC(=O)c1ccc(CN2CCC(CNC3CC34CCCc3ccccc34)CC2)cc1] | 461 |
| 35 | N-((tetrahydro-2H-pyran-4-yl)methyl)-3',4'-dihydro-2'H-spiro[cyclopropane-1,1'-naphthalen]-2-amine | 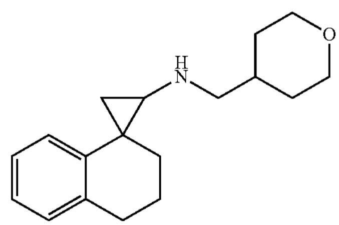 [SMILES: c1ccc2c(c1)CCCC21CC1NCC1CCOCC1] | 272 |
| 36 | tert-butyl 3-(((3',4'-dihydro-2'H-spiro[cyclopropane-1,1'-naphthalen]-2-yl)amino)methyl)piperidine-1-carboxylate | 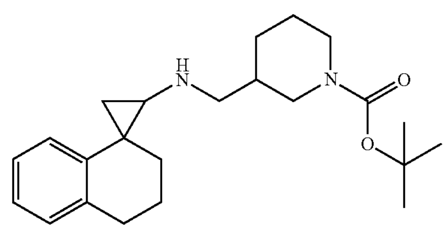 [SMILES: CC(C)(C)OC(=O)N1CCCC(CNC2CC23CCCc2ccccc23)C1] | 371 |
| 37 | tert-butyl 2-(((3',4'-dihydro-2'H-spiro[cyclopropane-1,1'-naphthalen]-2-yl)amino)methyl)piperidine-1-carboxylate | 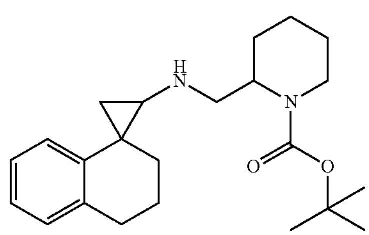 [SMILES: CC(C)(C)OC(=O)N1CCCCC1CNC1CC12CCCc1ccccc12] | 371 |
| 38 | N-((1-methyl-1H-pyrazol-3-yl)methyl)-2',3'-dihydrospiro[cyclopropane-1,1'-inden]-2-amine | 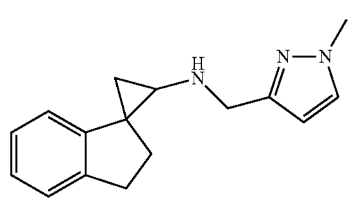 [SMILES: Cn1ccc(CNC2CC23CCc2ccccc23)n1] | 254 |

-continued

| Example | Name | Structure | m/z |
|---|---|---|---|
| 39 | N-(pyridin-3-ylmethyl)-3',4'-dihydro-2'H-spiro[cyclopropane-1,1'-naphthalen]-2-amine | 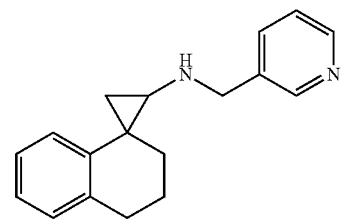 [SMILES: c1cncc(CNC2CC23CCCc2ccccc23)c1] | 265 |
| 40 | tert-butyl 4-(((6'-(pyridin-3-yl)-2',3'-dihydrospiro[cyclopropane-1,1'-inden]-2-yl)aimno)methyl)piperidine-1-carboxylate | 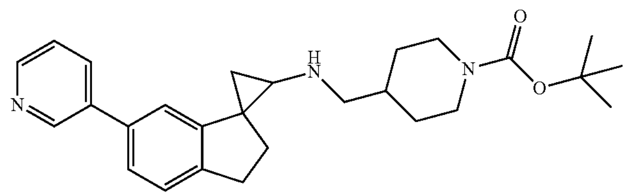 [SMILES: CC(C)(C)OC(=O)N1CCC(CNC2CC23CCc2ccc(-c4cccnc4)cc23)CC1] | 434 |
| 41 | tert-butyl ((1r,4r)-4-(((6'-(1-methyl-1H-pyrazol-4-yl)-2',3'-dihydrospiro[cyclopropane-1,1'-inden]-2-yl)amino)methyl)cyclohexyl)carbamate | 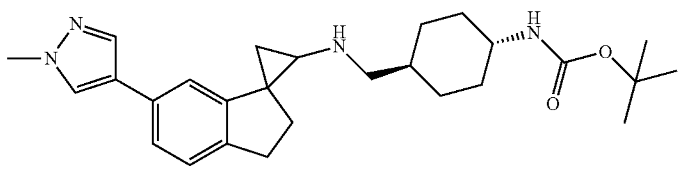 [SMILES: Cn1cc(-c2ccc3c(c2)C2(CC3)CC2NC[C@H]2CC[C@H](NC(=O)OC(C)(C)C)CC2)cn1] | 451 |
| 42 | N-((1-methylpiperidin-4-yl)methyl)-2',3'-dihydrospiro[cyclopropane-1,1'-inden]-2-amine | 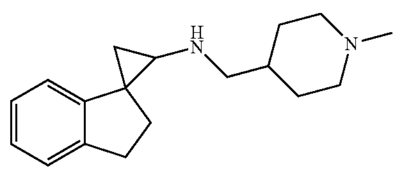 [SMILES: CN1CCC(CNC2CC23CCc2ccccc23)CC1] | 271 |
| 43 | 6'-(1-methyl-1H-pyrazol-4-yl)-N-((tetrahydro-2H-pyran-4-yl)methyl)-2',3'-dihydrospiro[cyclopropane-1,1'-inden]-2-amine | 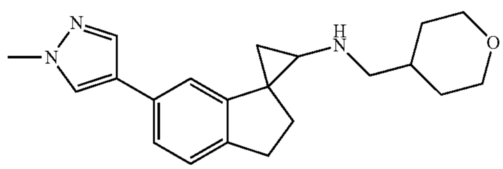 [SMILES: Cn1cc(-c2ccc3c(c2)C2(CC3)CC2NCC2CCOCC2)cn1] | 338 |
| 44 | N-(2',3'-dihydrospiro[cyclopropane-1,1'-inden]-2-yl)oxetan-3-amine | 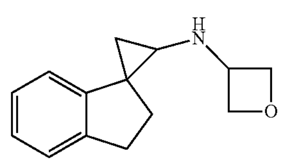 [SMILES: c1ccc2c(c1)CCC21CC1NC1COC1] | 216 |
| 45 | N-(3',4'-dihydro-2'H-spiro[cyclopropane-1,1'-naphthalen]-2-yl)oxetan-3-amine | 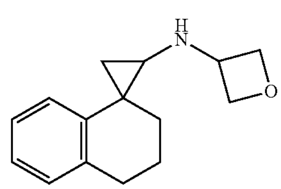 [SMILES: c1ccc2c(c1)CCCC21CC1NC1COC1] | 230 |
| 46 | N-((1-benzylpiperidin-4-yl)methyl)-2',3'-dihydrospiro[cyclopropane-1,1'-inden]-2-amine | 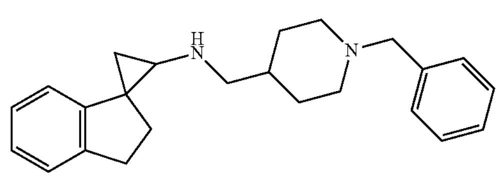 [SMILES: c1ccc(CN2CCC(CNC3CC34CCc3ccccc34)CC2)cc1] | 347 |

-continued

| Example | Name | Structure | m/z |
|---|---|---|---|
| 47 | N-((1-methyl-1H-pyrazol-4-yl)methyl)-2',3'-dihydrospiro[cyclopropane-1,1'-inden]-2-amine | 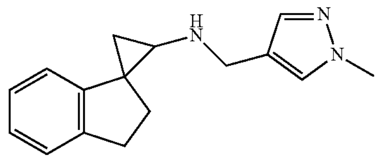 [SMILES: Cn1cc(CNC2CC23CCc2ccccc23)cn1] | 254 |
| 48 | 3-[(spiro[cyclopropane-2,1'-indane]-1-ylamino)methyl]pyridin-2-amine | 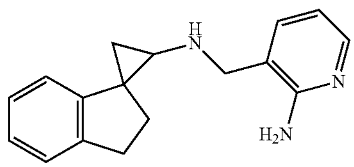 [SMILES: Nc1ncccc1CNC1CC12CCc1ccccc12] | 266 |
| 49 | N-(cyclopropylmethyl)-3',4'-dihydro-2'H-spiro[cyclopropane-1,1'-naphthalen]-2-amine | 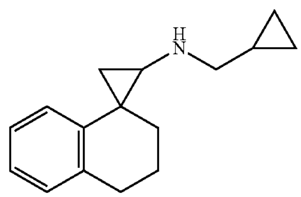 [SMILES: c1ccc2c(c1)CCCC21CC1NCC1CC1] | 228 |

The examples in the following table were prepared according to the above procedures using the appropriate starting materials and modifications. The examples in the following table were isolated as single diastereomers following reverse phase HPLC purification.

| Example | Name | Structure | m/z |
|---|---|---|---|
| 50 | N-((1-(4-(methylsulfonyl)benzyl)piperidin-4-yl)methyl)-2',3'-dihydrospiro[cyclopropane-1,1'-inden]-2-amine<br>single diastereomer | 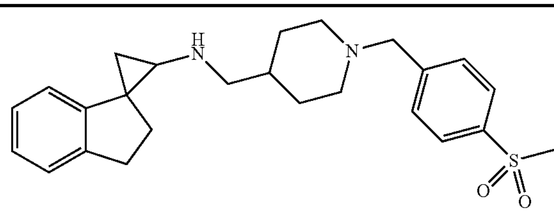 | 425 $^1$H NMR (400 MHz, DMSO-d6) δ 9.95 (br. s., 1H), 9.10 (br. s., 2H), 8.04 (d, J = 8.06 Hz, 2H), 7.77 (d, J = 8.30 Hz, 2H), 7.24 (d, J = 6.35 Hz, 1H), 7.09-7.20 (m, 2H), 6.75-6.84 (m, 1H), 4.42 (br. s., 2H), 3.42 (d, J = 11.72 Hz, 1H), 3.26 (s, 3H), 2.84-3.13 (m, 6H), 2.12-2.33 (m, 2H), 1.92-2.10 (m, 3H), 1.18-1.56 (m, 4H). |
| 51 | N-((1-(4-(methylsulfonyl)benzyl)piperidin-4-yl)methyl)-2',3'-dihydrospiro[cyclopropane-1,1'-inden]-2-amine<br>single diastereomer | 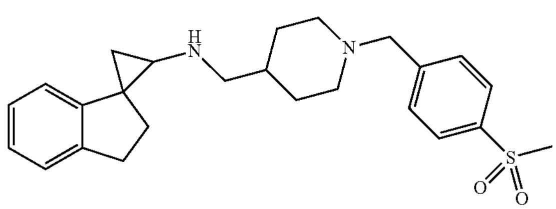 [SMILES: CS(=O)(=O)c1ccc(CN2CCC(CNC3CC34CCc3ccccc34)CC2)cc1] | 425 $^1$H NMR (400 MHz, DMSO-d6) δ 9.81 (br. s., 1H), 9.58 (br. s., 1H), 8.12 (br. s, 1H), 8.02 (d, J = 8.06 Hz, 2H), 7.73 (d, J = 8.30 Hz, 2H), 7.31 (d, J = 7.57 Hz, 2H), 7.09-7.27 (m, 2H), 4.36 (br. s., 2H), 3.28-3.35 (m, 1H), 3.26 (s, 3H), 2.73-3.14 (m, 5H), 2.06-2.28 (m, 2H), 1.91 (dd, J = 7.81, 12.45 Hz, 1H), 1.56-1.84 (m, 3H), 1.32-1.48 (m, 2H), 1.14-1.29 (m, 1H), 0.96-1.12 (m, 1H). |

The intermediates in the following table were prepared according to the above procedure using the appropriate starting materials and modifications:

| Name | Structure | m/z |
|---|---|---|
| tert-butyl 4-((3',4'-dihydro-2'H-spiro[cyclopropane-1,1'-naphthalen]-2-yl)amino)piperidine-1-carboxylate | | |
| tert-butyl (4-((3',4'-dihydro-2'H-spiro[cyclopropane-1,1'-naphthalen]-2-yl)amino)cyclohexyl)carbamate | 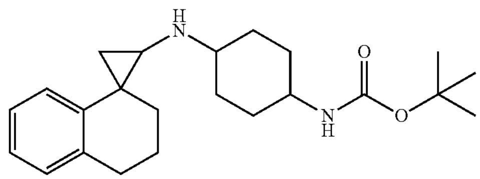 [SMILES: CC(C)(C)OC(=O)NC1CCC(NC2CC23CCCc2ccccc23)CC1] | 371 |
| tert-butyl 4-(2-((3',4'-dihydro-2'H-spiro[cyclopropane-1,1'-naphthalen]-2-yl)amino)ethyl)piperidine-1-carboxylate | 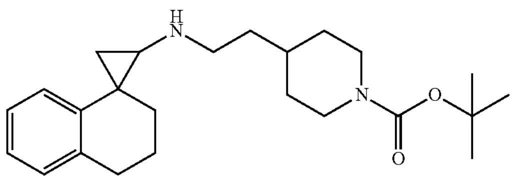 [SMILES: CC(C)(C)OC(=O)N1CCC(CCNC2CC23CCCc2ccccc23)CC1] | 385 |
| tert-butyl 4-(((5'-(benzyloxy)-2',3'-dihydrospiro[cyclopropane-1,1'-inden]-2-yl)amino)methyl)piperidine-1-carboxylate | 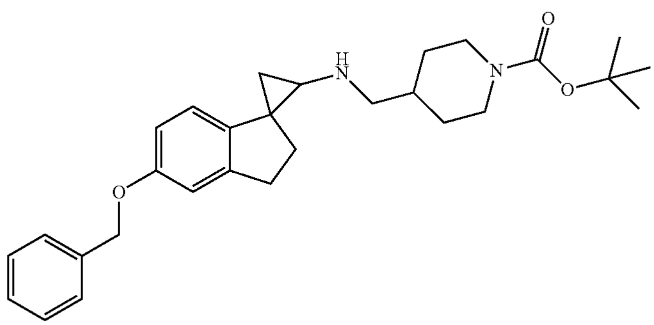 [SMILES: CC(C)(C)OC(=O)N1CCC(CNC2CC23CCc2cc(OCc4ccccc4)ccc23)CC1] | 485 [M + Na]+ |
| tert-butyl 4-(((6,7,8,9-tetrahydrospiro[benzo[7]annulene-5,1'-cyclopropan]-2'-yl)amino)methyl)piperidine-1-carboxylate | 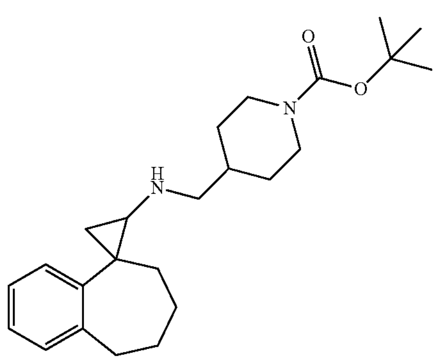 [SMILES: CC(C)(C)OC(=O)N1CCC(CNC2CC23CCCCc2ccccc23)CC1] | 385 |
| tert-butyl 4-(((6'-chloro-2',3'-dihydrospiro[cyclopropane-1,1'-inden]-2-yl)amino)methyl)piperidine-1-carboxylate | 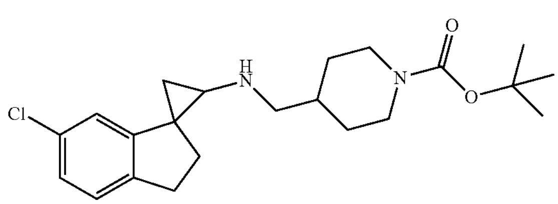 [SMILES: CC(C)(C)OC(=O)N1CCC(CNC2CC23CCc2ccc(Cl)cc23)CC1] | 335 |

-continued

| Name | Structure | m/z |
|---|---|---|
| tert-butyl ((3-((2',3'-dihydrospiro[cyclopropane-1,1'-inden]-2-yl)amino)cyclobutyl)methyl)carbamate | 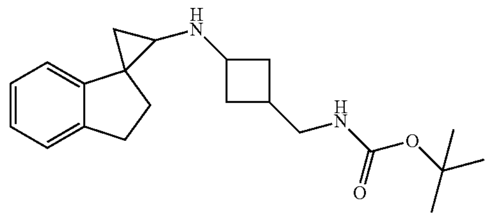 [SMILES: CC(C)(C)OC(=O)NCC1CC(NC2CC23CCc2ccccc23)C1] | |
| tert-butyl (4-((6'-chloro-2',3'-dihydrospiro[cyclopropane-1,1'-inden]-2-yl)amino)cyclohexyl)carbamate | 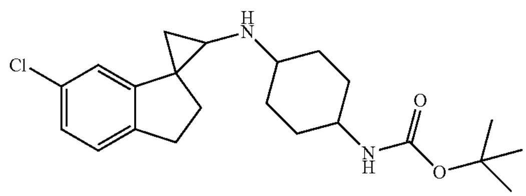 [SMILES: CC(C)(C)OC(=O)NC1CCC(NC2CC23CCc2ccc(Cl)cc23)CC1] | 391 |
| tert-butyl (4-((2',3'-dihydrospiro[cyclopropane-1,1'-inden]-2-yl)amino)cyclohexyl)carbamate | 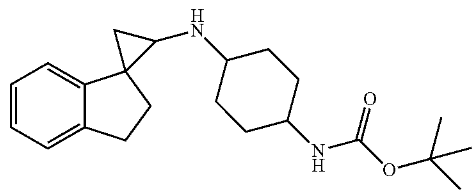 [SMILES: CC(C)(C)OC(=O)NC1CCC(NC2CC23CCc2ccccc23)CC1] | |
| tert-butyl ((3-((6'-chloro-2',3'-dihydrospiro[cyclopropane-1,1'-inden]-2-yl)amino)cyclobutyl)methyl)carbamate | 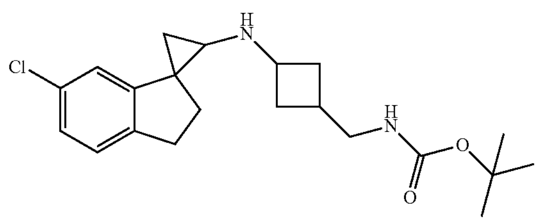 [SMILES: CC(C)(C)OC(=O)NCC1CC(NC2CC23CCc2ccc(Cl)cc23)C1] | |
| tert-butyl 3-(2-((6'-chloro-2',3'-dihydrospiro[cyclopropane-1,1'-inden]-2-yl)amino)ethyl)azetidine-1-carboxylate | 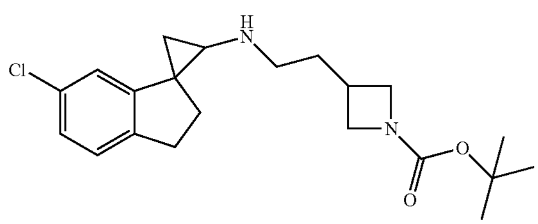 [SMILES: CC(C)(C)OC(=O)N1CC(CCNC2CC23CCc2ccc(Cl)cc23)C1] | |
| tert-butyl 4-((4-(((6'-(pyridin-3-yl)-2',3'-dihydrospiro[cyclopropane-1,1'-inden]-2-yl)amino)methyl)piperidin-1-yl)methyl)benzoate | 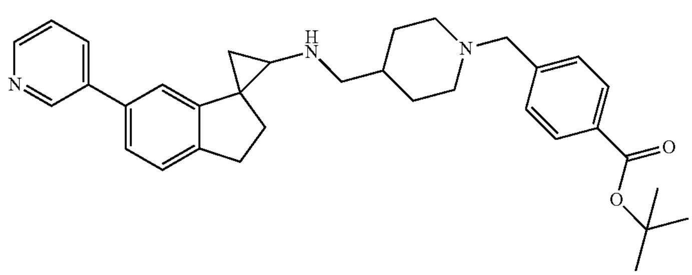 [SMILES: CC(C)(C)OC(=O)c1ccc(CN2CCC(CNC3CC34CCc3ccc(-c5cccnc5)cc34)CC2)cc1] | |
| tert-butyl 4-(((6'-fluoro-2',3'-dihydrospiro[cyclopropane-1,1'-inden]-2-yl)amino)methyl)piperidine-1-carboxylate | 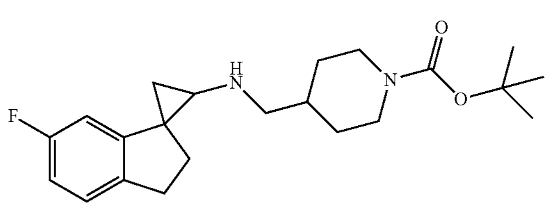 [SMILES: CC(C)(C)OC(=O)N1CCC(CNC2CC23CCc2ccc(F)cc23)CC1] | 319 [M − tBu + H]+ |

-continued

| Name | Structure | m/z |
|---|---|---|
| tert-butyl 6-((2',3'-dihydrospiro[cyclopropane-1,1'-inden]-2-yl)amino)-2-azaspiro[3.3]heptane-2-carboxylate | 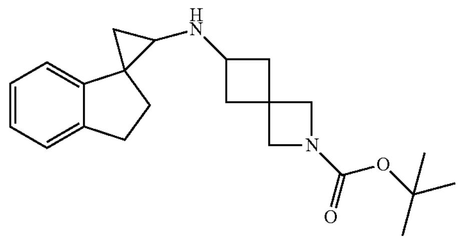 [SMILES: CC(C)(C)OC(=O)N1CC2(CC(NC3CC34CCc3ccccc34)C2)C1] | 355 |
| tert-butyl 4-(((7'-chloro-3',4'-dihydro-2'H-spiro[cyclopropane-1,1'-naphthalen]-2-yl)amino)methyl)piperidine-1-carboxylate | 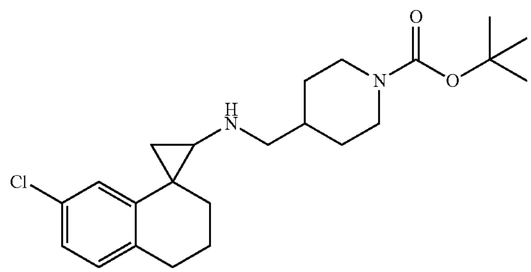 [SMILES: CC(C)(C)OC(=O)N1CCC(CNC2CC23CCCc2ccc(Cl)cc23)CC1] | 349 |
| tert-butyl 4-(((6'-cyano-2',3'-dihydrospiro[cyclopropane-1,1'-inden]-2-yl)amino)methyl)piperidine-1-carboxylate | 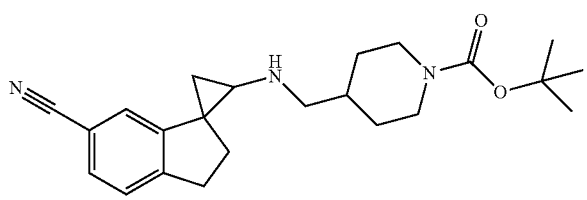 [SMILES: CC(C)(C)OC(=O)N1CCC(CNC2CC23CCc2ccc(C#N)cc23)CC1] | |
| tert-butyl 4-(((6'-methyl-2',3'-dihydrospiro[cyclopropane-1,1'-inden]-2-yl)amino)methyl)piperidine-1-carboxylate | 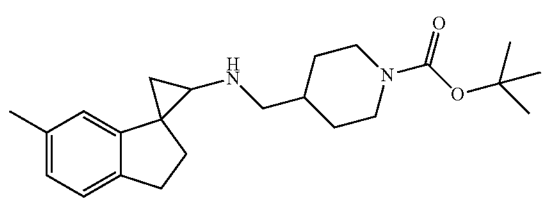 [SMILES: Cc1ccc2c(c1)C1(CC2)CC1NCC1CCN(C(=O)OC(C)(C)C)CC1] | 371 |
| tert-butyl 4-(((6'-(1-methyl-1H-pyrazol-4-yl)-2',3'-dihydrospiro[cyclopropane-1,1'-inden]-2-yl)amino)methyl)piperidine-1-carboxylate | 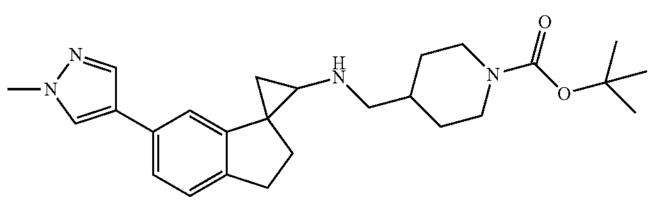 [SMILES: Cn1cc(-c2ccc3c(c2)C2(CC3)CC2NCC2CCN(C(=O)OC(C)(C)C)CC2)cn1] | 437 |
| tert-butyl 4-(((2',3'-dihydrospiro[cyclopropane-1,1'-inden]-2-yl)amino)methyl)piperidine-1-carboxylate | 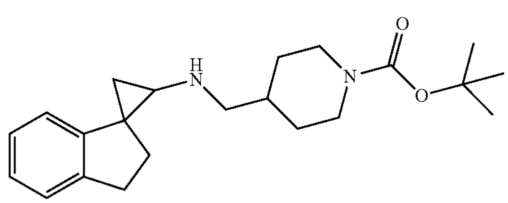 [SMILES: CC(C)(C)OC(=O)N1CCC(CNC2CC23CCc2ccccc23)CC1] | |
| tert-butyl 4-(((5'-chloro-2',3'-dihydrospiro[cyclopropane-1,1'-inden]-2-yl)amino)methyl)piperidine-1-carboxylate | 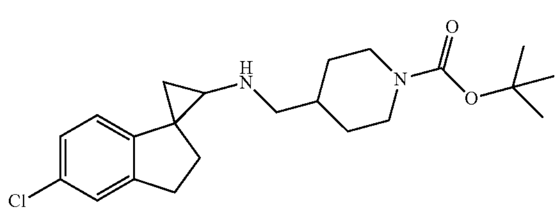 [SMILES: CC(C)(C)OC(=O)N1CCC(CNC2CC23CCc2cc(Cl)ccc23)CC1] | |

| Name | Structure | m/z |
|---|---|---|
| tert-butyl 4-(((4'-chloro-2',3'-dihydrospiro[cyclopropane-1,1'-inden]-2-yl)amino)methyl)piperidine-1-carboxylate | 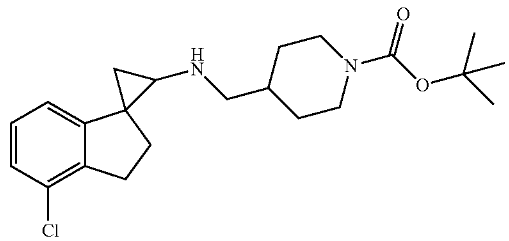 [SMILES: CC(C)(C)OC(=O)N1CCC(CNC2CC23CCc2c(Cl)cccc23)CC1] | |
| tert-butyl 4-(((6'-(methoxycarbonyl)-2',3'-dihydrospiro[cyclopropane-1,1'-inden]-2-yl)amino)methyl)piperidine-1-carboxylate | 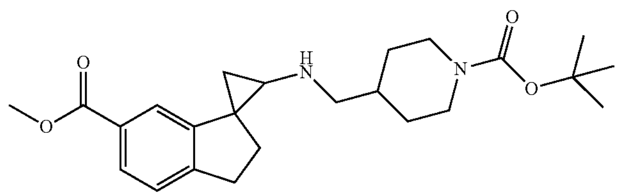 [SMILES: COC(=O)c1ccc2c(c1)C1(CC2)CC1NCC1CCN(C(=O)OC(C)(C)C)CC1] | 415 |
| tert-butyl 3-(4-(((2',3'-dihydrospiro[cyclopropane-1,1'-inden]-2-yl)amino)methyl)piperidin-1-yl)propanoate | 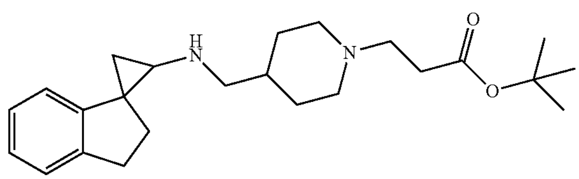 [SMILES: CC(C)(C)OC(=O)CCN1CCC(CNC2CC23CCc2ccccc23)CC1] | 385 |
| tert-butyl 4-(((6'-chloro-3',4'-dihydro-2'H-spiro[cyclopropane-1,1'-naphthalen]-2-yl)amino)methyl)piperidine-1-carboxylate | 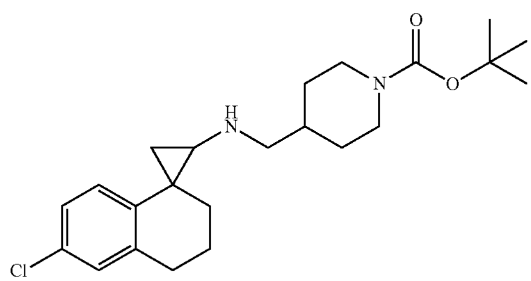 [SMILES: CC(C)(C)OC(=O)N1CCC(CNC2CC23CCCc2cc(Cl)ccc23)CC1] | 252 |
| tert-butyl 4-(((7'-fluoro-3',4'-dihydro-2'H-spiro[cyclopropane-1,1'-naphthalen]-2-yl)amino)methyl)piperidine-1-carboxylate | 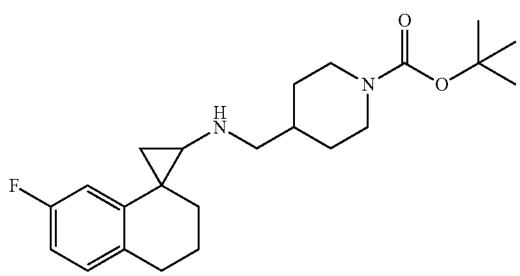 [SMILES: CC(C)(C)OC(=O)N1CCC(CNC2CC23CCCc2ccc(F)cc23)CC1] | 333 [M − tBu + H]+ |

Example 52

Boc Deprotection

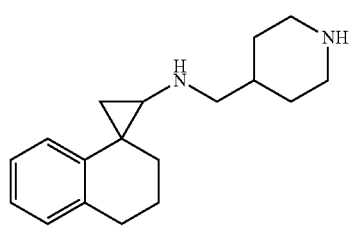 [SMILES: c1ccc2c(c1)CCCC21CC1NCC1CCNCC1]

N-(piperidin-4-ylmethyl)-3',4'-dihydro-2'H-spiro[cyclopropane-1,1'-naphthalen]-2-amine To a solution of tert-butyl 4-(((3',4'-dihydro-2'H-spiro[cyclopropane-1,1'-naphthalen]-2-yl)amino)methyl)piperidine-1-carboxylate (0.073 g, 0.197) in dioxane (3 mL) was added HCl (3 mL, 1M) and the mixture was heated at reflux for 10 min. The solution was concentrated and lyophilized from dioxane/water to afford N-(piperidin-4-ylmethyl)-3',4'-dihydro-2'H-spiro[cyclopropane-1,1'-naphthalen]-2-amine (70 mg). LCMS m/z 271 [M+H]+.

The examples in the following table were prepared according to the above procedure using the appropriate starting materials and modifications.

| Example | Name | Structure | m/z |
|---|---|---|---|
| 53 | N-(3',4'-dihydro-2'H-spiro[cyclopropane-1,1'-naphthalen]-2-yl)piperidin-4-amine | 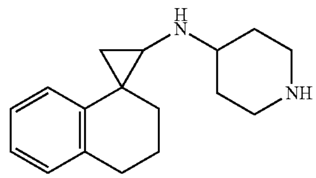 [SMILES: c1ccc2c(c1)CCCC21CC1NC1CCNCC1] | 257 |
| 54 | N1-(3',4'-dihydro-2'H-spiro[cyclopropane-1,1'-naphthalen]-2-yl)cyclohexane-1,4-diamine | 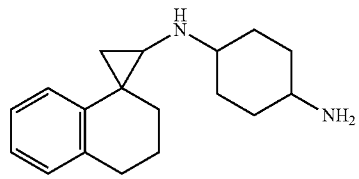 [SMILES: NC1CCC(NC2CC23CCCc2ccccc23)CC1] | 271 |
| 55 | 5'-(benzyloxy)-N-(piperidin-4-ylmethyl)-2',3'-dihydrospiro[cyclopropane-1,1'-inden]-2-amine | 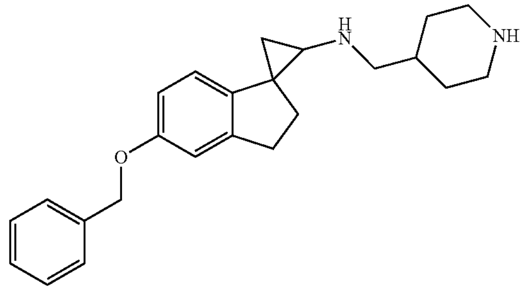 [SMILES: c1ccc(COc2ccc3c(c2)CCC32CC2NCC2CCNCC2)cc1] | 363 |
| 56 | N-(piperidin-4-ylmethyl)-6,7,8,9-tetrahydrospiro[benzo[7]annulene-5,1'-cyclopropan]-2'-amine | 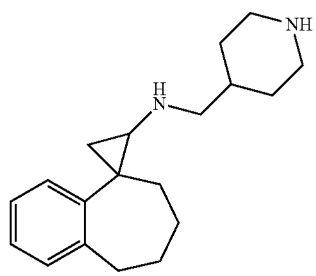 [SMILES: c1ccc2c(c1)CCCCC21CC1NCC1CCNCC1] | 285 |
| 57 | N-(piperidin-3-ylmethyl)-3',4'-dihydro-2'H-spiro[cyclopropane-1,1'-naphthalen]-2-amine | 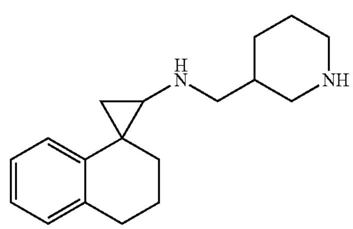 [SMILES: c1ccc2c(c1)CCCC21CC1NCC1CCCNC1] | 271 |
| 58 | N-(piperidin-2-ylmethyl)-3',4'-dihydro-2'H-spiro[cyclopropane-1,1'-naphthalen]-2-amine | 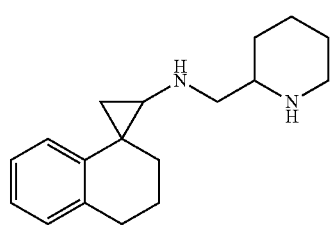 [SMILES: c1ccc2c(c1)CCCC21CC1NCC1CCCCN1] | 271 |
| 59 | 2',3'-dihydro-1'H-spiro[cyclopropane-1,4'-quinolin]-2-amine | 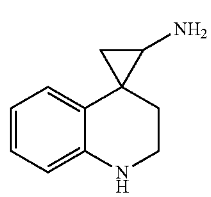 [SMILES: NC1CC12CCNc1ccccc12] | 175 |

-continued

| Example | Name | Structure | m/z |
|---|---|---|---|
| 60 | N-(2-(piperidin-4-yl)ethyl)-3',4'-dihydro-2'H-spiro[cyclopropane-1,1'-naphthalen]-2-amine | 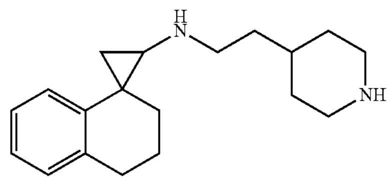 [SMILES: c1ccc2c(c1)CCCC21CC1NCCC1CCNCC1] | 285 |
| 61 | 6'-chloro-N-(piperidin-4-ylmethyl)-2',3'-dihydrospiro[cyclopropane-1,1'-inden]-2-amine | 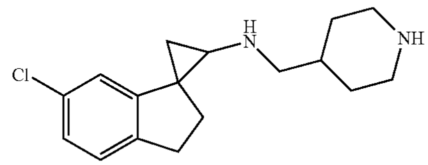 [SMILES: Clc1ccc2c(c1)C1(CC2)CC1NCC1CCNCC1] | 291 |
| 62 | N-(3-(aminomethyl)cyclobutyl)-2',3'-dihydrospiro[cyclopropane-1,1'-inden]-2-amine | 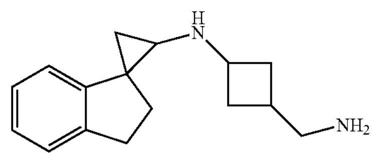 [SMILES: NCC1CC(NC2CC23CCc2ccccc23)C1] | 243 |
| 63 | N-(piperidin-4-ylmethyl)-2',3'-dihydrospiro[cyclopropane-1,1'-inden]-2-amine | 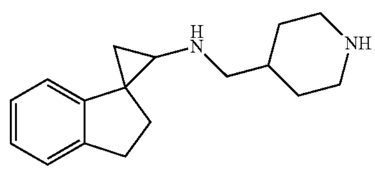 [SMILES: c1ccc2c(c1)CCC21CC1NCC1CCNCC1] | 257 |
| 64 | 5'-chloro-N-(piperidin-4-ylmethyl)-2',3'-dihydrospiro[cyclopropane-1,1'-inden]-2-amine | 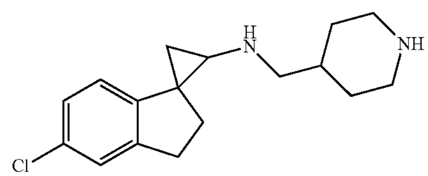 [SMILES: Clc1ccc2c(c1)CCC21CC1NCC1CCNCC1] | 291 |
| 65 | 4'-chloro-N-(piperidin-4-ylmethyl)-2',3'-dihydrospiro[cyclopropane-1,1'-inden]-2-amine | 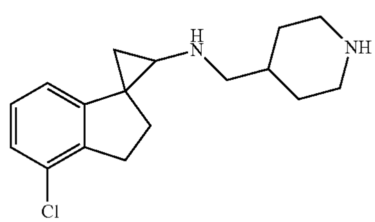 [SMILES: Clc1cccc2c1CCC21CC1NCC1CCNCC1] | 291 |
| 66 | N1-(6'-chloro-2',3'-dihydrospiro[cyclopropane-1,1'-inden]-2-yl)cyclohexane-1,4-diamine | 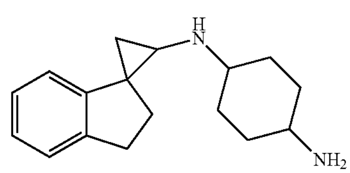 [SMILES: NC1CCC(NC2CC23CCc2ccccc23)CC1] | 257 |
| 67 | N-(piperidin-4-ylmethyl)-6'-(pyridin-3-yl)-2',3'-dihydrospiro[cyclopropane-1,1'-inden]-2-amine | 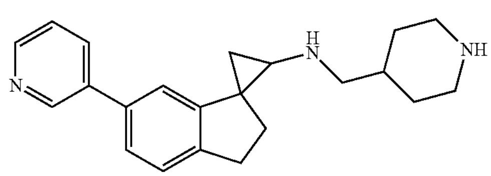 [SMILES: c1cncc(-c2ccc3c(c2)C2(CC3)CC2NCC2CCNCC2)c1] | 334 |
| 68 | N-(3-(aminomethyl)cyclobutyl)-6'-chloro-2',3'-dihydrospiro[cyclopropane-1,1'-inden]-2-amine | 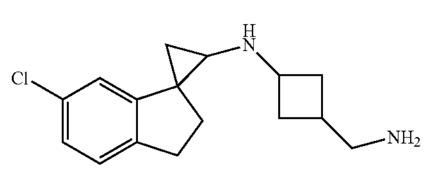 [SMILES: NCC1CC(NC2CC23CCc2ccc(Cl)cc23)C1] | 277 |

| Example | Name | Structure | m/z |
|---|---|---|---|
| 69 | N-(2-(azetidin-3-yl)ethyl)-6'-chloro-2',3'-dihydrospiro[cyclopropane-1,1'-inden]-2-amine | 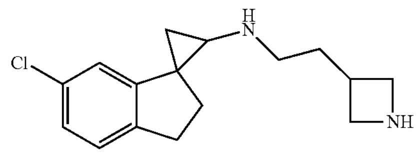 [SMILES: Clc1ccc2c(c1)C1(CC2)CC1NCCC1CNC1] | 277 |
| 70 | N-(2',3'-dihydrospiro[cyclopropane-1,1'-inden]-2-yl)-2-azaspiro[3.3]heptan-6-amine | 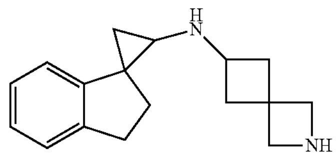 [SMILES: c1ccc2c(c1)CCC21CC1NC1CC2(CNC2)C1] | 255 |
| 71 | 2-((piperidin-4-ylmethyl)amino)-2',3'-dihydrospiro[cyclopropane-1,1'-indene]-6'-carbonitrile | 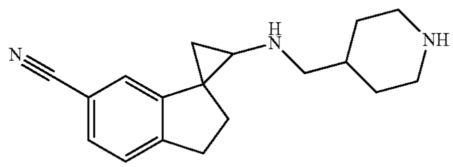 [SMILES: N#Cc1ccc2c(c1)C1(CC2)CC1NCC1CCNCC1] | 282 |
| 72 | 6'-methyl-N-(piperidin-4-ylmethyl)-2',3'-dihydrospiro[cyclopropane-1,1'-inden]-2-amine | 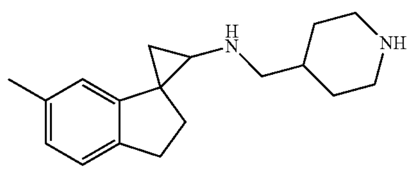 [SMILES: Cc1ccc2c(c1)C1(CC2)CC1NCC1CCNCC1] | 371 |
| 73 | 6'-(1-methyl-1H-pyrazol-4-yl)-N-(piperidin-4-ylmethyl)-2',3'-dihydrospiro[cyclopropane-1,1'-inden]-2-amine | 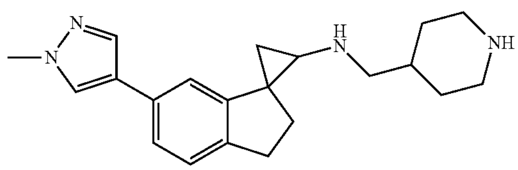 [SMILES: Cn1cc(-c2ccc3c(c2)C2(CC3)CC2NCC2CCNCC2)cn1] | 337 |
| 74 | N-((4-aminocyclohexyl)methyl)-6'-(1-methyl-1H-pyrazol-4-yl)-2',3'-dihydrospiro[cyclopropane-1,1'-inden]-2-amine | 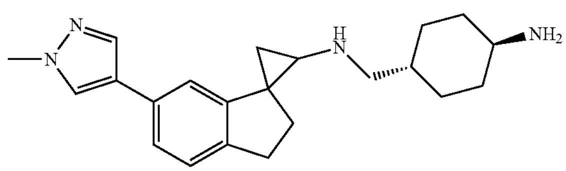 [SMILES: Cn1cc(-c2ccc3c(c2)C2(CC3)CC2NC[C@H]2CC[C@H](N)CC2)cn1] | 351 |
| 75 | 2-((piperidin-4-ylmethyl)amino)-2',3'-dihydrospiro[cyclopropane-1,1'-indene]-6'-carboxylic acid | 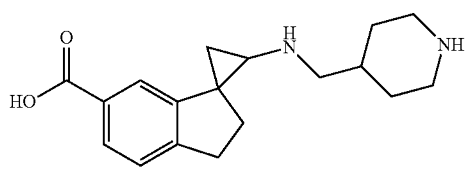 [SMILES: O=C(O)c1ccc2c(c1)C1(CC2)CC1NCC1CCNCC1] | 301 |
| 76 | 7'-fluoro-N-(piperidin-4-ylmethyl)-3',4'-dihydro-2'H-spiro[cyclopropane-1,1'-naphthalen]-2-amine | 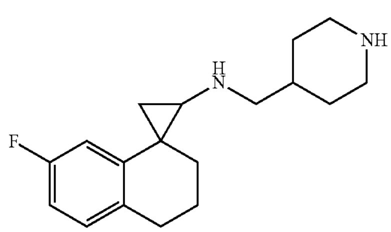 [SMILES: Fc1ccc2c(c1)C1(CCC2)CC1NCC1CCNCC1] | 289 |

The examples in the following table were prepared according to the above procedures using the appropriate starting materials and modifications. The examples in the following table were isolated as single diastereomers following reverse phase HPLC purification.

| Example | Name | Structure | m/z | 1H NMR |
|---|---|---|---|---|
| 77 | N1-(6'-chloro-2',3'-dihydrospiro[cyclopropane-1,1'-inden]-2-yl)cyclohexane-1,4-diamine | 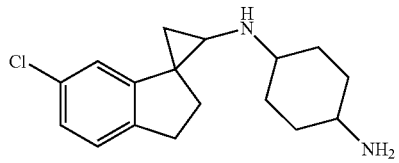<br>single diastereomer | 291 | |
| 78 | N1-(6'-chloro-2',3'-dihydrospiro[cyclopropane-1,1'-inden]-2-yl)cyclohexane-1,4-diamine | 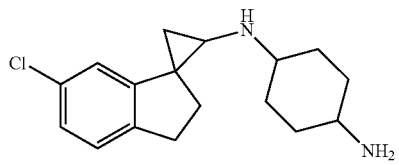<br>single diastereomer | 291 | |
| 79 | N1-(6'-chloro-2',3'-dihydrospiro[cyclopropane-1,1'-inden]-2-yl)cyclohexane-1,4-diamine | 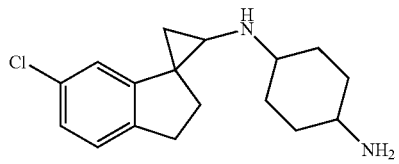<br>single diastereomer | 291 | |
| 80 | N1-(6'-chloro-2',3'-dihydrospiro[cyclopropane-1,1'-inden]-2-yl)cyclohexane-1,4-diamine | 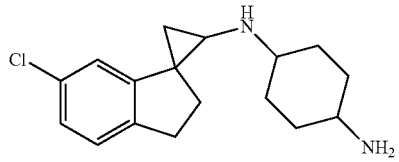<br>single diastereomer | 291 | |
| 81 | 6'-fluoro-N-(piperidin-4-ylmethyl)-2',3'-dihydrospiro[cyclopropane-1,1'-inden]-2-amine | 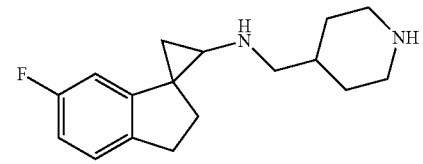<br>single diastereomer | 275 | $^1$H NMR (400 MHz, DMSO-d6) δ 9.13 (br. s., 2H), 8.71 (br. s., 1H), 8.42 (br. s., 1H), 7.24 (dd, J = 5.25, 8.18 Hz, 1H), 6.91-7.00 (m, 1H), 6.73 (dd, J = 2.32, 9.40 Hz, 1H), 3.30 (d, J = 12.94 Hz, 2H), 2.94-3.11 (m, 5H), 2.87 (q, J = 11.48 Hz, 2H), 2.17-2.37 (m, 2H), 1.80-2.06 (m, 2H), 1.32-1.50 (m, 3H) |
| 82 | 6'-fluoro-N-(piperidin-4-ylmethyl)-2',3'-dihydrospiro[cyclopropane-1,1'-inden]-2-amine | 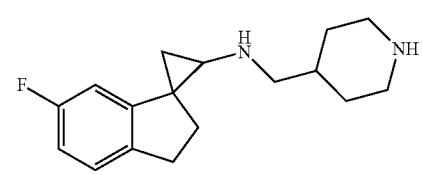<br>single diastereomer | 275 | $^1$H NMR (400 MHz, DMSO-d6) δ 9.34 (br. s., 1H), 8.59 (br. s., 1H), 8.23 (br. s., 2H), 7.28-7.35 (m, J = 5.90 Hz, 1H), 7.17-7.26 (m, 1H), 6.94-7.10 (m, 1H), 3.20 (d, J = 12.21 Hz, 2H) 2.66-3.12 (m, 5H), 2.13-2.35 (m, 2H), 1.94 (dd, J = 8.06, 10.99 Hz, 1H), 1.79 (d, J = 13.92 Hz, 2H), 1.66 (d, J = 13.92 Hz, 2H), 1.42 (br. s., 1H), 1.13-1.25 (m, J = 13.20 Hz, 1H), 0.96-1.13 (m, J = 12.70 Hz, 1H) |

-continued

| Example | Name | Structure | m/z | 1H NMR |
|---|---|---|---|---|
| 83 | 7'-chloro-N-(piperidin-4-ylmethyl)-3',4'-dihydro-2'H-spiro[cyclopropane-1,1'-naphthalen]-2-amine | single diastereomer | 305 | |
| 84 | 7'-chloro-N-(piperidin-4-ylmethyl)-3',4'-dihydro-2'H-spiro[cyclopropane-1,1'-naphthalen]-2-amine | single diastereomer | 305 | |

Example 85

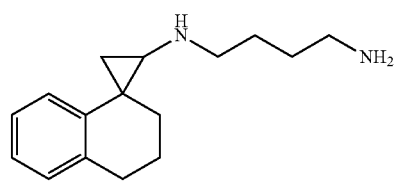 [SMILES: NCCCCNC1CC12CCCc1ccccc12]

N1-(3',4'-dihydro-2'H-spiro[cyclopropane-1,1'-naphthalen]-2-yl)butane-1,4-diamine Step 1:

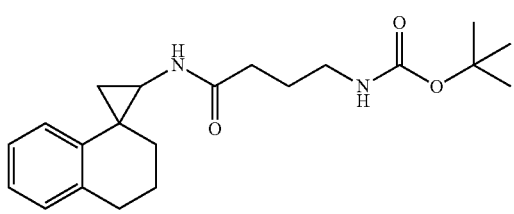 [SMILES: CC(C)(C)OC(=O)NCCCC(=O)NC1CC12CCCc1ccccc12]

tert-butyl (4-((3',4'-dihydro-2'H-spiro[cyclopropane-1,1'-naphthalen]-2-yl)amino)-4-oxobutyl)carbamate 3',4'-Dihydro-2'H-spiro[cyclopropane-1,1'-naphthalen]-2-amine (100 mg, 0.577 mmol) and 4-((tert-butoxycarbonyl)amino)butanoic acid (128 mg, 0.634 mmol) were dissolved in DMF (1.5 mL), before addition of diisopropylethylamine (199 μL, 1.15 mmol) and the reaction mixture was cooled to 0° C. HATU (241 mg, 0.634 mmol) was added and the reaction mixture was stirred one hour. The reaction mixture was partitioned between NaHCO₃ (aq., sat.) and EtOAc. The organics phase was washed with brine, dried with Na₂SO₄, filtered, and evaporated under reduced pressure. The crude residue was purified on a silica gel column using 5% to 100% EtOAc in hexanes as an eluent gradient. Pure fractions were evaporated to afford tert-butyl (4-((3',4'-dihydro-2'H-spiro[cyclopropane-1,1'-naphthalen]-2-yl)amino)-4-oxobutyl)carbamate (200 mg, 0.557 mmol). LCMS m/z 381 [M+Na]⁺.

Step 2:

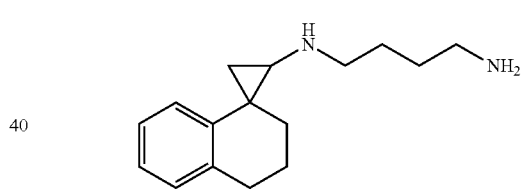

N1-(3',4'-dihydro-2'H-spiro[cyclopropane-1,1'-naphthalen]-2-yl)butane-1,4-diamine tert-Butyl (4-((3',4'-dihydro-2'H-spiro[cyclopropane-1,1'-naphthalen]-2-yl)amino)-4-oxobutyl)carbamate (200 mg, 0.557 mmol) was dissolved in dioxane (2 mL), and HCl (4M in dioxane) was added. The volatiles were removed under reduced pressure to afford the crude residue. This crude residue was dissolved/suspended in THF, cooled to 0° C. BH₃.DMS (1.4 mL, 2.8 mmol) was added and stirred for 15 minutes. The reaction mixture was heated to 60° C. for 2 hours before being cooled down to 0° C. and addition of methanol (caution! Hydrogen gas generated). Mixture heated to 50° C. and stirred for 30 minutes. Volatiles were evaporated under reduced pressure. Crude residue was purified by preparative HPLC (Acetonitrile:water with 0.1% TFA on a SunFire column) Pure fractions pooled, frozen and lyophilized to afford N1-(3',4'-dihydro-2'H-spiro[cyclopropane-1,1'-naphthalen]-2-yl)butane-1,4-diamine bis(2,2,2-trifluoroacetate) (89 mg, 188 μmol) as a mixture of diastereomers in 34% yield over 2 steps. LCMS m/z 245 [M+H]⁺.

The examples in the following table were prepared according to the above procedures using the appropriate starting materials and modifications.

| Example | Name | Structure | m/z |
|---|---|---|---|
| 86 | N1-(3',4'-dihydro-2'H-spiro[cyclopropane-1,1'-naphthalen]-2-yl)propane-1,3-diamine | 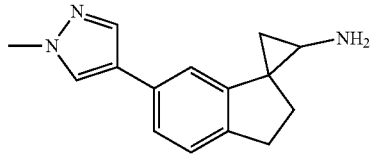 [SMILES: Cn1cc(-c2ccc3c(c2)C2(CC3)CC2N)cn1] | 231 |

Examples 87 and 88

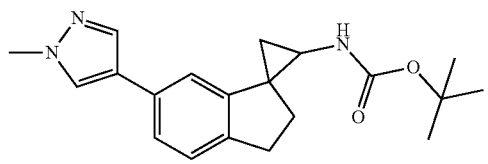 [SMILES: Cn1cc(-c2ccc3c(c2)C2(CC3)CC2NC(=O)OC(C)(C)C)cn1]

6'-(1-methyl-1H-pyrazol-4-yl)-2',3'-dihydrospiro[cyclopropane-1,1'-inden]-2-amine Step 1:

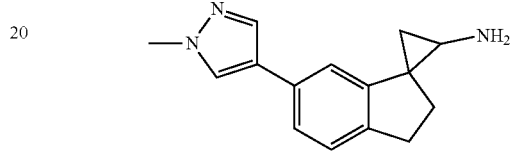

tert-butyl (6'-(1-methyl-1H-pyrazol-4-yl)-2',3'-dihydrospiro[cyclopropane-1,1'-inden]-2-yl)carbamate To a re-sealable vial was added tert-butyl (6'-bromo-2',3'-dihydrospiro[cyclopropane-1,1'-inden]-2-yl)carbamate (0.113 g, 334 μmol), 1-methyl-4-(4,4,5,5-tetramethyl-1,3,2-dioxaborolan-2-yl)-1H-pyrazole (104 mg, 500 μmop, Pd$_2$(dba)$_3$ (15.2 mg, 16.7 μmop, (t-Bu)$_3$P.HBF$_4$ (9.69 mg, 33.4 μmol), and potassium phosphate hydrate (153 mg, 668 μmol). The vial was evacuated and purged with N$_2$ (3×) and subsequently diluted with 1,4-dioxane (2 mL) and water (0.1 mL). The contents were evacuated and purged with N$_2$ (3×) and subsequently heated to 110° C. for 3 h. The reaction mixture was cooled to room temperature and filter over a pad of silica and Celite. The filter cake was washed with EtOAc (2×) and the filtrate concentrated to give brown oil. The oil was purified via silica gel chromatography (gradient elution 12% EtOAc:Hex to 95% EtOAc:Hex, then isocratic 95% EtOAc:Hex). The complete separation of diastereomers was achieved.

Major diastereomer: 78.6 mg LC-MS m/z 340 [M+H]$^+$.
Minor diastereomer: 25.9 mg LC-MS m/z 340 [M+H]$^+$.

Step 2:

Single Diastereomer

6'-(1-methyl-1H-pyrazol-4-yl)-2',3'-dihydrospiro[cyclopropane-1,1'-inden]-2-amine (Major Diastereomer)

To a solution of tert-butyl (6'-(1-methyl-1H-pyrazol-4-yl)-2',3'-dihydrospiro[cyclopropane-1,1'-inden]-2-yl)carbamate (0.1300 g, 382 μmol) in 1,4-dioxane (1 mL) and IPA (1 mL) was added a solution of HCl (0.600 mL, 2.40 mmol, 1 M) in 1,4-dioxane. The reaction mixture turned heterogeneous with precipitates after 24 h. After stirring for 24 h, the reaction mixture was concentrated in vacuo to yield light yellow solids. The solids were triturated with 10% EtOAc/Hexanes and filtered. The product 6'-(1-methyl-1H-pyrazol-4-yl)-2',3'-dihydrospiro[cyclopropane-1,1'-inden]-2-aminium chloride (92.0 mg, 333 μmol) was isolated as light yellow solids.

LC-MS m/z 240 [M+H]$^+$.
$^1$H NMR (400 MHz, DMSO-d$_6$) δ 8.65 (br. s., 3H), 8.07 (s, 1H), 7.82 (d, J=0.7 Hz, 1H), 7.34 (dd, J=7.8, 1.5 Hz, 1H), 7.18 (d, J=7.8 Hz, 1H), 7.05 (d, J=1.0 Hz, 1H), 3.83 (s, 3H), 2.93-3.10 (m, 2H), 2.81-2.91 (m, 1H), 2.23-2.35 (m, 1H), 2.08-2.22 (m, 1H), 1.34-1.42 (m, 1H), 1.27-1.33 (m, 1H).

The minor diastereomer was processed separately via the same chemistry to afford the Example 89:

| Example | Name | Structure | m/z | NMR |
|---|---|---|---|---|
| 88 | 6'-(1-methyl-1H-pyrazol-4-yl)-2',3'-dihydrospiro[cyclopropane-1,1'-inden]-2-amine | single diastereomer | 240 | $^1$H NMR (400 MHz, DMSO-d$_6$) δ 8.48 (br. s., 3H), 8.17 (s, 1H), 7.93 (d, J = 0.7 Hz, 1H), 7.62 (s, 1H), 7.40 (dd, J = 7.6, 1.5 Hz, 1H), 7.25 (d, J = 7.8 Hz, 1H), 3.79-3.89 (m, 3H), 2.80-3.05 (m, 3H), 2.19 (td, J = 12.7, 9.6 Hz, 1H), 1.91-2.03 (m, 1H), 1.63 (dd, J = 6.4, 4.9 Hz, 1H), 1.32 (t, J = 7.2 Hz, 1H). |

Example 89

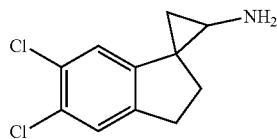 [SMILES: NC1CC12CCc1cc(Cl)c(Cl)cc12]

5',6'-dichloro-2',3'-dihydrospiro[cyclopropane-1,1'-inden]-2-amine (Minor Diastereomer)

5',6'-Dichloro-2',3'-dihydrospiro[cyclopropane-1,1'-inden]-2-amine hydrochloride: To a solution of 5',6'-dichloro-2',3'-dihydrospiro[cyclopropane-1,1'-indene]-2-carboxylic acid (1.7 g, 6.61 mmol) and ethyl carbonochloridate (860 mg, 7.93 mmol) in THF (66 mL) was added N-ethyl-N-isopropylpropan-2-amine (2.55 g, 19.8 mmol) at 0° C. After stirring at 0° C. for 3 h, a solution of sodium azide (4.29 g, 66.1 mmol) in water (50 mL) was added at 0° C. and the reaction was stirred for an additional 4 h. The product was extracted with MTBE (repeated twice), dried over $Na_2SO_4$, filtered and concentrated to dryness under vacuum. The residue was dissolved in benzene (60 mL) and heated to reflux. After 6 h the reaction was cooled to room temperature and potassium trimethylsilanolate (1.69 g, 13.2 mmol) was added. The reaction was stirred for an additional 30 min, then quenched with aq. $NH_4Cl$ solution. 2M HCl was added until pH<2 and the biphasic mixture was vigorously stirred for 10 min. The pH was adjusted to >9 with NaOH( ) and the desired product was extracted with MTBE (repeated three times). The combined organic layers were dried with $Na_2SO_4$, filtered and concentrated to dryness under vacuum. Both diastereoisomers were separated and purified by flash chromatography using a hexane/ethyl acetate (95:5 to 0:100) mixture as eluent. Each diastereoisomer was further purified by adding 1M HCl and MTBE and stirring vigorously. The remaining solid was recovered by filtration and dried under vacuum to give the title compound as a tan solid. The filtrate was extracted twice with MTBE, then $NaOH_{(s)}$ was added until pH>10. The desired product was extracted with MTBE (repeated three times), dried with $Na_2SO_4$, filtered, salted with HCl in 1,4-dioxane and concentrated to dryness under vacuum to afford the titled compound.

Major diastereoisomer: tan solid (355 mg; 20% yield). LC/MS $[M+H]^+$ 228.

Minor diastereomer: tan solid (110 mg, 6% yield). LC/MS $[M+H]^+$ 228.

Examples 90 and 91

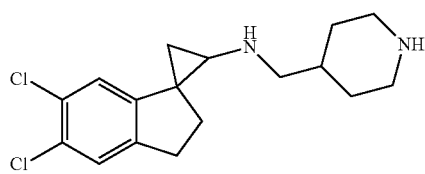 [SMILES: Clc1cc2c(cc1Cl)C1(CC2)CC1NCC1CCNCC1]

5',6'-dichloro-N-(piperidin-4-ylmethyl)-2',3'-dihydrospiro[cyclopropane-1,1'-inden]-2-amine Step 1:

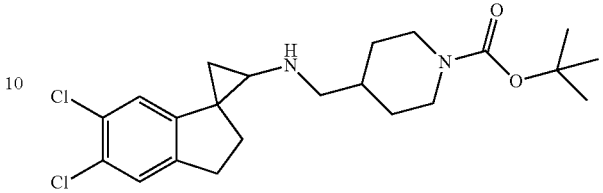

tert-butyl 4-(((5',6'-dichloro-2',3'-dihydrospiro[cyclopropane-1,1'-inden]-2-yl)amino)methyl)piperidine-1-carboxylate (Major Diastereomer)

To a suspension of 5',6'-dichloro-2',3'-dihydrospiro[cyclopropane-1,1'-inden]-2-amine hydrochloride (100 mg, 0.38 mmol) and tert-butyl 4-formylpiperidine-1-carboxylate (80 mg, 0.38 mmol) in DCE (3 mL) was added sodium triacetoxyborohydride (120 mg, 0.57 mmol) at room temperature. After 1 h, additional sodium triacetoxyborohydride (120 mg, 0.57 mmol) was added and the reaction was stirred for another 2 h. The reaction was quenched with aq. $NaHCO_3$ solution and the desired product was extracted with dichloromethane (repeated 3 times). The combined organic layers were washed with water, dried with $Na_2SO_4$, filtered and concentrated to dryness under vacuum. The desired product was purified twice by flash chromatography using a hexane/ethyl acetate (60:40) mixture as eluent. The title compound was obtained as a solid (60 mg; 38% yield). LCMS m/z 447 $[M+Na]^+$.

Step 2:

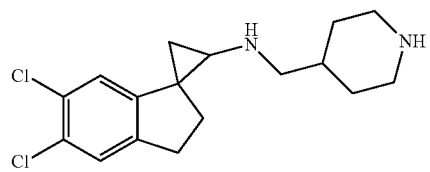 [SMILES: Clc1cc2c(cc1Cl)C1(CC2)CC1NCC1CCNCC1]

Single Diastereomer

5',6'-dichloro-N-(piperidin-4-ylmethyl)-2',3'-dihydrospiro[cyclopropane-1,1'-inden]-2-amine (Example 99, Major Diastereomer)

To a solution of tert-butyl 4-(((5',6'-dichloro-2',3'-dihydrospiro[cyclopropane-1,1'-inden]-2-yl)amino)methyl)piperidine-1-carboxylate (60 mg, 0.14 mmol) in MeOH (5 mL) was added hydrogen chloride (4M in 1,4-dioxane) (0.88 μL, 3.5 mmol). After 90 minutes, the reaction was concentrated to dryness. The HCl salt of the title compound was obtained as a tan solid (56 mg; >98% yield). LC/MS m/z 325 $[M+H]^+$.

The minor diastereomer was processed separately via similar chemistry to afford the Example 91.

| Example | Name | Structure | m/z |
|---|---|---|---|
| 91 | 5',6'-dichloro-N-(piperidin-4-ylmethyl)-2',3'-dihydrospiro[cyclopropane-1,1'-inden]-2-amine | 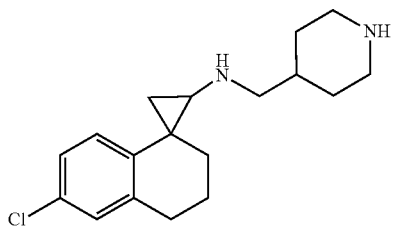 [SMILES: Clc1ccc2c(c1)CCCC21CC1NCC1CCNCC1]
single diastereomer | 325 |

Examples 92 and 93

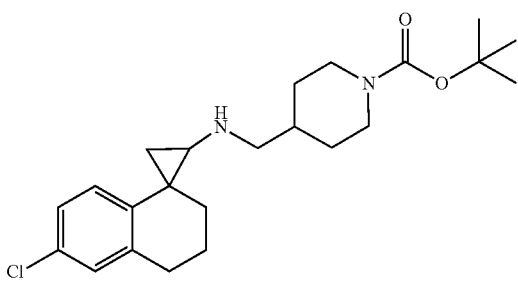 [SMILES: CC(C)(C)OC(=O)N1CCC(CNC2CC23CCCc2cc(Cl)ccc23)CC1]

6'-chloro-N-(piperidin-4-ylmethyl)-3',4'-dihydro-2'H-spiro[cyclopropane-1,1'-naphthalen]-2-amine Step 1:

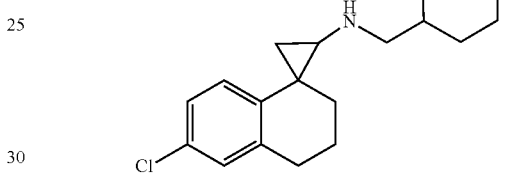

tert-butyl 4-(((6'-chloro-3',4'-dihydro-2'H-spiro[cyclopropane-1,1'-naphthalen]-2-yl)amino)methyl)piperidine-1-carboxylate To a round bottomed flask charged with 6'-chloro-3',4'-dihydro-2'H-spiro[cyclopropane-1,1'-naphthalen]-2-amine hydrochloride (85 mg, 348 μmol) and tert-butyl 4-formylpiperidine-1-carboxylate (75.4 mg, 354 μmol) was added sodium triacetoxyborohydride (220 mg). The solution was stirred for 30 min before addition of potassium carbonate solution (1 M). The phases were separated and the organics phase was washed with brine, dried over $Na_2SO_4$, filtered, and concentrated. The crude residue was purified via silica gel chromatography to afford two diastereomers.

Diastereomer A, 46.0 mg, LCMS m/z 349 [M-tBu+H]$^+$.
Diastereomer B, 30.0 mg, LCMS m/z 349 [M-tBu+H]$^+$.

Step 2:

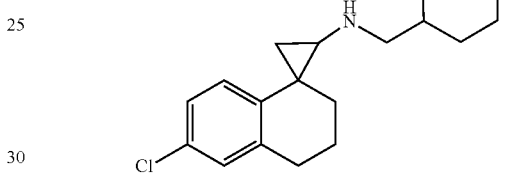

Single Diastereomer

6'-chloro-N-(piperidin-4-ylmethyl)-3',4'-dihydro-2'H-spiro[cyclopropane-1,1'-naphthalen]-2-amine
(Example 101, Diastereomer A)

To a round bottomed flask charged with tert-butyl 4-(((6'-chloro-3',4'-dihydro-2'H-spiro[cyclopropane-1,1'-naphthalen]-2-yl)amino)methyl)piperidine-1-carboxylate (diastereomer A, 46.0 mg, 0.113 mmol) and dioxane was added HCl (0.5 mL, 2 mmol). The solution was stirred at room temperature for 1 h before being concentrated. The solid residue was triturated with MTBE to afford 6'-chloro-N-(piperidin-4-ylmethyl)-3',4'-dihydro-2'H-spiro[cyclopropane-1,1'-naphthalen]-2-amine (25.0 mg, 66.1 μmol).

$^1$H-NMR (400 MHz, DMSO-d6): 9.56 (br. s., 2H), 9.00 (m, 1H), 8.83 (m, 1H), 7.13-7.17 (m, 2H), 6.73 (d, J=8.3 Hz, 1H), 3.23-3.26 (m, 2H), 3.02-3.06 (m, 2H), 2.94-2.99 (m, 1H), 2.80-2.83 (m, 4H), 2.16-2.21 (m, 1H), 2.02-2.09 (m, 3H), 1.93-1.95 (m, 2H), 1.75-1.79 (m, 1H), 1.40-1.52 (m, 3H), 1.32-1.34 (m, 1H). LCMS m/z 307 [M+H]$^+$.

The diastereomer B was processed separately via similar chemistry to afford Example 93:

| Example | Name | Structure | m/z | 1H NMR |
|---|---|---|---|---|
| 93 | 6'-chloro-N-(piperidin-4-ylmethyl)-3',4'-dihydro-2'H-spiro[cyclopropane-1,1'-naphthalen]-2-amine | 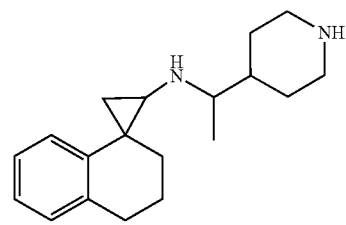 [SMILES: CC(NC1CC12CCCc1ccccc12)C1CCNCC1]<br>single diastereomer | 307 | 1H-NMR (400 MHz, DMSO-d6): 9.76 (br. s., 1H), 8.89 (br. s., 1H), 8.60 (br. s., 1H), 8.31 (br. s., 1H), 7.40 (d, J = 8.3 Hz, 1H), 7.25 (d, J =1.9 Hz, 1H), 7.16 (dd, J = 1.8, 8.3 Hz, 1H), 3.11-3.17 (m, 3H), 2.78-2.95 (m, 3H), 2.60-2.73 (m, 3H), 2.12-2.18 (m, 1H), 1.73-1.96 (m, 6H), 1.22-1.29 (m, 3H), 0.97-1.00 (m, 1H). |

Examples 94, 95, 96 and 97

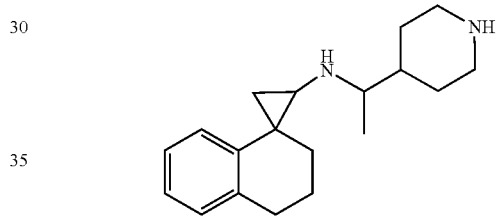

N-(1-(piperidin-4-yl)ethyl)-3',4'-dihydro-2'H-spiro[cyclopropane-1,1'-naphthalen]-2-amine Step 1:

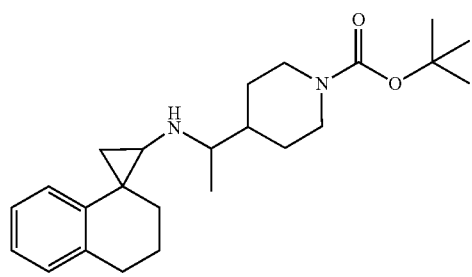 [SMILES: CC(NC1CC12CCCc1ccccc12)C1CCN(C(=O)OC(C)(C)C)CC1]

tert-butyl 4-(1-(3',4'-dihydro-2'H-spiro[cyclopropane-1,1'-naphthalen]-2-yl)amino)ethyl)-piperidine-1-carboxylate To 3',4'-dihydro-2'H-spiro[cyclopropane-1,1'-naphthalen]-2-amine (100 mg, 0.577 mmol) and tert-butyl 4-acetylpiperidine-1-carboxylate (131 mg, 0.577 mmol) were dissolved in DCE (3 mL). NaBH(OAc)₃ was added and the reaction mixture was stirred. After 30 min, 1 M potassium carbonate aqueous was added (5 mL) and stirred for 15 minutes. The reaction mixture was extracted with DCM. The crude residue was purified on a 40 g column with a 5% to 40% EtOAc in hexanes gradient to afford three different fractions of diasteomers of tert-butyl 4-(1-((3',4'-dihydro-2'H-spiro[cyclopropane-1,1'-naphthalen]-2-yl)amino)ethyl) piperidine-1-carboxylate: Fraction A, Fraction B (mixture of 2 diastereomers) and Fraction C, by order of elution from first to last. The three fractions were evaporated separately under reduced pressure.

Fraction A: LCMS m/z 385 [M+H]⁺.

Fraction B (mixture of two compounds): LCMS m/z 385 [M+H]⁺.

Fraction C: LCMS m/z 385 [M+H]⁺.

Step 2:

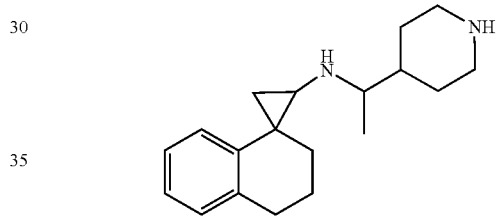

N-(1-(piperidin-4-yl)ethyl)-3',4'-dihydro-2'H-spiro[cyclopropane-1,1'-naphthalen]-2-amine

Example 94

Fraction A (single compound) dissolved in dioxane (2 mL) and HCl (4M in dioxane) (2 mL, 8 mmol) was stirred for one hour. The volatiles were evaporated under reduced pressure and the crude residue was purified to by preparative HPLC. Fractions were frozen and lyophilized to afford N-(1-(piperidin-4-yl)ethyl)-3',4'-dihydro-2'H-spiro[cyclopropane-1,1'-naphthalen]-2-amine. LCMS m/z 285 [M+H]⁺., >95% purity (215 nm UV).

Examples 95 and 96

Fraction B (mixture of two species) was dissolved in dioxane (2 mL) and HCl (4M in dioxane) (2 mL, 8 mmol) was added and stirred for one hour. The volatiles were evaporated under reduced pressure and the crude residue was purified to by preparative HPLC to afford two sets of fractions. The first eluting fractions were frozen and lyophilized to afford N-(1-(piperidin-4-yl)ethyl)-3',4'-dihydro-2'H-spiro[cyclopropane-1,1'-naphthalen]-2-amine (Example 104) LCMS m/z 285 [M+H]⁺. The last eluting fractions were frozen and lyophilized to afford N-(1-(piperidin-4-yl)ethyl)-3',4'-dihydro-2'H-spiro[cyclopropane-1,1'-naphthalen]-2-amine (Example 105). LCMS m/z 285 [M+H]+.

Example 97

Fraction C (single compound) was dissolved in dioxane (2 mL) and HCl (4M in dioxane) (2 mL, 8 mmol added and stirred for one hour. The volatiles were evaporated under reduced pressure and the crude residue was purified to by preparative HPLC. Fractions were frozen and lyophilized to afford N-(1-(piperidin-4-yl)ethyl)-3',4'-dihydro-2'H-spiro[cyclopropane-1,1'-naphthalen]-2-amine. LCMS m/z 285 [M+H]+.

Example 98

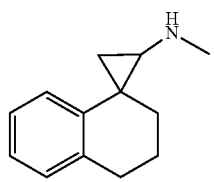

N-methyl-3',4'-dihydro-2'H-spiro[cyclopropane-1,1'-naphthalen]-2-amine

To acetic anhydride (0.73 mL, 7.8 mmol) at 0° C. was added formic acid (0.36 mL, 9.6 mmol) and the mixture was heated to 50° C. for 2 h. The reaction was cooled to room temperature before addition of THF (5 mL) to provide a solution of aceticformic anhydride (1.28 mmol/mL). This anhydride solution (0.2 mL) was added to a suspension of 3',4'-dihydro-2'H-spiro[cyclopropane-1,1'-naphthalen]-2-amine hydrochloride (0.027 g, 0.128 mmol) in THF (1 mL) at −15 C followed by addition of N-methylmorpholine (22 uL, 20 mmol). After 30 min at −15° C. the reaction was warmed to room temperature for 1 h before being concentrated. The crude residue was purified via silica gel chromatography to afford N-(3',4'-dihydro-2'H-spiro[cyclopropane-1,1'-naphthalen]-2-yl)formamide. LCMS m/z 202 [M+H]+.

To the N-formyl derivative (0.020 g, 0.099 mmol) was added THF (0.5 mL) and borane-dimethyl sulfide complex (0.23 mL). The reaction was heated to 65° C. for 4 h before cooling to room temperature and addition of excess methanol and 1M HCl. This solution was heated to reflux for 30 min before cooling to room temperature and basifying with 1M NaOH. The solution was concentrated and taken up in DCM before being dried over $Na_2SO_4$, filtered, and concentrated. The crude residue was purified via Silica gel chromatography to afford N-methyl-3',4'-dihydro-2'H-spiro[cyclopropane-1,1'-naphthalen]-2-amine (10 mg). LCMS m/z 188 [M+H]+.

Example 99

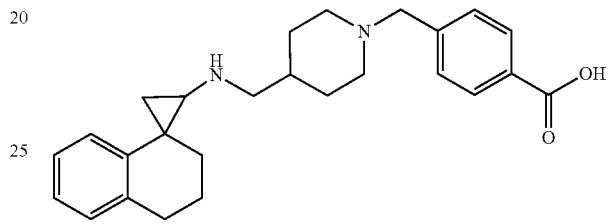

4-((4-(((3',4'-dihydro-2'H-spiro[cyclopropane-1,1'-naphthalen]-2-yl)amino)methyl)piperidin-1-yl)methyl)benzoic acid To a solution of tert-butyl 4-((4-(((3',4'-dihydro-2'H-spiro[cyclopropane-1,1'-naphthalen]-2-yl)amino)methyl)piperidin-1-yl)methyl)benzoate (0.014 g, 0.030 mmol) in DCM (2 mL) was added TFA (0.3 mL) and the reaction stirred at room temperature. After completion, the solvents were evaporated to afford the title compound as a TFA salt. LCMS m/z 405 [M+H]+.

The compounds in the following table were prepared according to the above procedures using the appropriate starting materials and modifications.

| Example | Name | Structure | m/z |
|---|---|---|---|
| 100 | 4-((4-(((6'-(pyridin-3-yl)-2',3'-dihydrospiro[cyclopropane-1,1'-inden]-2-yl)amino)methyl)piperidin-1-yl)methyl)benzoic acid | 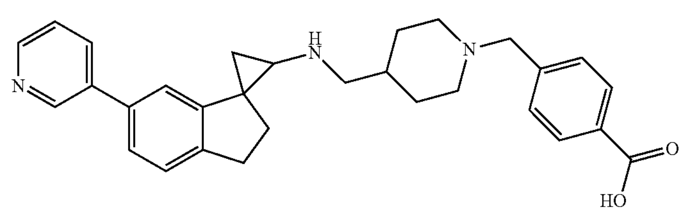 [SMILES: O=C(O)c1ccc(CN2CCC(CNC3CC34CCc3ccc(-c5cccnc5)cc34)CC2)cc1] | 468 |
| 101 | 3-(4-(((2',3'-dihydrospiro[cyclopropane-1,1'-inden]-2-yl)amino)methyl)piperidin-1-yl)propanoic acid | 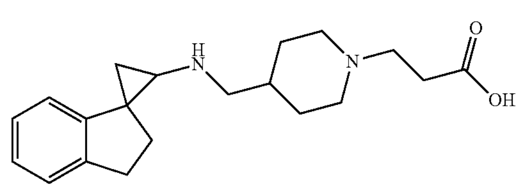 [SMILES: O=C(O)CCN1CCC(CNC2CC23CCc2ccccc23)CC1] | 329 |

| Example | Name | Structure | m/z |
|---|---|---|---|
| 102 | 4-((4-(((2',3'-dihydrospiro[cyclopropane-1,1'-inden]-2-yl)amino)methyl)piperidin-1-yl)methyl)benzoic acid | 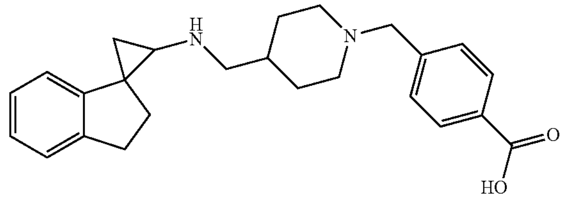 [SMILES: O=C(O)c1ccc(CN2CCC(CNC3CC34CCc3ccccc34)CC2)cc1] | 391 |

Example 103

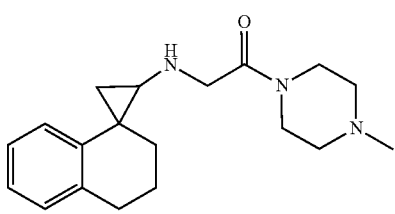 [SMILES: CN1CCN(C(=O)CNC2CC23CCCc2ccccc23)CC1]

2-((3',4'-dihydro-2'H-spiro[cyclopropane-1,1'-naphthalen]-2-yl)amino)-1-(4-methylpiperazin-1-yl)ethan-1-one Step 1:

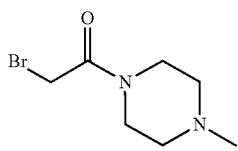

2-bromo-1-(4-methylpiperazin-1-yl)ethan-1-one

To a solution of bromoacetyl chloride (0.035 mL, 0.149 mmol) in MeCN (1.5 mL) at 0° C. was added 1-methylpiperazine (0.046 mL, 0.149 mmol). The solution was stirred for 2 h before the mixture was used without further purification in the next step.

Step 2:

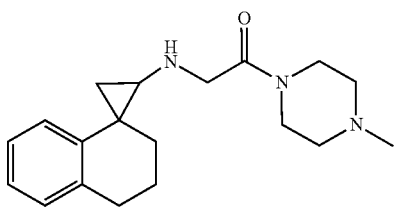 [SMILES: CN1CCN(C(=O)CNC2CC23CCCc2ccccc23)CC1]

2-((3',4'-dihydro-2'H-spiro[cyclopropane-1,1'-naphthalen]-2-yl)amino)-1-(4-methylpiperazin-1-yl)ethan-1-one To a solution of 2-bromo-1-(4-methylpiperazin-1-yl)ethan-1-one in MeCN was added 3',4'-dihydro-2'H-spiro[cyclopropane-1,1'-naphthalen]-2-amine hydrochloride (0.087 g, 0.416 mmol) and Hunig's base (0.183 mL, 1.03 mmol). The reaction was stirred for 18 h before concentrating. The crude residue was purified via reverse phase HPLC to afford the title compound as a TFA salt. LCMS m/z 314 [M+H]⁺.

Examples 104 and 105

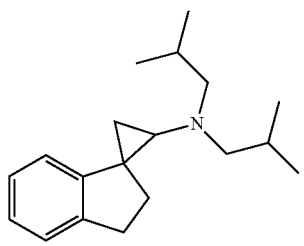 [SMILES: CC(C)CN(CC(C)C)C1CC12CCc1ccccc12]

N,N-diisobutyl-2',3'-dihydrospiro[cyclopropane-1,1'-inden]-2-amine

To a resealable vial was added 2',3'-dihydrospiro[cyclopropane-1,1'-inden]-2-amine (70 mg, 439 µmol), dioxane (1.5 mL), and isobutyraldehyde. The solution was stirred at room temperature for 30 min before addition of sodium triacetoxyborohydride (186 mg, 0.878 mmol). The solution was stirred at room temperature for 1 h. The solution was then diluted with water and extracted with DCM. The combined organics were dried over Na₂SO₄, filtered, and concentrated. The crude residue was purified via Silica gel chromatography to afford two diastereomers (Example 113 diastereomer 1: 3.7 mg, Example 114 diastereomer 2: 16 mg).

Example 104 (diastereomer 1): LCMS m/z 272 [M+H]⁺.
Example 105 (diastereomer 2): LCMS m/z 272 [M+H]⁺.

Example 106

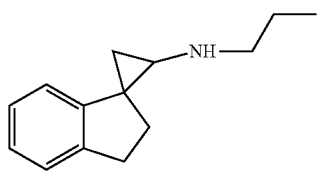

121

N-propyl-2',3'-dihydrospiro[cyclopropane-1,1'-inden]-2-amine

Step 1:

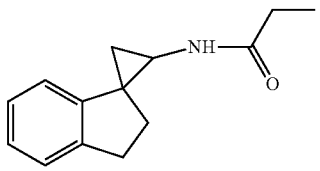 [SMILES: CCC(=O)NC1CC12CCc1ccccc12]

N-(2',3'-dihydrospiro[cyclopropane-1,1'-inden]-2-yl)propionamide

To a mixture of 2',3'-dihydrospiro[cyclopropane-1,1'-inden]-2-amine (200 mg, 1.26 mmol) in DCM (10 mL) were added propionyl chloride (128 mg, 1.39 mmol) and triethylamine (382 mg, 3.78 mmol) portion-wise at 0° C. The mixture was stirred at 25° C. for 15 h. The reaction was monitored by LCMS and TLC. The mixture was quenched with water (15 mL) and extracted with DCM (20 mL×3). The combined organic layers were dried over anhydrous $Na_2SO_4$ and concentrated under vacuum to give crude product. The crude product was purified by Prep-TLC (ethyl acetate) and to afford N-spiro[cyclopropane-2,1'-indane]-1-ylpropanamide (100 mg 0.464 mmol, 37% yield) as a colorless oil. LCMS m/z 216 $[M+H]^+$.

Step 2:

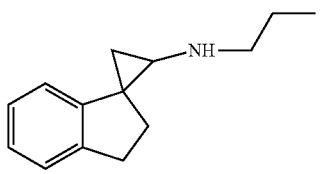

N-propyl-2',3'-dihydrospiro[cyclopropane-1,1'-inden]-2-amine

To a mixture of N-spiro[cyclopropane-2,1'-indane]-1-yl-propanamide (100 mg, 0.464 mmol) in THF (4 mL) was added $BH_3$-$Me_2S$ (460 uL, 10 mol/L) drop-wise at 0° C. under $N_2$. The mixture was stirred at 25° C. for 3 h. The reaction was monitored by LCMS and TLC. The mixture was quenched with MeOH and water (20 mL) and extracted with ethyl acetate (20 mL×3). The combined organic layers were dried over anhydrous $Na_2SO_4$ and concentrated under vacuum. The crude product was purified by Prep-HPLC (Mobile phase A: water with 0.05% hydrogen chloride; Mobile phase B: MeCN; column temperature: 30° C., Gradient: 15-45% B 10 min) to afford N-propylspiro[cyclopropane-2,1'-indane]-1-amine (5.0 mg, 0.022 mmol, 4.81% yield, 90% purity) as a yellow solid. LCMS m/z 202 $[M+H]^+$.

$^1H$ NMR (400 MHz, METHANOL-$d_4$) δ 7.35 (d, J=6.6 Hz, 1H), 7.31-7.12 (m, 3H), 6.80 (d, J=6.2 Hz, 1H), 3.15 (t, J=7.5 Hz, 3H), 3.04-2.89 (m, 2H), 2.32 (t, J=7.5 Hz, 1H), 1.89-1.72 (m, 2H), 1.63-1.45 (m, 2H), 1.40-1.28 (m, 1H), 1.05 (t, J=7.4 Hz, 2H), 0.85 (t, J=7.4 Hz, 1H).

The compounds in the following table were prepared according to the above procedure using the appropriate starting materials and modifications.

| Name | Structure | m/z |
|---|---|---|
| tert-butyl 4-((4-((2',3'-dihydrospiro[cyclopropane-1,1'-inden]-2-yl)carbamoyl)piperidin-1-yl)methyl)benzoate | 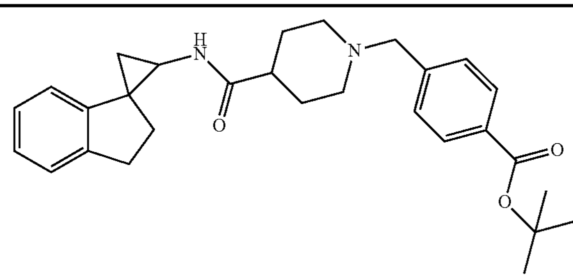 | 461 |

The compounds in the following table were prepared according to the above procedure using the appropriate starting materials and modifications.

| Name | Structure | m/z |
|---|---|---|
| tert-butyl 4-((4-(((2',3'-dihydrospiro[cyclopropane-1,1'-inden]-2-yl)amino)methyl)piperidin-1-yl)methyl)benzoate | 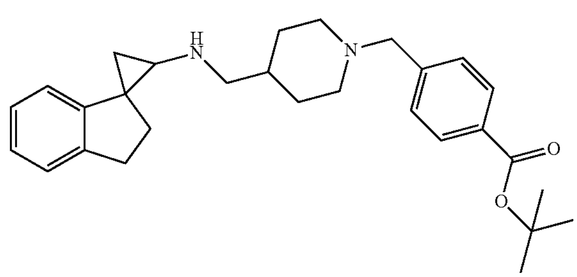 [SMILES: CC(C)(C)OC(=O)c1ccc(CN2CCC(CNC3CC34CCc3ccccc34)CC2)cc1] | 447 |

Example 107

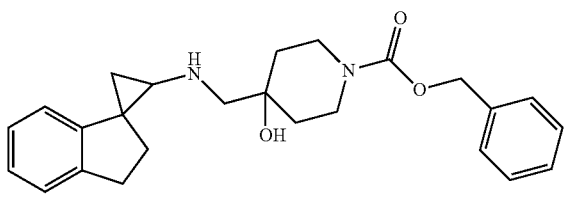 [SMILES: O=C(OCc1ccccc1)N1CCC(O)(CNC2CC23CCc2ccccc23)CC1]

Benzyl 4-(((2',3'-dihydrospiro[cyclopropane-1,1'-inden]-2-yl)amino)methyl)-4-hydroxypiperidine-1-carboxylate Step 1:

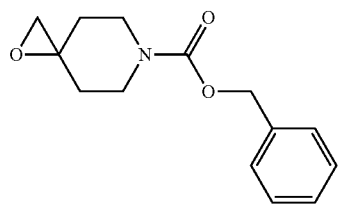 [SMILES: O=C(OCc1ccccc1)N1CCC2(CC1)CO2]

Benzyl 1-oxa-6-azaspiro[2.5]octane-6-carboxylate

To a mixture of iodo-trimethyl-oxo-sulfane (1.24 g, 5.65 mmol) in DMSO (10 mL) was added NaH (617 mg, 15.43 mmol) at 20° C. The mixture was stirred at 20° C. for 10 min. Benzyl 4-oxopiperidine-1-carboxylate (500 mg, 2.14 mmol) was added to the mixture. The mixture was stirred at 20° C. for 3 h. LCMS showed the reaction was completed. The mixture was poured into water (20 mL) and extracted with EtOAc (30 mL*3). The combined organic layer was dried over $Na_2SO_4$, filtered, and concentrated under vacuum to afford crude benzyl 1-oxa-6-azaspiro[2.5]octane-6-carboxylate (900 mg). LCMS m/z 248 [M+H]$^+$.

Step 2:

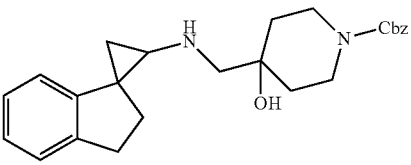 [SMILES: O=C(OCc1ccccc1)N1CCC(O)(CNC2CC23CCc2ccccc23)CC1]

Benzyl 4-hydroxy-4-[(spiro[cyclopropane-2,1'-indane]-1-ylamino)methyl]piperidine-1-carboxylate A mixture of benzyl 1-oxa-6-azaspiro[2.5]octane-6-carboxylate (560 mg, 2.26 mmol) and spiro[cyclopropane-2,1'-indane]-1-amine (360 mg, 2.26 mmol) in EtOH (30 mL) was stirred at 78° C. for 16 h. LCMS showed the reaction was complete. The mixture was then concentrated under vacuum and the residue purified by Prep-HPLC (Column:Phenomenex Synergi C18 150*30 mm*4 um. Method: 20-50-8 min. A: $H_2O$+0.05% HCl B: MeCN. Flow Rate (ml/min): 30) to afford benzyl 4-hydroxy-4-[(spiro[cyclopropane-2,1'-indane]-1-ylamino)methyl]piperidine-1-carboxylate (50, 0.122 mmol, 5% yield) as a solid. LCMS m/z 407 [M+H]$^+$.

Example 108

Biochemical Assay for LSD1 Activity

LSD1 demethylase reactions were carried out in 50 mM HEPES pH 7.4, 100 mM NaCl, 1 mM DTT, 0.01% Tween-20, and 0.1 mg/mL BSA. All enzymatic reactions were performed for either 15 or 50 minutes at room temperature in a 10-μL volume. Five microliters of 800 nM biotinylated H3K4me1 peptide solution was added to each well of a black 384 well Proxiplate containing 80 nL compound (final concentration of 0.8% DMSO). Reactions were initiated by the addition of a mixture containing 20 nM LSD1 and 20 nM FAD (5 μL). Enzyme activity was stopped by the addition of 5 μL of high salt buffer consisting of 50 mM HEPES pH 7.4, 1.5 M NaCl, 1 mM DTT, 0.01% Tween-20, and 0.1 mg/mL BSA. Capture of the product peptide by the anti-H3K4me0 antibody and Streptavidin APC was allowed to proceed for 60 mM at room temperature before measuring the TR-FRET signal. Europium-labeled antibody and Streptavidin APC were used at final concentrations of 0.003 nM and 100 nM, respectively (total assay volume of 20 μL). Plates were read on a Perkin Elmer EnVision. Percent inhibition was calculated using Max (no inhibitor) and Min (quenched with stop buffer) controls and inhibition curves plotted to determine $IC_{50}$ values.

| Example | Structure | IC50 T15 (μM) | IC50 T50 (μM) |
|---|---|---|---|
| 1 | 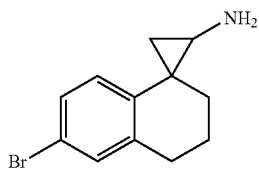 | | |

-continued

| Example | Structure | IC50 T15 (μM) | IC50 T50 (μM) |
|---|---|---|---|
| 2 | 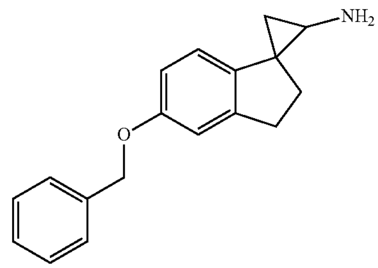 [SMILES: NC1CC12CCc1cc(OCc3ccccc3)ccc12] | 10++ | 6.83 |
| 3 | 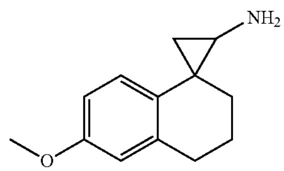 | 6.06 | 2.98 |
| 4 | 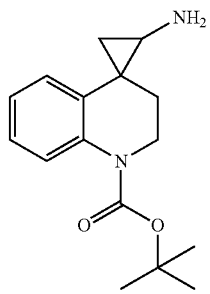 [SMILES: CC(C)(C)OC(=O)N1CCC2(CC2N)c2ccccc21] | 10++ | 4.26 |
| 5 | 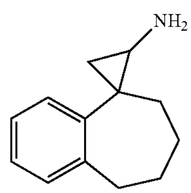 [SMILES: NC1CC12CCCCc1ccccc12] | 10++ | 10++ |
| 6 | 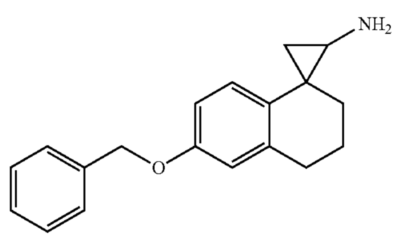 [SMILES: NC1CC12CCCc1cc(OCc3ccccc3)ccc12] | 9.3 | 5.03 |
| 7 | 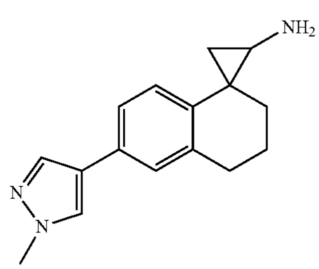 [SMILES: Cn1cc(-c2ccc3c(c2)CCCC32CC2N)cn1] | 10++ | 10++ |
| 8 | 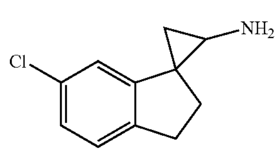 [SMILES: NC1CC12CCc1ccc(Cl)cc12] | 0.107 | 0.0542 |

-continued

| Example | Structure | IC50 T15 (μM) | IC50 T50 (μM) |
|---|---|---|---|
| 9 | 4-chloro-indane with cyclopropyl-NH₂ | 6.7++ | 6.08++ |
| 10 | Boc-piperidine-O-indane with cyclopropyl-NH₂ | 76.8++ | 43.4 |
| 11 | methyl-cyclopropyl-NH₂ tetrahydronaphthalene | 4.6 | 3.73 |
| 12 | 7-chloro tetrahydronaphthalene with cyclopropyl-NH₂ | 1.32 | 0.952 |
| 13 | 6-bromo indane with cyclopropyl-NH₂ | 0.0672 | 0.0386 |
| 15 | 6-cyano tetrahydronaphthalene with cyclopropyl-NH₂ (Single diastereomer) | | 5.57 |
| 16 | 6-cyano tetrahydronaphthalene with cyclopropyl-NH₂ (Single diastereomer) | 3.16 | 1.25 |
| 17 | 6-fluoro indane with cyclopropyl-NH₂ | 0.218 | 0.115 |

-continued
| Example | Structure | IC50 T15 (μM) | IC50 T50 (μM) |
|---|---|---|---|
| 18 | 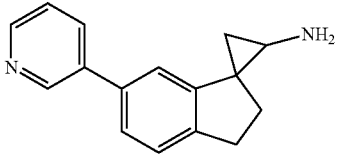 [SMILES: NC1CC12CCc1ccc(-c3cccnc3)cc12] | 4.76 | 3.66 |
| 19 | 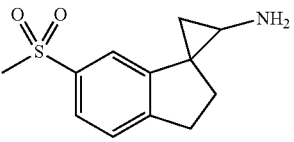 [SMILES: CS(=O)(=O)c1ccc2c(c1)C1(CC2)CC1N] | 2.37 | 1.36 |
| 20 | 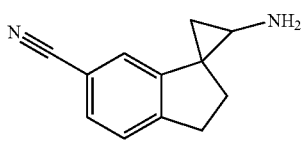 | 0.25 | 0.117 |
| 21 | 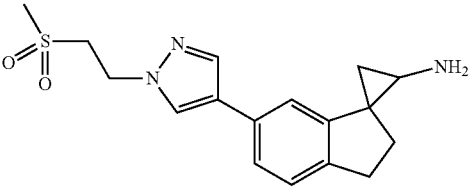 [SMILES: CS(=O)(=O)CCn1cc(-c2ccc3c(c2)C2(CC3)CC2N)cn1] | | 80++ |
| 22 | 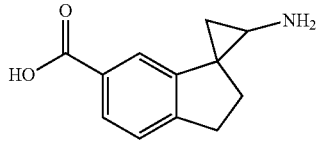 [SMILES: NC1CC12CCc1ccc(C(=O)O)cc12] | 16.1 | 8.32 |
| 23 | 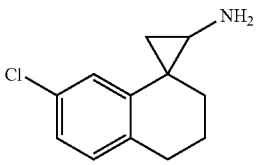 [SMILES: NC1CC12CCCc1ccc(Cl)cc12] | 1.09 | 0.871 |
| 24 | 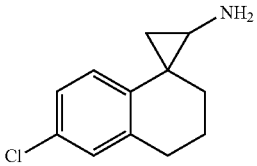 [SMILES: NC1CC12CCCc1cc(Cl)ccc12] | 1.32 | 0.952 |
| 25 | 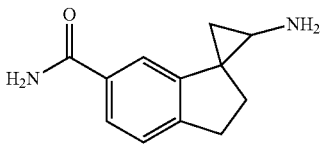 | 2.4 | 1.06 |
| 26 | 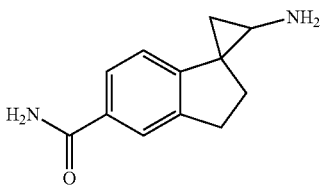 [SMILES: NC(=O)c1ccc2c(c1)CCC21CC1N] | 1.84 | 1.15 |

-continued

| Example | Structure | IC50 T15 (μM) | IC50 T50 (μM) |
|---|---|---|---|
| 27 | 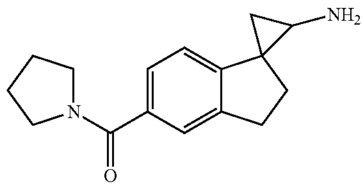 [SMILES: NC1CC12CCc1cc(C(=O)N3CCCC3)ccc12] | 14.2 | 7.7 |
| 28 | 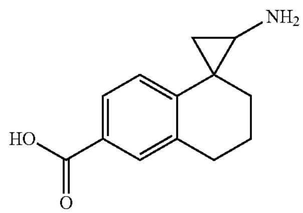 [SMILES: NC1CC12CCCc1cc(C(=O)O)ccc12] | 80++ | 80++ |
| 29 | single diastereomer | 6.82 | 4.36 |
| 30 | single diastereomer (above) | 0.538 | 0.471 |
| 31 | 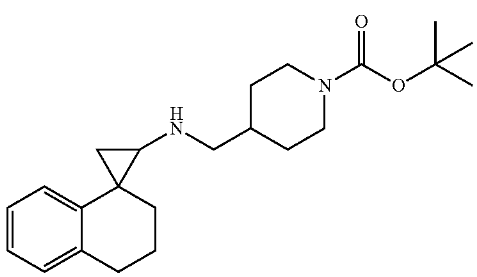 [SMILES: CC(C)(C)OC(=O)N1CCC(CNC2CC23CCCc2ccccc23)CC1] | 0.295 | 0.203 |
| 32 | 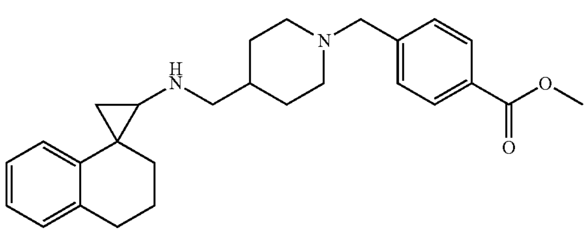 [SMILES: COC(=O)c1ccc(CN2CCC(CNC3CC34CCCc3ccccc34)CC2)cc1] | 0.101 | 0.142 |
| 33 | 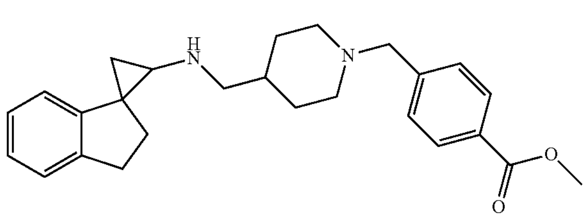 [SMILES: COC(=O)c1ccc(CN2CCC(CNC3CC34CCc3ccccc34)CC2)cc1] | 0.0122 | 0.0148 |

-continued
| Example | Structure | IC50 T15 (μM) | IC50 T50 (μM) |
|---|---|---|---|
| 34 | 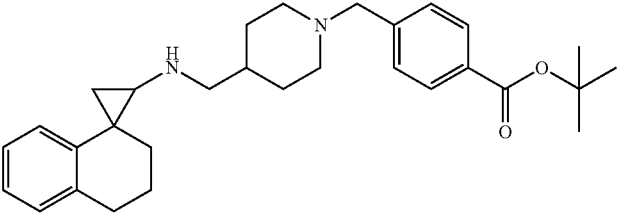 [SMILES: CC(C)(C)OC(=O)c1ccc(CN2CCC(CNC3CC34CCCc3ccccc34)CC2)cc1] | 0.343 | 0.366 |
| 35 | 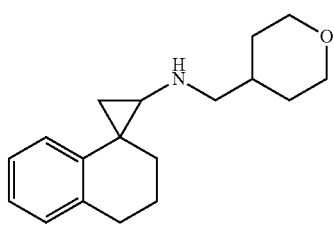 [SMILES: c1ccc2c(c1)CCCC21CC1NCC1CCOCC1] | 0.037 | 0.0485 |
| 36 | 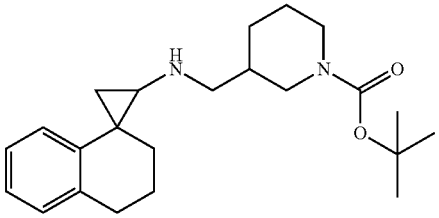 [SMILES: CC(C)(C)OC(=O)N1CCCC(CNC2CC23CCCc2ccccc23)C1] | 0.398 | 0.273 |
| 37 | 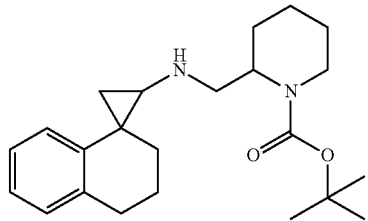 [SMILES: CC(C)(C)OC(=O)N1CCCCC1CNC1CC12CCCc1ccccc12] | 10++ | 5.67 |
| 38 | 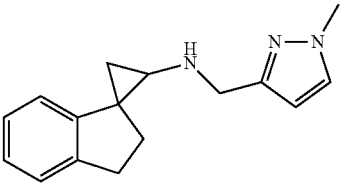 [SMILES: Cn1ccc(CNC2CC23CCc2ccccc23)n1] | 0.0937 | 0.0462 |
| 39 | 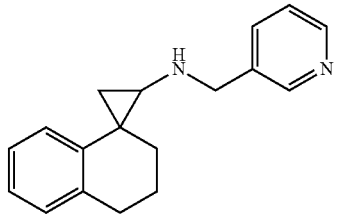 [SMILES: c1cncc(CNC2CC23CCCc2ccccc23)c1] | 0.0995 | 0.0941 |
| 40 | 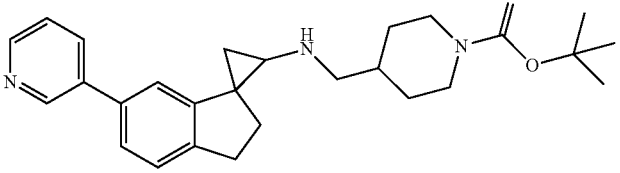 | 0.394 | 0.255 |

-continued

| Example | Structure | IC50 T15 (μM) | IC50 T50 (μM) |
|---|---|---|---|
| 41 | 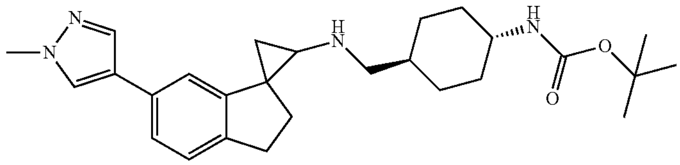 [SMILES: Cn1cc(-c2ccc3c(c2)C2(CC3)CC2NC[C@H]2CC[C@H](NC(=O)OC(C)(C)C)CC2)cn1] | 0.55 | 0.366 |
| 42 | 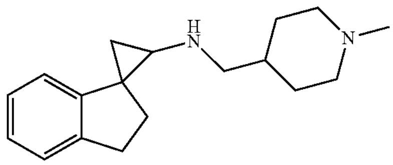 [SMILES: CN1CCC(CNC2CC23CCc2ccccc23)CC1] | 0.0251 | 0.021 |
| 43 | 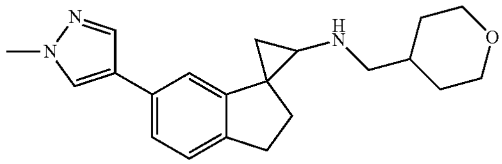 [SMILES: Cn1cc(-c2ccc3c(c2)C2(CC3)CC2NCC2CCOCC2)cn1] | 0.393 | 0.205 |
| 44 | 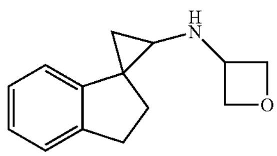 [SMILES: c1ccc2c(c1)CCC21CC1NC1COC1] | 0.273 | 0.15 |
| 45 | 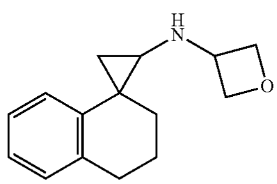 [SMILES: c1ccc2c(c1)CCCC21CC1NC1COC1] | 2.82 | 1.89 |
| 46 | 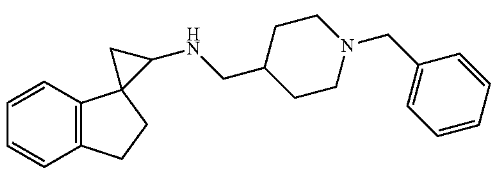 [SMILES: c1ccc(CN2CCC(CNC3CC34CCc3ccccc34)CC2)cc1] | | |
| 47 | 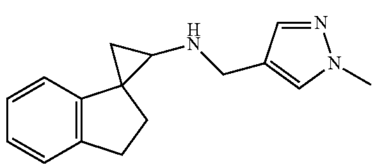 [SMILES: Cn1cc(CNC2CC23CCc2ccccc23)cn1] | 0.0813 | 0.0555 |
| 48 | 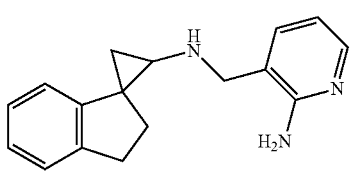 [SMILES: Nc1ncccc1CNC1CC12CCc1ccccc12] | 0.0436++ | 0.0472++ |
| 49 | 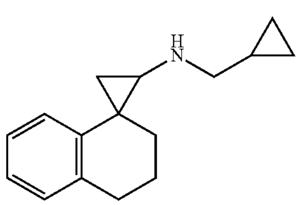 [SMILES: c1ccc2c(c1)CCCC21CC1NCC1CC1] | 0.323 | 0.26 |

-continued
| Example | Structure | IC50 T15 (μM) | IC50 T50 (μM) |
|---|---|---|---|
| 50 | 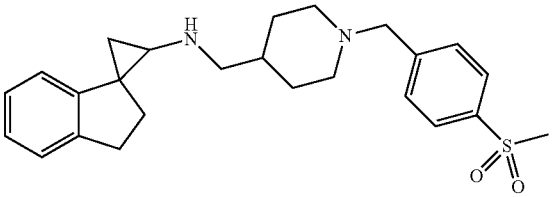<br>single diastereomer | 0.050 | 0.0474++ |
| 51 | 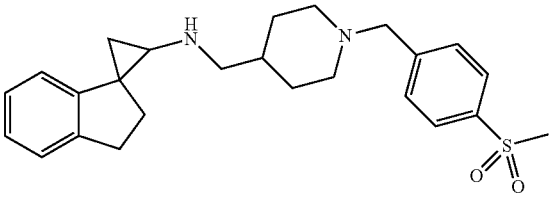<br>single diastereomer | 0.0647 | 0.0567 |
| 52 | 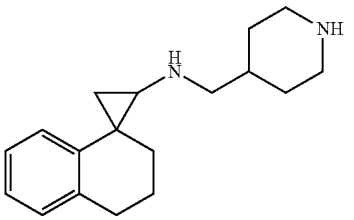 [SMILES: c1ccc2c(c1)CCCC21CC1NCC1CCNCC1] | 0.0818 | 0.0654 |
| 53 | 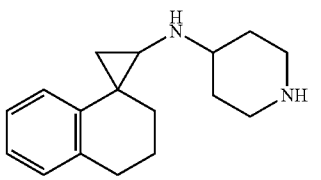 | 0.0384 | 0.0524 |
| 54 | 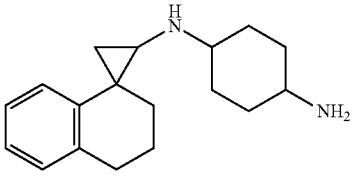 [SMILES: NC1CCC(NC2CC23CCCc2ccccc23)CC1] | 0.116 | 0.165 |
| 55 | 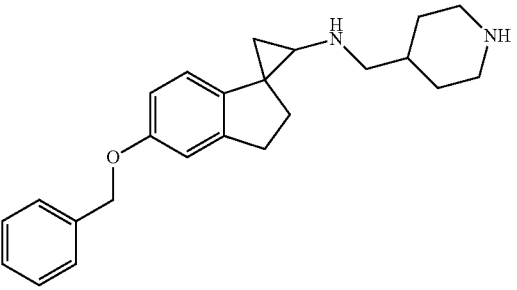 [SMILES: c1ccc(COc2ccc3c(c2)CCC32CC2NCC2CCNCC2)cc1] | 0.103 | 0.107 |

-continued
| Example | Structure | IC50 T15 (μM) | IC50 T50 (μM) |
|---|---|---|---|
| 56 | 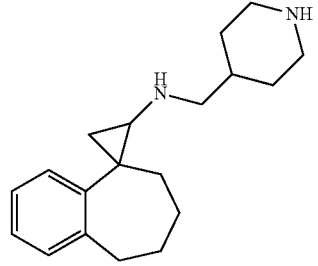 [SMILES: c1ccc2c(c1)CCCCC21CC1NCC1CCNCC1] | 1.0++ | 1.0++ |
| 57 | 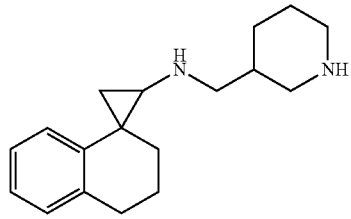 [SMILES: c1ccc2c(c1)CCCC21CC1NCC1CCCNC1] | 0.144 | 0.134 |
| 58 | 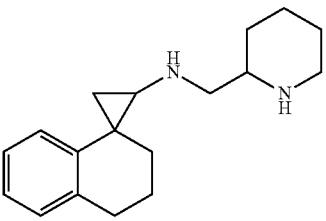 [SMILES: c1ccc2c(c1)CCCC21CC1NCC1CCCCN1] | 1.0++ | 0.674 |
| 59 | 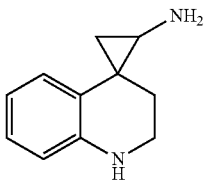 [SMILES: NC1CC12CCNc1ccccc12] | 10++ | 10++ |
| 60 | 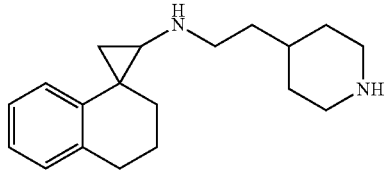 [SMILES: c1ccc2c(c1)CCCC21CC1NCCC1CCNCC1] | 0.128 | 0.0877 |
| 61 | 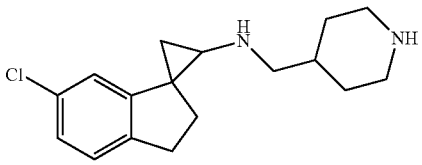 [SMILES: Clc1ccc2c(c1)C1(CC2)CC1NCC1CCNCC1] | 0.0489 | 0.0556 |
| 62 | 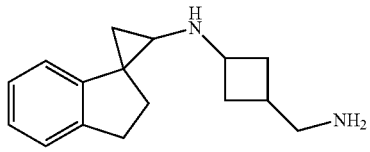 [SMILES: NCC1CC(NC2CC23CCc2ccccc23)C1] | 0.0318 | 0.0193 |

-continued

| Example | Structure | IC50 T15 (μM) | IC50 T50 (μM) |
|---|---|---|---|
| 63 | 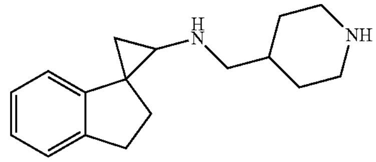 [SMILES: c1ccc2c(c1)CCC21CC1NCC1CCNCC1] | 0.0328 | 0.0675 |
| 64 | 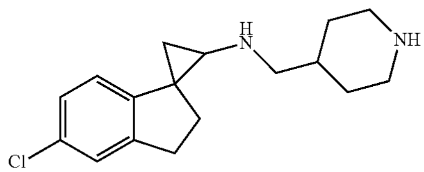 [SMILES: Clc1ccc2c(c1)CCC21CC1NCC1CCNCC1] | 0.0407 | 0.0475 |
| 65 | 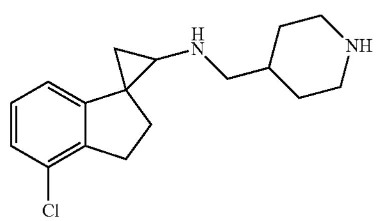 [SMILES: Clc1cccc2c1CCC21CC1NCC1CCNCC1] | 0.0887 | 0.0748 |
| 66 | 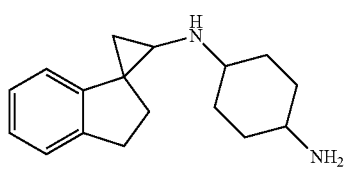 [SMILES: NC1CCC(NC2CC23CCc2ccccc23)CC1] | 0.0851 | 0.0938 |
| 67 | 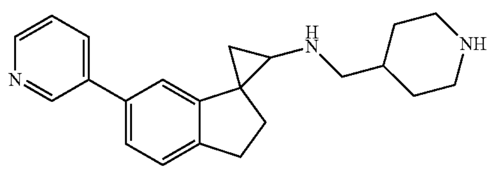 [SMILES: c1cncc(-c2ccc3c(c2)C2(CC3)CC2NCC2CCNCC2)c1] | 0.0607 | 0.0538 |
| 68 | 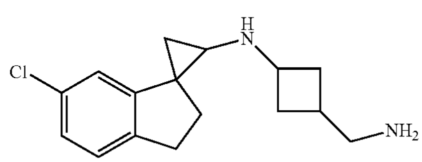 [SMILES: NCC1CC(NC2CC23CCc2ccc(Cl)cc23)C1] | 0.0483 | 0.0483 |
| 69 | 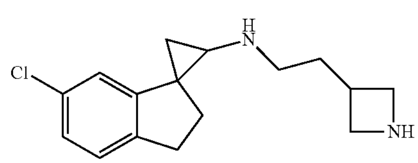 [SMILES: Clc1ccc2c(c1)C1(CC2)CC1NCCC1CNC1] | 0.0468 | 0.0382 |
| 70 | 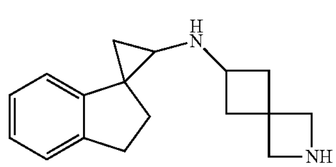 [SMILES: c1ccc2c(c1)CCC21CC1NC1CC2(CNC2)C1] | 0.0306 | 0.0322 |
| 71 | 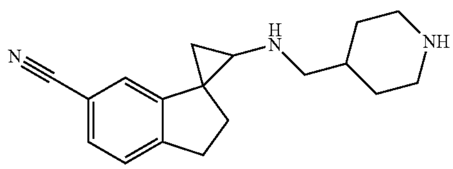 [SMILES: N#Cc1ccc2c(c1)C1(CC2)CC1NCC1CCNCC1] | 0.044 | 0.0494 |

-continued

| Example | Structure | IC50 T15 (μM) | IC50 T50 (μM) |
| --- | --- | --- | --- |
| 72 | 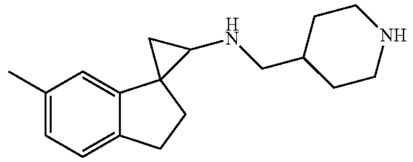 [SMILES: Cc1ccc2c(c1)C1(CC2)CC1NCC1CCNCC1] | 0.0344 | 0.0364 |
| 73 | 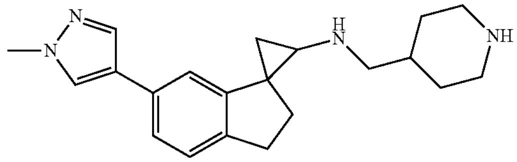 [SMILES: Cn1cc(-c2ccc3c(c2)C2(CC3)CC2NCC2CCNCC2)cn1] | 0.084 | 0.074 |
| 74 | 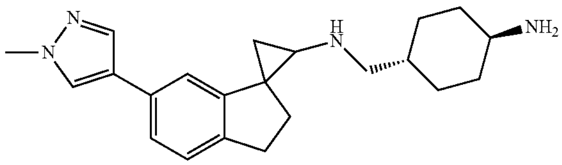 [SMILES: Cn1cc(-c2ccc3c(c2)C2(CC3)CC2NC[C@H]2CC[C@H](N)CC2)cn1] | | |
| 75 | 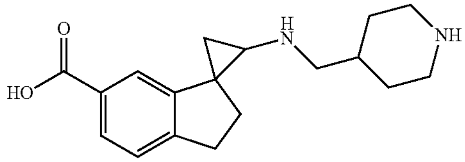 [SMILES: O=C(O)c1ccc2c(c1)C1(CC2)CC1NCC1CCNCC1] | 1.99++ | 1.61++ |
| 76 | 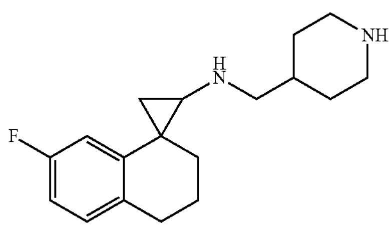 [SMILES: Fc1ccc2c(c1)C1(CCC2)CC1NCC1CCNCC1] | 0.288 | 0.448 |
| 77 | single diastereomer | 0.0575 | 0.0673 |
| 78 | single diastereomer | 0.081 | 0.12 |
| 79 | single diastereomer | 0.0646 | 0.0931 |

-continued
| Example | Structure | IC50 T15 (μM) | IC50 T50 (μM) |
|---|---|---|---|
| 80 | 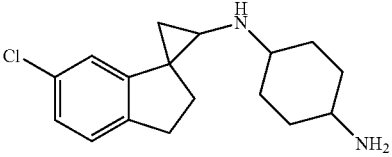<br>single diastereomer | 0.0896 | 0.123 |
| 81 | 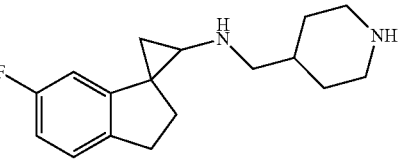<br>single diastereomer | 0.0584 | 0.0648 |
| 82 | 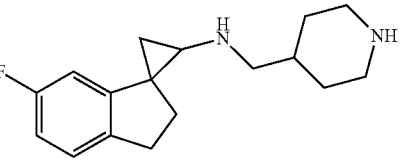<br>single diastereomer | 0.0576 | 0.073 |
| 83 | 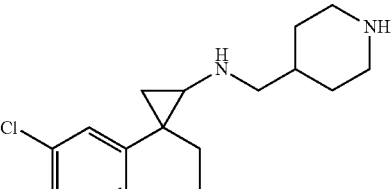<br>single diastereomer | 0.443 | 0.51 |
| 84 | 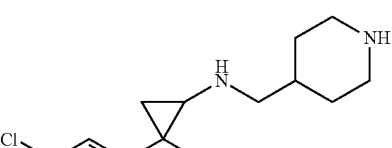<br>single diastereomer | 0.567++ | 0.615++ |
| 85 | 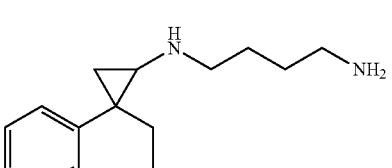 | 0.311 | 0.285 |
| 86 | 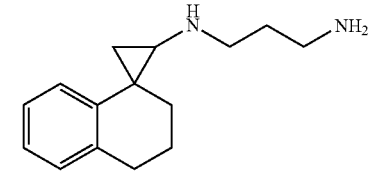 [SMILES: NCCCNC1CC12CCCc1ccccc12] | 0.253 | 0.199 |

-continued
| Example | Structure | IC50 T15 (µM) | IC50 T50 (µM) |
|---|---|---|---|
| 87 | 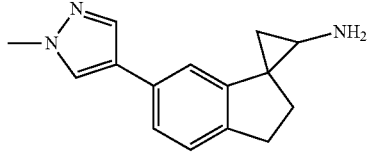 single diastereomer | 7.37 | 3.04 |
| 88 | 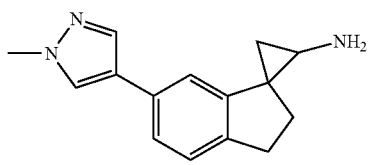 single diastereomer | 80++ | 80++ |
| 89 | 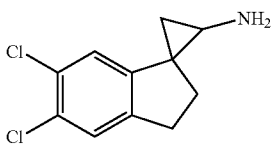 [SMILES: NC1CC12CCc1cc(Cl)c(Cl)cc12] | 0.865 | 0.431 |
| 90 | 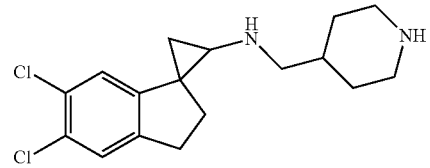 single diastereomer | 0.0294 | 0.0768 |
| 91 | 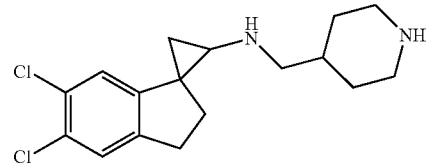 single diastereomer | 0.184 | 0.181 |
| 92 | 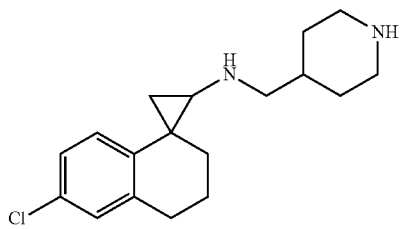 single diastereomer | 0.485 | 0.565 |
| 93 | 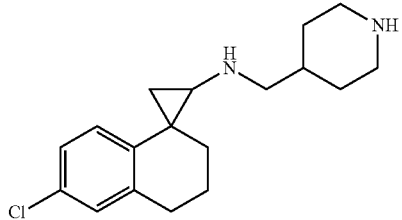 single diastereomer | 0.553++ | 0.556++ |

-continued

| Example | Structure | IC50 T15 (μM) | IC50 T50 (μM) |
|---|---|---|---|
| 94 | single diastereomer | 0.312 | 0.366 |
| 95 | single diastereomer | 1.49 | 1.68 |
| 96 | single diastereomer | 0.688 | 0.671 |
| 97 | single diastereomer | 5.02 | |
| 98 | 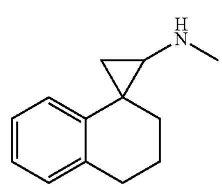 | 1.11 | 0.628 |
| 99 | 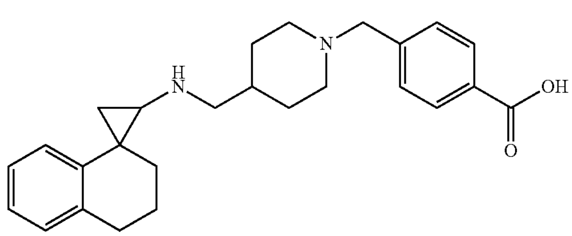 [SMILES: O=C(O)c1ccc(CN2CCC(CNC3CC34CCCc3ccccc34)CC2)cc1] | 0.151 | 0.148 |

-continued

| Example | Structure | IC50 T15 (μM) | IC50 T50 (μM) |
| --- | --- | --- | --- |
| 100 | 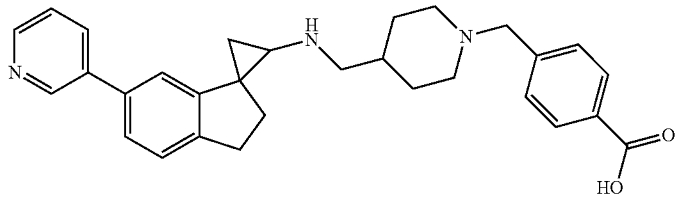 [SMILES: O=C(O)c1ccc(CN2CCC(CNC3CC34CCc3ccc(-c5cccnc5)cc34)CC2)cc1] | 0.518 | 0.248 |
| 101 | 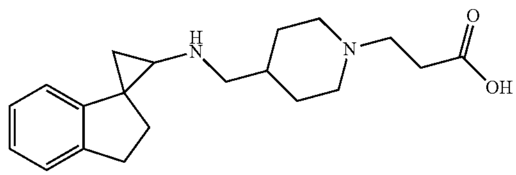 [SMILES: O=C(O)CCN1CCC(CNC2CC23CCc2ccccc23)CC1] | 0.381 | 0.18 |
| 102 | 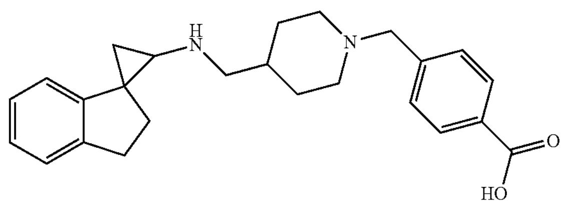 [SMILES: O=C(O)c1ccc(CN2CCC(CNC3CC34CCc3ccccc34)CC2)cc1] | 0.289 | 0.229 |
| 103 | 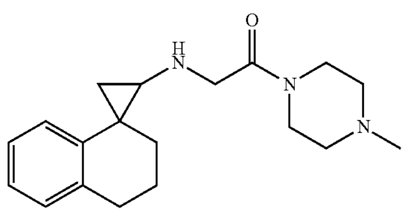 [SMILES: CN1CCN(C(=O)CNC2CC23CCCc2ccccc23)CC1] | 0.113 | 0.128 |
| 104 | 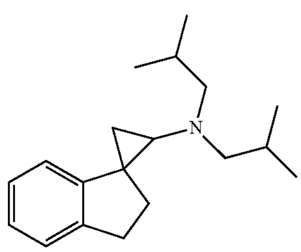 [SMILES: CC(C)CN(CC(C)C)C1CC12CCc1ccccc12] | 80++ | 80++ |
| 105 | 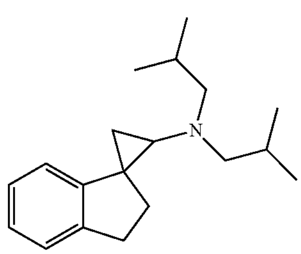 [SMILES: CC(C)CN(CC(C)C)C1CC12CCc1ccccc12] | 80++ | 47.9 |
| 106 | 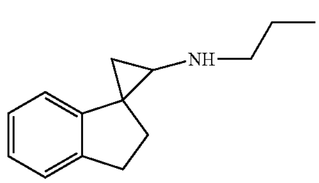 | 0.87 | 0.529 |

| Example | Structure | IC50 T15 (µM) | IC50 T50 (µM) |
|---|---|---|---|
| 107 | 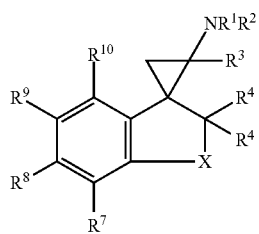 | 0.0309++ | 0.033++ |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula I:

$$I$$

wherein:
- X is, $-C(R^5)_2-$, $-(C(R^5)_2)_2-$, $-(C(R^5)_2)_3-$ or $-N(R^6)C(R^5)_2-$;
- $R^1$ is hydrogen, $C_{1-6}$alkyl, $C_{2-6}$alkenyl, $C_{2-6}$alkynyl, carbocyclyl or heterocyclyl, wherein any $C_{1-6}$alkyl, $C_{2-6}$alkenyl or $C_{2-6}$alkynyl of $R^1$ is optionally substituted with one or more $R^{a1}$ groups; and wherein any carbocyclyl or heterocyclyl of $R^1$ is optionally substituted with one or more $R^{a3}$ groups;
- $R^2$ is hydrogen or $C_{1-6}$alkyl;
- $R^3$ is hydrogen or $C_{1-6}$alkyl;
- each $R^4$ is independently selected from the group consisting of hydrogen, halogen and methyl;
- each $R^5$ is independently selected from the group consisting of hydrogen, halogen and methyl;
- $R^6$ is hydrogen, $C_{1-6}$alkyl or $-C(O)OR^{b1}$;
- $R^7$ is hydrogen, halo, $C_{1-6}$alkyl, $C_{2-6}$alkenyl, $C_{2-6}$alkynyl, heterocyclyl, $-OR^{c1}$, CN, $-C(O)-N(R^{c2})_2$, $-S(O)_2-R^{c2}$ or $-C(O)-OR^{c2}$, wherein any $C_{1-6}$alkyl, $C_{2-6}$alkenyl or $C_{2-6}$alkynyl of $R^7$ is optionally substituted with one or more $R^{c3}$ groups and wherein any heterocyclyl of $R^7$ is optionally substituted with one or more $R^{c4}$ groups;
- $R^8$ is hydrogen, halo, $C_{1-6}$alkyl, $C_{2-6}$alkenyl, $C_{2-6}$alkynyl, heterocyclyl, $-OR^{d1}$, CN, $-C(O)-N(R^{d2})_2$, $-S(O)_2-R^{d2}$ or $-C(O)-OR^{d2}$, wherein any $C_{1-6}$alkyl, $C_{2-6}$alkenyl or $C_{2-6}$alkynyl of $R^8$ is optionally substituted with one or more $R^{d3}$ groups and wherein any heterocyclyl of $R^8$ is optionally substituted with one or more $R^{d4}$ groups;
- $R^9$ is hydrogen, halo, $C_{1-6}$alkyl, $C_{2-6}$alkenyl, $C_{2-6}$alkynyl, heterocyclyl, $-OR^{e1}$, CN, $-C(O)-N(R^{e2})_2$, $-S(O)_2-R^{e2}$ or $-C(O)-OR^{e2}$, wherein any $C_{1-6}$alkyl, $C_{2-6}$alkenyl or $C_{2-6}$alkynyl of $R^9$ is optionally substituted with one or more $R^{e3}$ groups and wherein any heterocyclyl of $R^9$ is optionally substituted with one or more $R^{e4}$ groups;
- $R^{10}$ is hydrogen, halo, $C_{1-6}$alkyl, $C_{2-6}$alkenyl, $C_{2-6}$alkynyl, heterocyclyl, $-OR^{f1}$, CN, $-C(O)-N(R^{f2})_2$, $-S(O)_2-R^{f2}$ or $-C(O)-OR^{f2}$, wherein any $C_{1-6}$alkyl, $C_{2-6}$alkenyl or $C_{2-6}$alkynyl of $R^{10}$ is optionally substituted with one or more $R^{f3}$ groups and wherein any heterocyclyl of $R^{10}$ is optionally substituted with one or more $R^{f4}$ groups;
- each $R^{a1}$ is independently halo, oxo, $-N(R^{a3})_2$, carbocyclyl, or heterocyclyl, wherein any carbocyclyl or heterocyclyl of $R^{a1}$ is optionally substituted with one or more groups independently selected from the group consisting of halo, $C_{1-6}$alkyl, $-N(R^{a3})_2$, $-OR^{a3}$, $-C(O)OR^{a3}$, $-NR^{a3}C(O)OR^{a3}$, $-C_{1-6}$alkylphenyl and $-C_{1-6}$alkylC(O)OR^{a3} wherein the $-C_{1-6}$alkylphenyl is optionally substituted with one or more groups independently selected from the group consisting of halogen, $C_{1-6}$alkyl, $-N(R^{a3})_2$, $-C(O)OR^{a3}$ and $-S(O)_2-R^{a3}$;
- each $R^{a2}$ is independently halo, $-N(R^{a3})_2$ or $C_{1-6}$alkyl, wherein any $C_{1-6}$alkyl of $R^{a2}$ is optionally substituted with one or more $-N(R^{a3})_2$;
- each $R^{a3}$ is independently hydrogen, $C_{1-6}$alkyl or $-C_{1-6}$alkylphenyl;
- $R^{b1}$ is $C_{1-6}$alkyl or $-C_{1-6}$alkylphenyl;
- $R^{c1}$ is hydrogen, $C_{1-6}$alkyl or heterocyclyl, wherein any alkyl of $R^{c1}$ is optionally substituted with one or more halo or phenyl, and wherein any heterocyclyl of $R^{c1}$ is optionally substituted with one or more $C_{1-6}$alkyl or $-C(=O)OC_{1-6}$alkyl;
- each $R^{c2}$ is independently selected from the group consisting of hydrogen, $C_{1-6}$alkyl, $C_{2-6}$alkenyl and $C_{2-6}$alkynyl, or two $R^{c2}$ groups together with the nitrogen to which they are attached form a 3-7 membered heterocyclyl;
- each $R^{c3}$ is independently selected from the group consisting of $-S(O)_2-R^{c2}$ and halo;
- each $R^{c4}$ is independently selected from the group consisting of $C_{1-6}$alkyl and $C_{1-6}$haloalkyl, wherein any $C_{1-6}$alkyl of $R^{c4}$ is optionally substituted with one or more groups independently selected from the group consisting of $C_{1-6}$alkyl, halo and $-S(O)_2-R^{c2}$;
- $R^{d1}$ is hydrogen, $C_{1-6}$alkyl or heterocyclyl, wherein any alkyl of $R^{d1}$ is optionally substituted with one or more halo or phenyl, and wherein any heterocyclyl of $R^{d1}$ is optionally substituted with one or more $C_{1-6}$alkyl or $-C(=O)OC_{1-6}$alkyl;
- each $R^{d2}$ is independently selected from the group consisting of hydrogen, $C_{1-6}$alkyl, $C_{2-6}$alkenyl and $C_{2-6}$alkynyl, or two $R^{d2}$ groups together with the nitrogen to which they are attached form a 3-7 membered heterocyclyl;

each $R^{d3}$ is independently selected from the group consisting of —S(O)$_2$—$R^{d2}$ and halo;

each $R^{d4}$ is independently selected from the group consisting of $C_{1-6}$alkyl and $C_{1-6}$haloalkyl, wherein any $C_{1-6}$alkyl of $R^{d4}$ is optionally substituted with one or more groups independently selected from the group consisting of $C_{1-6}$alkyl, halo and —S(O)$_2$—$R^{d2}$;

$R^{e1}$ is hydrogen, $C_{1-6}$alkyl or heterocyclyl, wherein any alkyl of $R^{e1}$ is optionally substituted with one or more halo or phenyl, and wherein any heterocyclyl of $R^{e1}$ is optionally substituted with one or more $C_{1-6}$alkyl or —C(=O)OC$_{1-6}$alkyl;

each $R^{e2}$ is independently selected from the group consisting of hydrogen, $C_{1-6}$alkyl, $C_{2-6}$alkenyl and $C_{2-6}$alkynyl, or two $R^{e2}$ groups together with the nitrogen to which they are attached form a 3-7 membered heterocyclyl;

each $R^{e3}$ is independently selected from the group consisting of —S(O)$_2$—$R^{e2}$ and halo;

each $R^{e4}$ is independently selected from the group consisting of $C_{1-6}$alkyl and $C_{1-6}$haloalkyl, wherein any $C_{1-6}$alkyl of $R^{e4}$ is optionally substituted with one or more groups independently selected from the group consisting of $C_{1-6}$alkyl, halo and —S(O)$_2$—$R^{e2}$;

$R^{f1}$ is hydrogen, $C_{1-6}$alkyl or heterocyclyl, wherein any alkyl of $R^{f1}$ is optionally substituted with one or more halo or phenyl, and wherein any heterocyclyl of $R^{f1}$ is optionally substituted with one or more $C_{1-6}$alkyl or —C(=O)OC$_{1-6}$alkyl;

each $R^{f2}$ is independently selected from the group consisting of hydrogen, $C_{1-6}$alkyl, $C_{2-6}$alkenyl and $C_{2-6}$alkynyl, or two $R^{f2}$ groups together with the nitrogen to which they are attached form a 3-7 membered heterocyclyl;

each $R^{f3}$ is independently selected from the group consisting of —S(O)$_2$—$R^{f2}$ and halo; and each $R^{f4}$ is independently selected from the group consisting of $C_{1-6}$alkyl and $C_{1-6}$haloalkyl, wherein any $C_{1-6}$alkyl of $R^{f4}$ is optionally substituted with one or more groups independently selected from the group consisting of $C_{1-6}$alkyl, halo and —S(O)$_2$—$R^{f2}$;

or a salt thereof;

provided the compound is not:

3',4'-dihydro-2'H-spiro[cyclopropane-1,1'-naphthalen]-2-amine;

4'-methyl-3',4'-dihydro-2'H-spiro[cyclopropane-1,1'-naphthalen]-2-amine;

7'-methoxy-3',4'-dihydro-2'H-spiro[cyclopropane-1,1'-naphthalen]-2-amine;

4',4'-dimethyl-3',4'-dihydro-2'H-spiro[cyclopropane-1,1'-naphthalen]-2-amine;

6'-methoxy-3',4'-dihydro-2'H-spiro[cyclopropane-1,1'-naphthalen]-2-amine;

2',3'-dihydrospiro[cyclopropane-1,1'-inden]-2-amine;

5'-fluoro-2',3'-dihydrospiro[cyclopropane-1,1'-inden]-2-amine;

6'-methyl-2',3'-dihydrospiro[cyclopropane-1,1'-inden]-2-amine;

4'-fluoro-2',3'-dihydrospiro[cyclopropane-1,1'-inden]-2-amine;

5'-chloro-2',3'-dihydrospiro[cyclopropane-1,1'-inden]-2-amine;

5'-bromo-2',3'-dihydrospiro[cyclopropane-1,1'-inden]-2-amine;

6'-methoxy-2',3'-dihydrospiro[cyclopropane-1,1'-inden]-2-amine; or 6,7,8,9-tetrahydrospiro[benzo[7]annulene-5,1'-cyclopropan]-2'-amine;

or a salt thereof.

2. The compound of claim 1, wherein X is —CH$_2$—, —CH$_2$CH$_2$— or —CH$_2$CH$_2$CH$_2$—.

3. The compound of claim 1, wherein the compound of formula I is a compound of formula Ia:

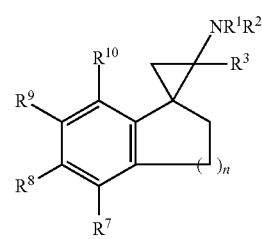

wherein n is 1, 2 or 3; or a salt thereof.

4. The compound of claim 1, wherein the compound of formula I is a compound of formula Ic, Id or Ie:

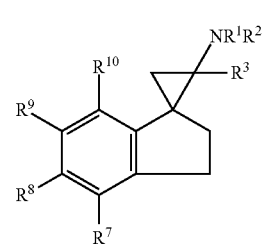

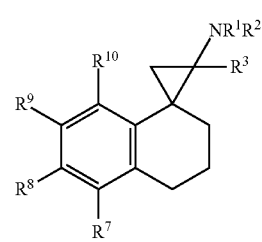

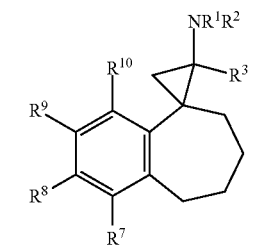

or a salt thereof.

5. The compound of claim 1, wherein the compound of formula I is a compound of formula Ib:

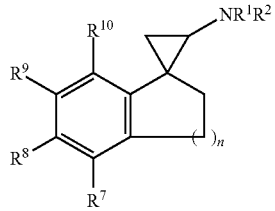

wherein n is 1, 2 or 3; or a salt thereof.

6. The compound of claim 1, wherein X is or —N(R⁶)C(R⁵)₂—.

7. The compound of claim 1, wherein R⁸ is hydrogen, halo, heteroaryl, —OR$^{d1}$, CN, —C(O)—N(R$^{d2}$)₂ or —C(O)—OR$^{d2}$, wherein any heteroaryl of R⁸ is optionally substituted with one or more R$^{d4}$ groups.

8. The compound of claim 1, wherein R⁸ is

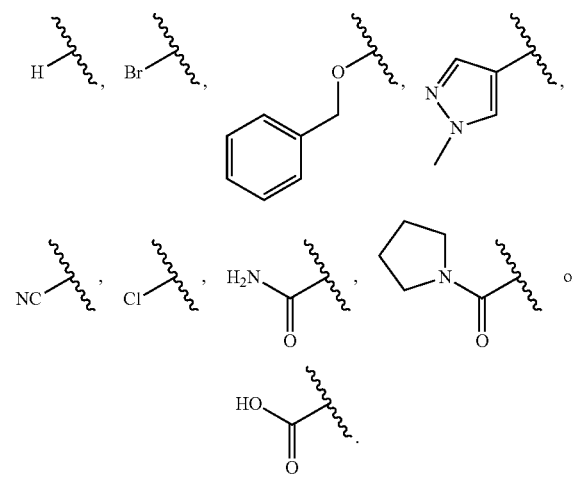

9. The compound of claim 1, wherein R⁹ is

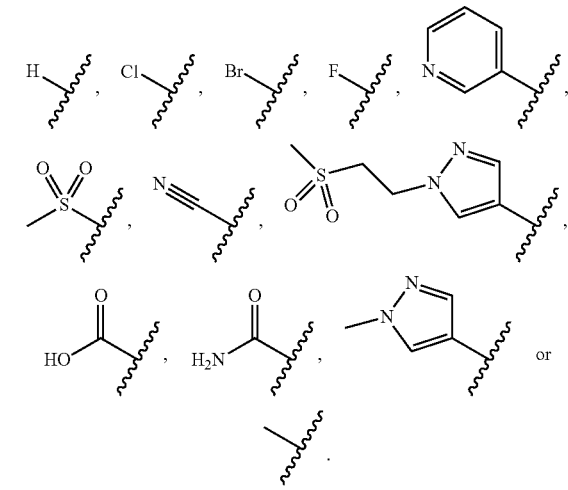

10. The compound of claim 1, wherein R¹⁰ is

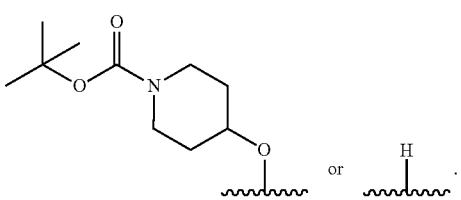

11. The compound of claim 1, wherein the compound of formula I is a compound of formula If:

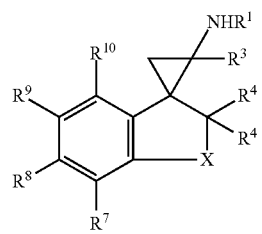

or a salt thereof.

12. The compound of claim 1, wherein R¹ is hydrogen,

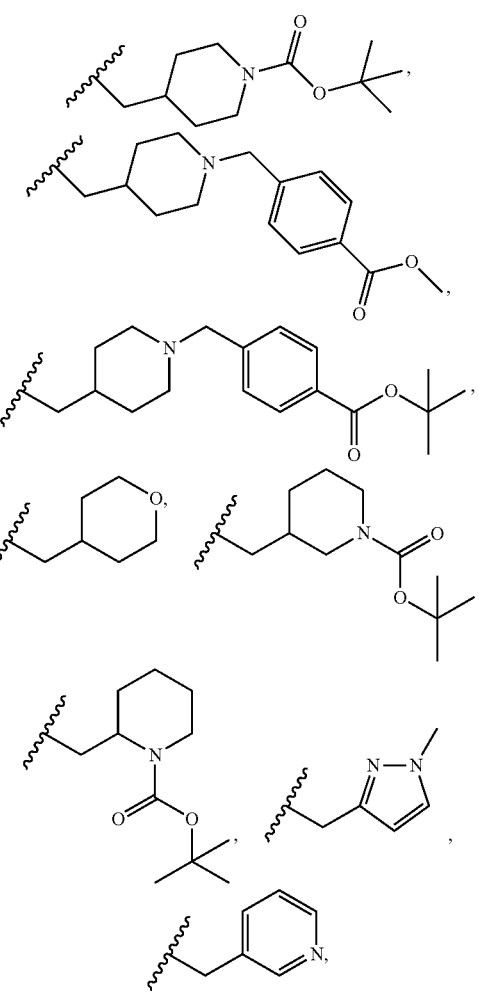

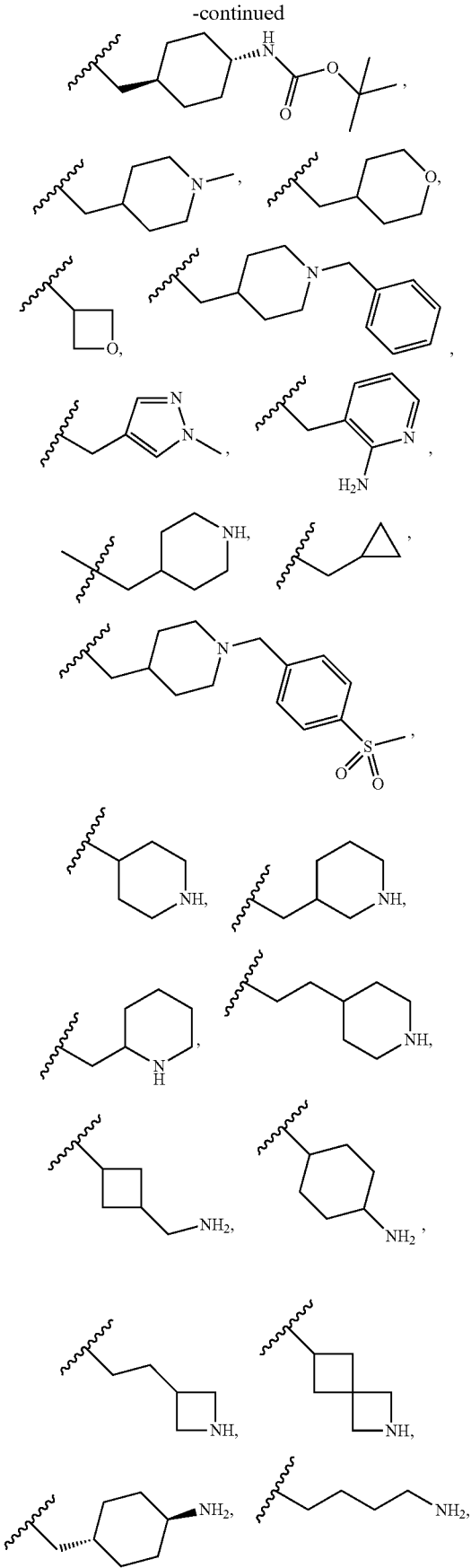
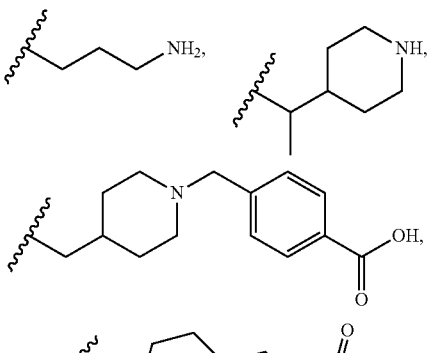
13. The compound of claim 1, wherein R¹ is
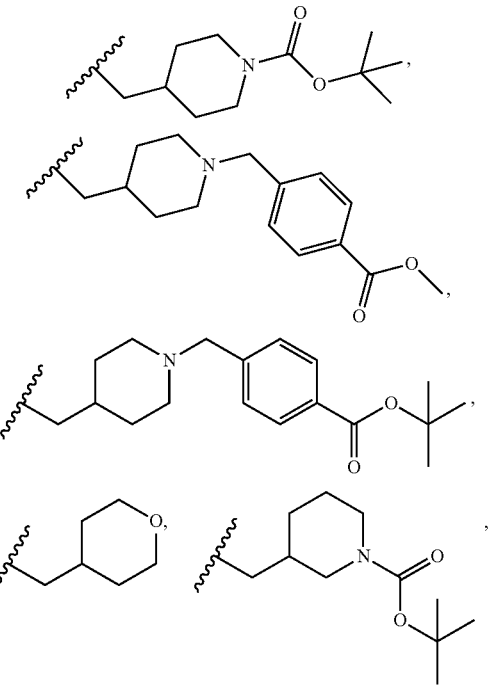

-continued
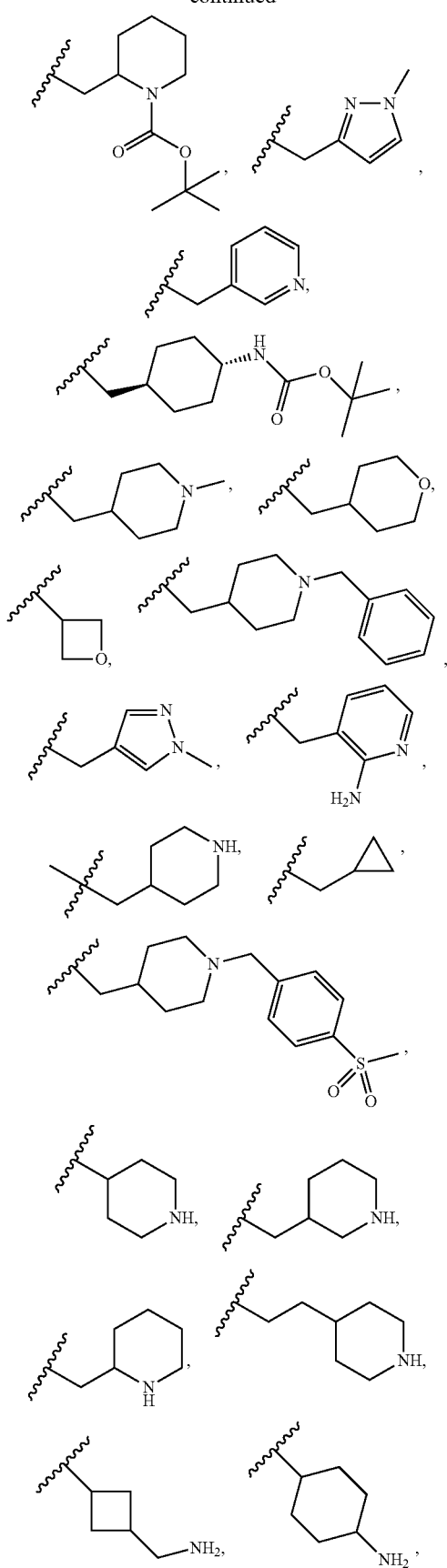
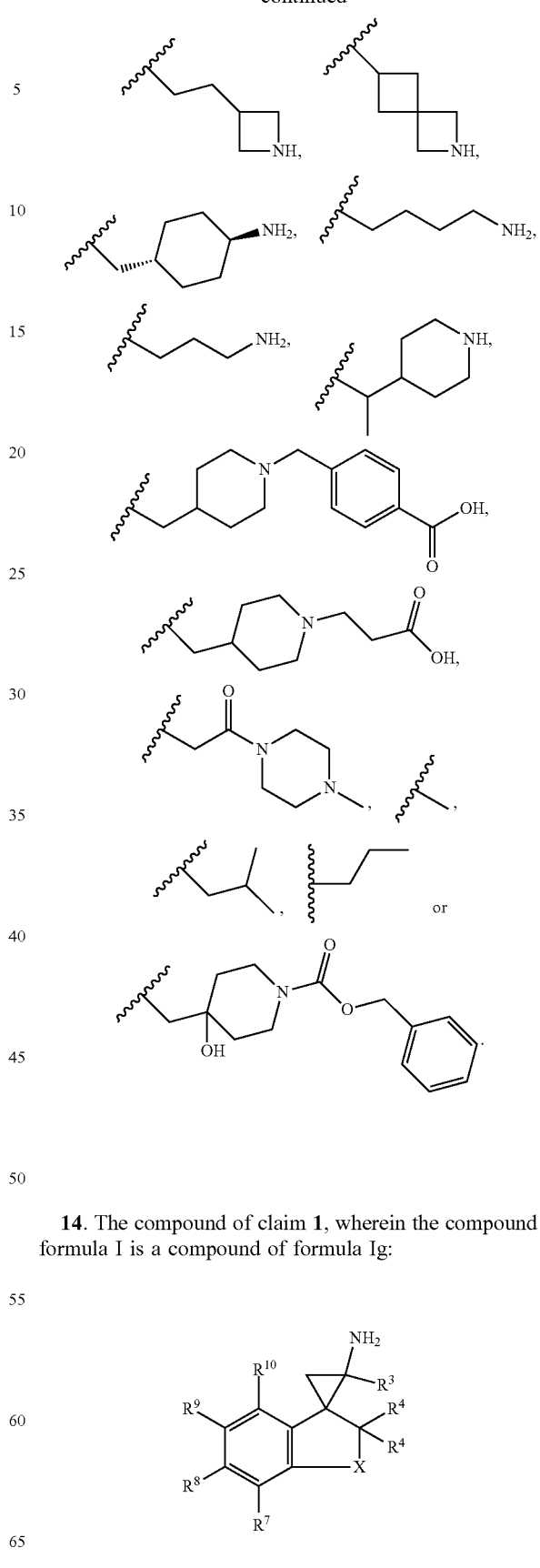
14. The compound of claim 1, wherein the compound of formula I is a compound of formula Ig:
Ig
or a salt thereof.

15. The compound of claim 1 which is:
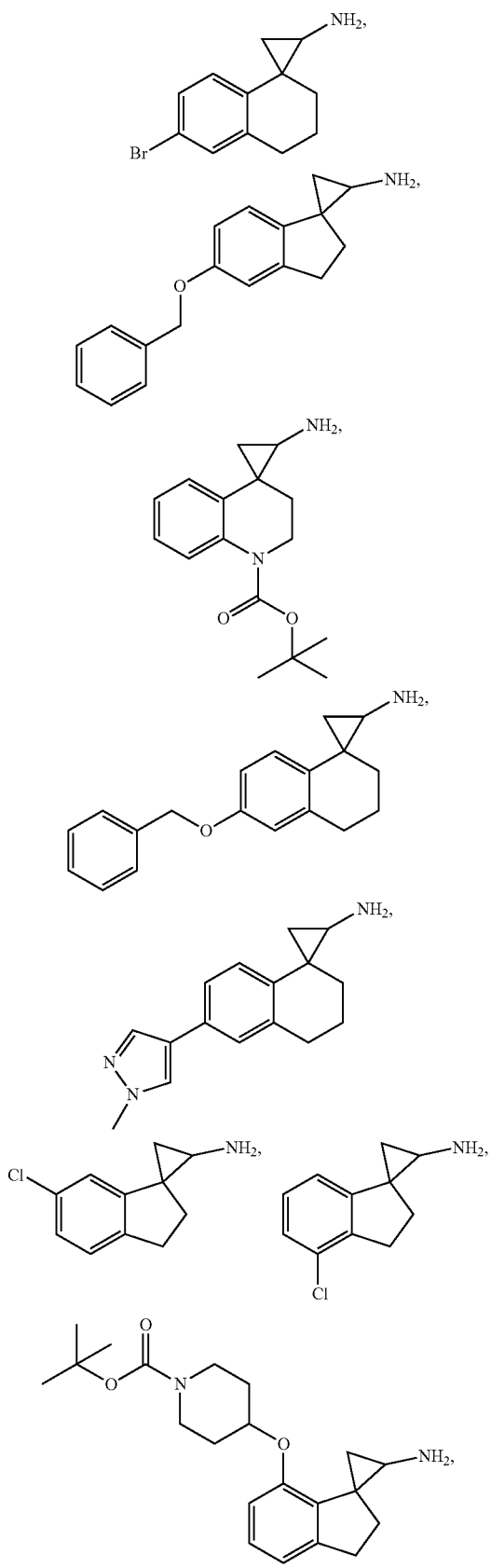
-continued
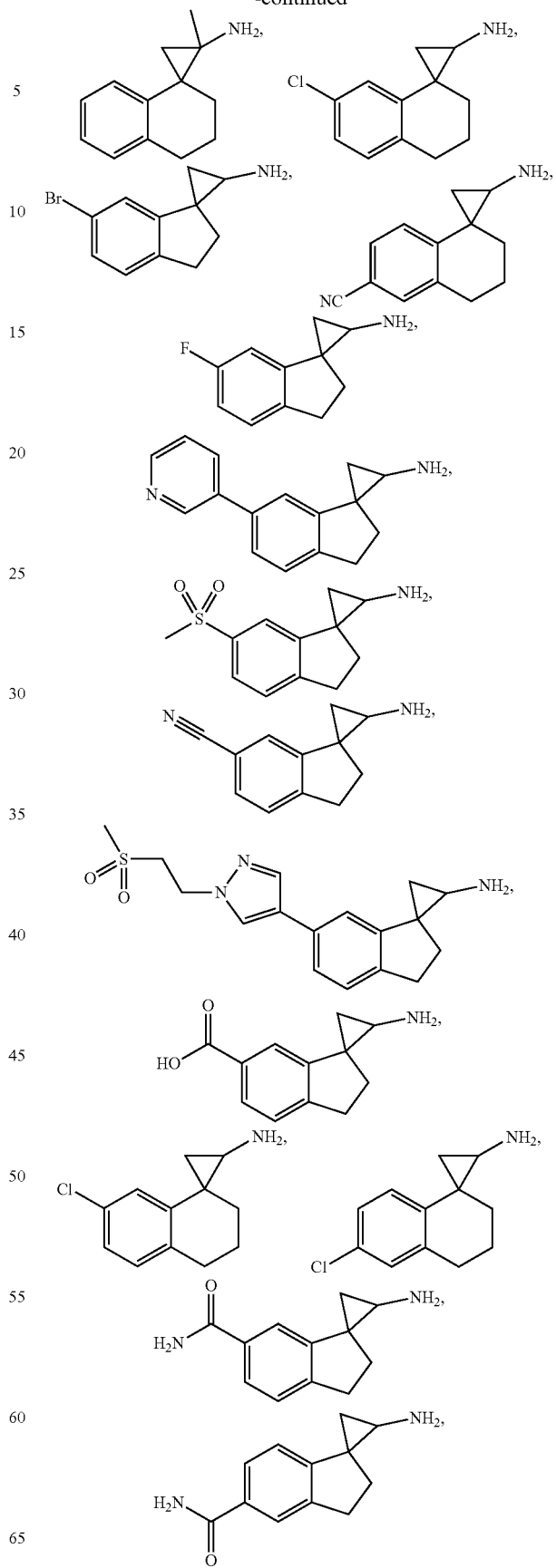

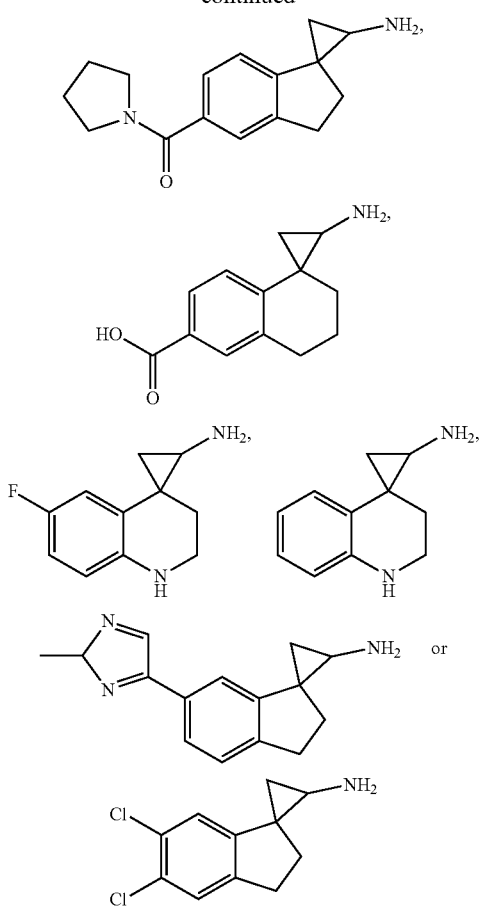
or a salt thereof.
16. The compound of claim 1 which is:
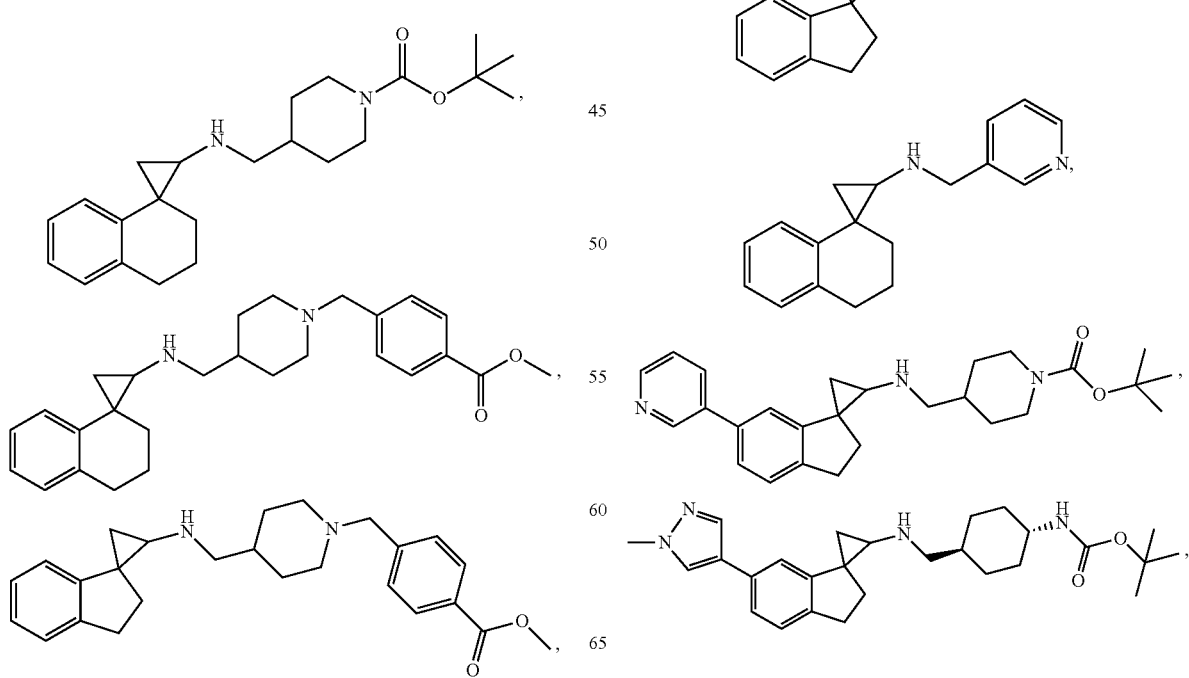

167
-continued
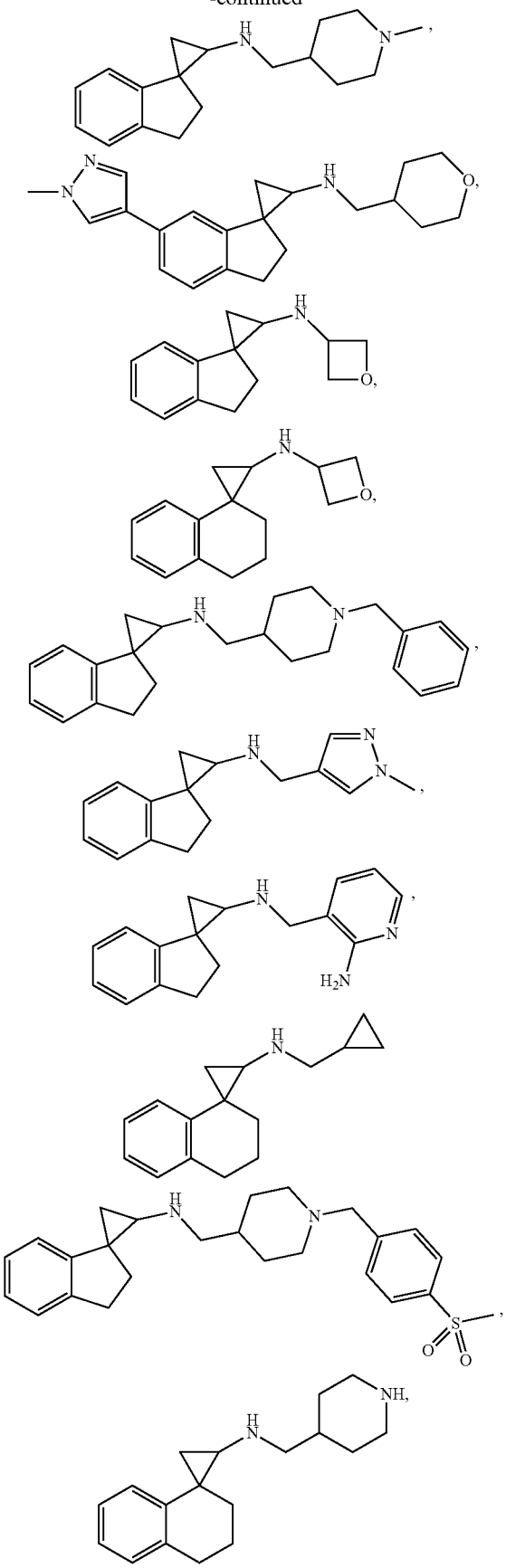
168
-continued
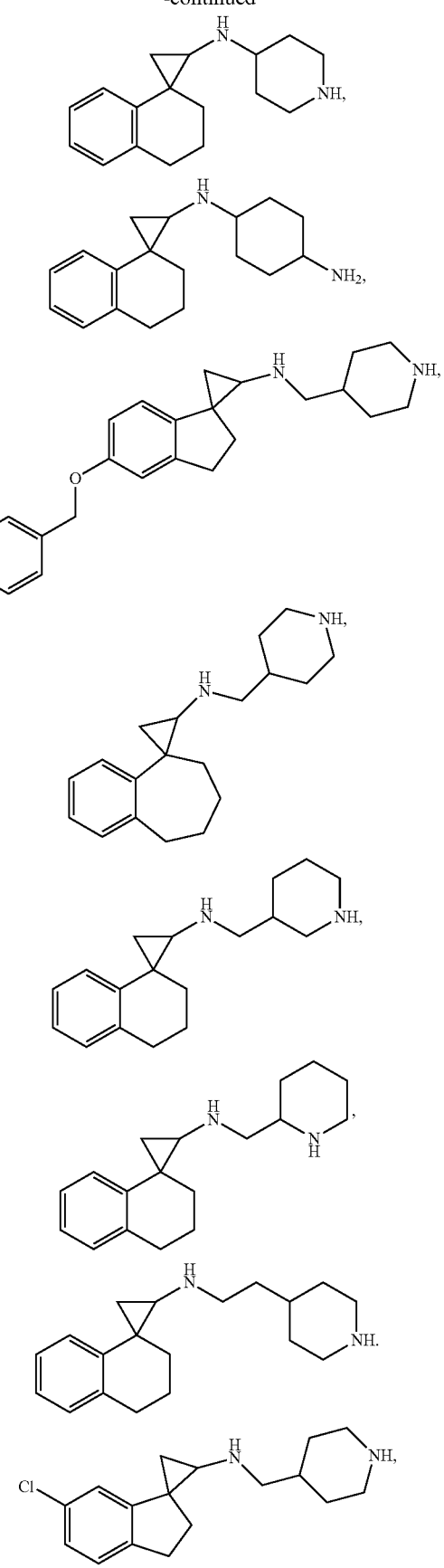

-continued
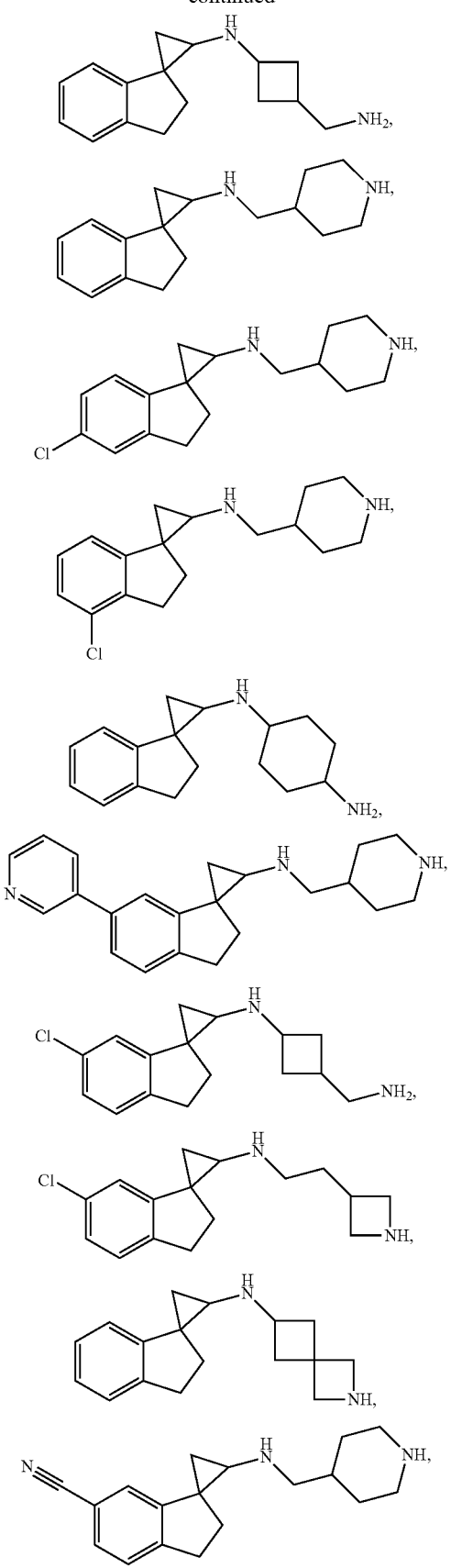
-continued
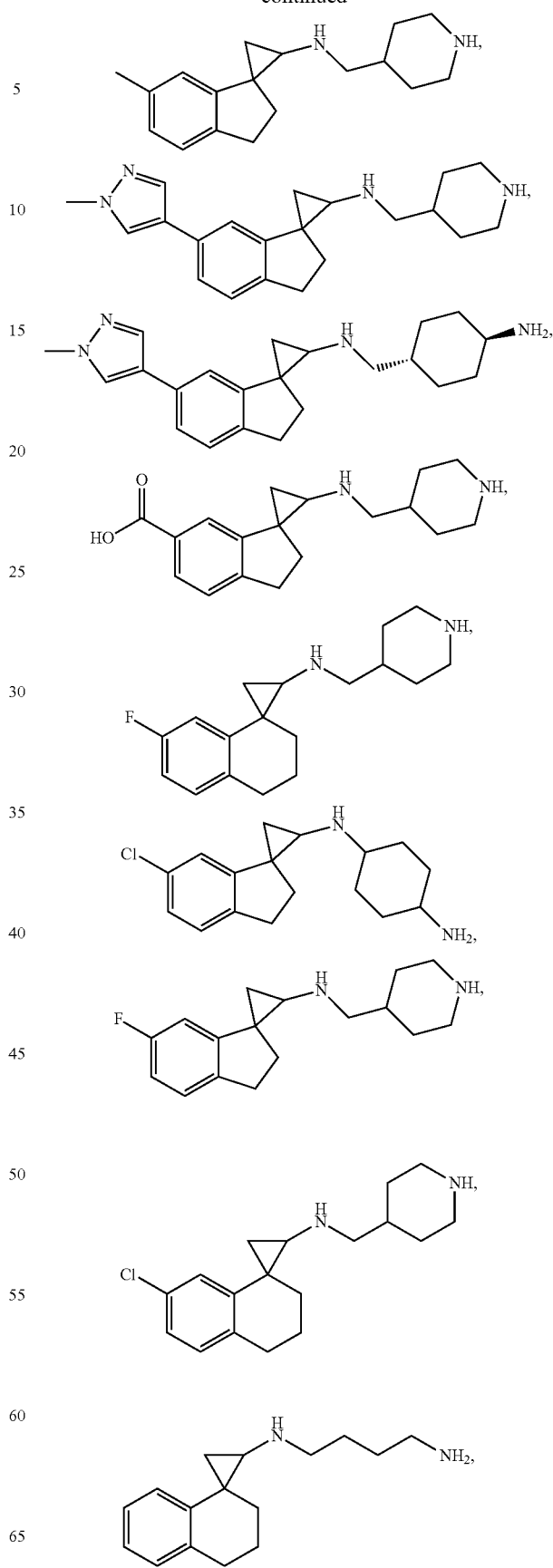

-continued

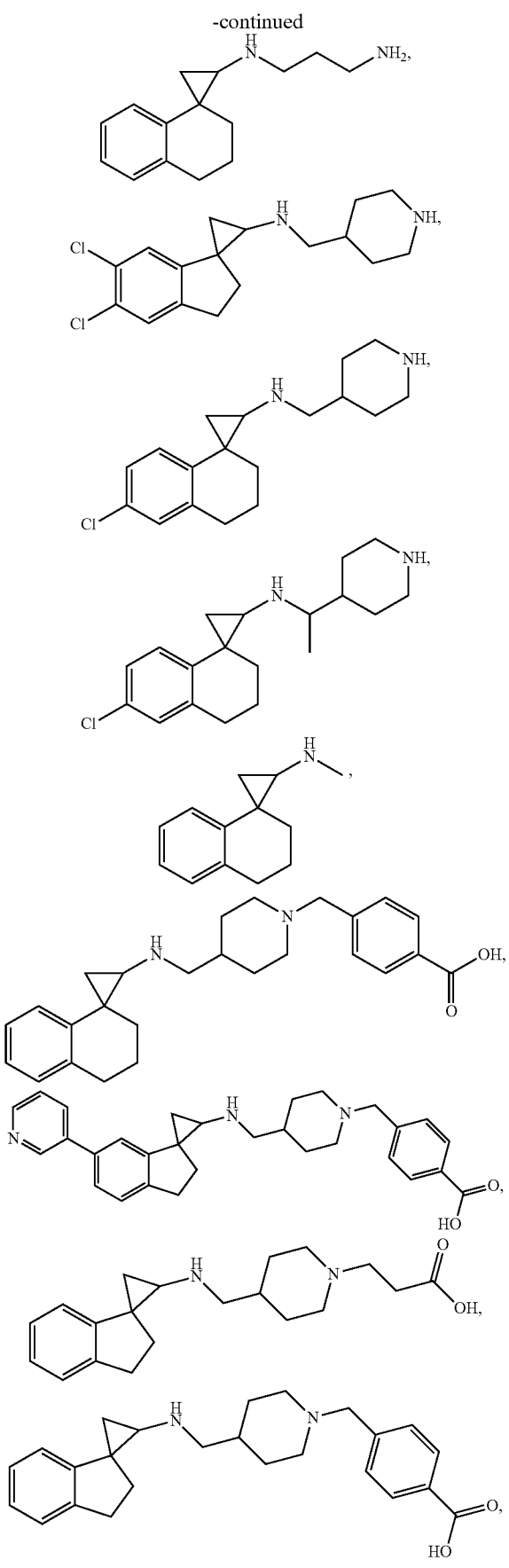

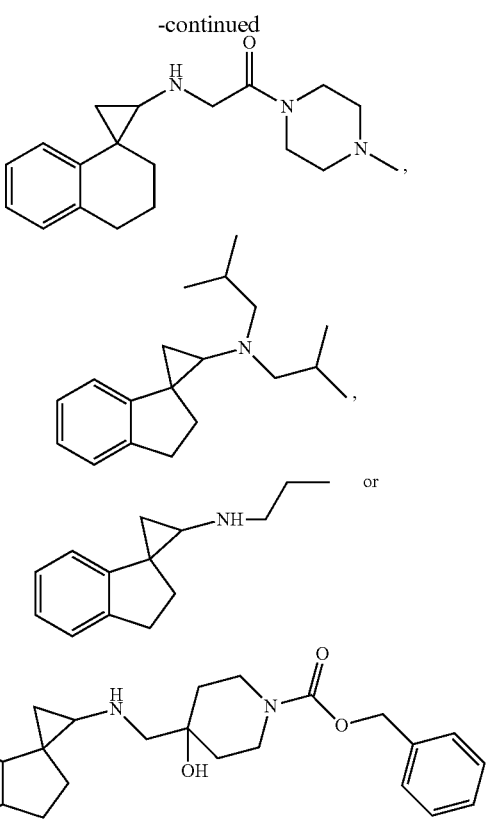

or a salt thereof.

17. A pharmaceutical composition comprising a compound of formula I:

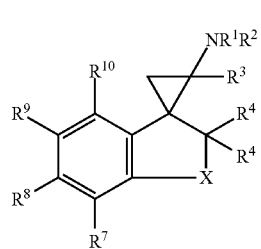

or a pharmaceutically acceptable salt thereof and a pharmaceutically acceptable carrier;
wherein:
X is, —C(R$^5$)$_2$—, —(C(R$^5$)$_2$)$_2$—, —(C(R$^5$)$_2$)$_3$— or —N(R$^6$)C(R$^5$)$_2$—;
R$^1$ is hydrogen, C$_{1-6}$alkyl, C$_{2-6}$alkenyl, C$_{2-6}$alkynyl, carbocyclyl or heterocyclyl, wherein any C$_{1-6}$alkyl, C$_{2-6}$alkenyl or C$_{2-6}$alkynyl of R$^1$ is optionally substituted with one or more R$^{a1}$ groups; and wherein any carbocyclyl or heterocyclyl of R$^1$ is optionally substituted with one or more R$^{a2}$ groups;
R$^2$ is hydrogen or C$_{1-6}$alkyl;
R$^3$ is hydrogen or C$_{1-6}$alkyl;
each R$^4$ is independently selected from the group consisting of hydrogen, halogen and methyl;
each R$^5$ is independently selected from the group consisting of hydrogen, halogen and methyl;
R$^6$ is hydrogen, C$_{1-6}$alkyl or —C(O)OR$^{b1}$;

R$^7$ is hydrogen, halo, C$_{1-6}$alkyl, C$_{2-6}$alkenyl, C$_{2-6}$alkynyl, heterocyclyl, —OR$^{e1}$, CN, —C(O)—N(R$^{e2}$)$_2$, —S(O)$_2$—R$^{e2}$ or —C(O)—OR$^{e2}$, wherein any C$_{1-6}$alkyl, C$_{2-6}$alkenyl or C$_{2-6}$alkynyl of R$^7$ is optionally substituted with one or more R$^{e3}$ groups and wherein any heterocyclyl of R$^7$ is optionally substituted with one or more R$^{e4}$ groups;

R$^8$ is hydrogen, halo, C$_{1-6}$alkyl, C$_{2-6}$alkenyl, C$_{2-6}$alkynyl, heterocyclyl, —OR$^{d1}$, CN, —C(O)—N(R$^{d2}$)$_2$, —S(O)$_2$—R$^{d2}$ or —C(O)—OR$^{d2}$, wherein any C$_{1-6}$alkyl, C$_{2-6}$alkenyl or C$_{2-6}$alkynyl of R$^8$ is optionally substituted with one or more R$^{d3}$ groups and wherein any heterocyclyl of R$^8$ is optionally substituted with one or more R$^{d4}$ groups;

R$^9$ is hydrogen, halo, C$_{1-6}$alkyl, C$_{2-6}$alkenyl, C$_{2-6}$alkynyl, heterocyclyl, —OR$^{e1}$, CN, —C(O)—N(R$^{e2}$)$_2$, —S(O)$_2$—R$^{e2}$ or —C(O)—OR$^{e2}$, wherein any C$_{1-6}$alkyl, C$_{2-6}$alkenyl or C$_{2-6}$alkynyl of R$^9$ is optionally substituted with one or more R$^{e3}$ groups and wherein any heterocyclyl of R$^9$ is optionally substituted with one or more R$^{e4}$ groups;

R$^{10}$ is hydrogen, halo, C$_{1-6}$alkyl, C$_{2-6}$alkenyl, C$_{2-6}$alkynyl, heterocyclyl, —OR$^{f1}$, CN, —C(O)—N(R$^{f2}$)$_2$, —S(O)$_2$—R$^{f2}$ or —C(O)—OR$^{f2}$, wherein any C$_{1-6}$alkyl, C$_{2-6}$alkenyl or C$_{2-6}$alkynyl of R$^{10}$ is optionally substituted with one or more R$^{f3}$ groups and wherein any heterocyclyl of R$^{10}$ is optionally substituted with one or more R$^{f4}$ groups;

each R$^{a1}$ is independently halo, oxo, —N(R$^{a3}$)$_2$, carbocyclyl, or heterocyclyl, wherein any carbocyclyl or heterocyclyl of R$^{a1}$ is optionally substituted with one or more groups independently selected from the group consisting of halo, C$_{1-6}$alkyl, —N(R$^{a3}$)$_2$, —OR$^{a3}$, —C(O)OR$^{a3}$, —NR$^{a3}$C(O)OR$^{a3}$, —C$_{1-6}$alkylphenyl and —C$_{1-6}$alkylC(O)OR$^{a3}$ wherein the —C$_{1-6}$alkylphenyl is optionally substituted with one or more groups independently selected from the group consisting of halogen, C$_{1-6}$alkyl, —N(R$^{a3}$)$_2$, —C(O)OR$^{a3}$ and —S(O)$_2$—R$^{a3}$;

each R$^{a2}$ is independently halo, —N(R$^{a3}$)$_2$ or C$_{1-6}$alkyl, wherein any C$_{1-6}$alkyl of R$^{a2}$ is optionally substituted with one or more —N(R$^{a3}$)$_2$;

each R$^{a3}$ is independently hydrogen, C$_{1-6}$alkyl or —C$_{1-6}$alkylphenyl;

R$^{b1}$ is C$_{1-6}$alkyl or —C$_{1-6}$alkylphenyl;

R$^{c1}$ is hydrogen, C$_{1-6}$alkyl or heterocyclyl, wherein any alkyl of R$^{c1}$ is optionally substituted with one or more halo or phenyl, and wherein any heterocyclyl of R$^{c1}$ is optionally substituted with one or more C$_{1-6}$alkyl or —C(=O)OC$_{1-6}$alkyl;

each R$^{c2}$ is independently selected from the group consisting of hydrogen, C$_{1-6}$alkyl, C$_{2-6}$alkenyl and C$_{2-6}$alkynyl, or two R$^{c2}$ groups together with the nitrogen to which they are attached form a 3-7 membered heterocyclyl;

each R$^{c3}$ is independently selected from the group consisting of —S(O)$_2$—R$^{c2}$ and halo;

each R$^{c4}$ is independently selected from the group consisting of C$_{1-6}$alkyl and C$_{1-6}$haloalkyl, wherein any C$_{1-6}$alkyl of R$^{c4}$ is optionally substituted with one or more groups independently selected from the group consisting of C$_{1-6}$alkyl, halo and —S(O)$_2$—R$^{c2}$;

R$^{d1}$ is hydrogen, C$_{1-6}$alkyl or heterocyclyl, wherein any alkyl of R$^{d1}$ is optionally substituted with one or more halo or phenyl, and wherein any heterocyclyl of R$^{d1}$ is optionally substituted with one or more C$_{1-6}$alkyl or —C(=O)OC$_{1-6}$alkyl;

each R$^{d2}$ is independently selected from the group consisting of hydrogen, C$_{1-6}$alkyl, C$_{2-6}$alkenyl and C$_{2-6}$alkynyl, or two R$^{d2}$ groups together with the nitrogen to which they are attached form a 3-7 membered heterocyclyl;

each R$^{d3}$ is independently selected from the group consisting of —S(O)$_2$—R$^{d2}$ and halo;

each R$^{d4}$ is independently selected from the group consisting of C$_{1-6}$alkyl and C$_{1-6}$haloalkyl, wherein any C$_{1-6}$alkyl of R$^{d4}$ is optionally substituted with one or more groups independently selected from the group consisting of C$_{1-6}$alkyl, halo and —S(O)$_2$—R$^{d2}$;

R$^{e1}$ is hydrogen, C$_{1-6}$alkyl or heterocyclyl, wherein any alkyl of R$^{e1}$ is optionally substituted with one or more halo or phenyl, and wherein any heterocyclyl of R$^{e1}$ is optionally substituted with one or more C$_{1-6}$alkyl or —C(=O)OC$_{1-6}$alkyl;

each R$^{e2}$ is independently selected from the group consisting of hydrogen, C$_{1-6}$alkyl, C$_{2-6}$alkenyl and C$_{2-6}$alkynyl, or two R$^{e2}$ groups together with the nitrogen to which they are attached form a 3-7 membered heterocyclyl;

each R$^{e3}$ is independently selected from the group consisting of —S(O)$_2$—R$^{e2}$ and halo;

each R$^{e4}$ is independently selected from the group consisting of C$_{1-6}$alkyl and C$_{1-6}$haloalkyl, wherein any C$_{1-6}$alkyl of R$^{e4}$ is optionally substituted with one or more groups independently selected from the group consisting of C$_{1-6}$alkyl, halo and —S(O)$_2$—R$^{e2}$;

R$^{f1}$ is hydrogen, C$_{1-6}$alkyl or heterocyclyl, wherein any alkyl of R$^{f1}$ is optionally substituted with one or more halo or phenyl, and wherein any heterocyclyl of R$^{f1}$ is optionally substituted with one or more C$_{1-6}$alkyl or —C(=O)OC$_{1-6}$alkyl;

each R$^{f2}$ is independently selected from the group consisting of hydrogen, C$_{1-6}$alkyl, C$_{2-6}$alkenyl and C$_{2-6}$alkynyl, or two R$^{f2}$ groups together with the nitrogen to which they are attached form a 3-7 membered heterocyclyl;

each R$^{f3}$ is independently selected from the group consisting of —S(O)$_2$—R$^{f2}$ and halo; and each R$^{f4}$ is independently selected from the group consisting of C$_{1-6}$alkyl and C$_{1-6}$haloalkyl, wherein any C$_{1-6}$alkyl of R$^{f4}$ is optionally substituted with one or more groups independently selected from the group consisting of C$_{1-6}$alkyl, halo and —S(O)$_2$—R$^{f2}$.

18. A method of treating cancer in an animal comprising administering to the animal in need thereof a compound of formula I or a pharmaceutically acceptable salt thereof as described in claim 1, wherein the cancer is prostrate, breast, neuroblastoma, small-cell lung, bladder, head and neck, colon, serous ovary cancers or kidney Wilm's tumor.

19. A method of increasing efficacy of a cancer treatment comprising a cytotoxic agent in an animal with cancer comprising administering to the animal an effective amount of a compound of formula I or a pharmaceutically acceptable salt thereof as described in claim 1, wherein the cancer is prostrate, breast, neuroblastoma, small-cell lung, bladder, head and neck, colon, serous ovary cancers or kidney Wilm's tumor.

20. A method of extending the duration of response to a cancer therapy in an animal with cancer, comprising administering to the animal undergoing the cancer therapy a compound of formula I or a pharmaceutically acceptable salt thereof, as described in claim 1, wherein the duration of response to the cancer therapy when the compound of formula I is administered is extended over the duration of response to the cancer therapy in the absence of the administration of the compound of formula I or the pharmaceutically acceptable salt thereof, wherein the cancer is prostrate, breast, neuroblastoma, small-cell lung, bladder, head and neck, colon, serous ovary cancers or kidney Wilm's tumor.

21. The method of claim 18, wherein the animal is a human.

\* \* \* \* \*

UNITED STATES PATENT AND TRADEMARK OFFICE
CERTIFICATE OF CORRECTION

PATENT NO. : 10,301,253 B2  
APPLICATION NO. : 15/658219  
DATED : May 28, 2019  
INVENTOR(S) : Brian K. Albrecht et al.

Page 1 of 1

It is certified that error appears in the above-identified patent and that said Letters Patent is hereby corrected as shown below:

In the Claims

Column 171, Lines 24-31, Claim 16, please delete the following compound:

" 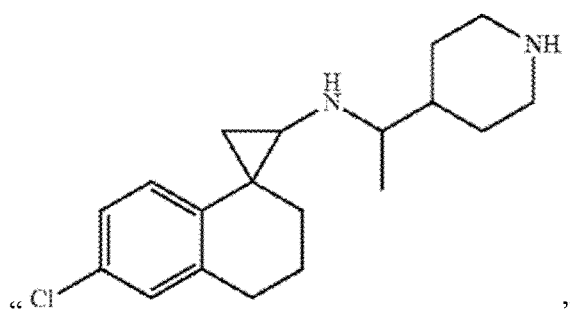 " and insert -- 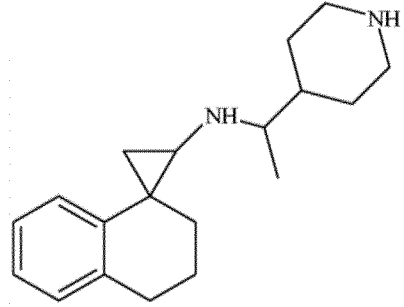 -- therefor.

Signed and Sealed this  
Twenty-fourth Day of September, 2019

Andrei Iancu  
*Director of the United States Patent and Trademark Office*